United States Patent
Daugan et al.

[11] Patent Number: 6,143,746
[45] Date of Patent: *Nov. 7, 2000

[54] TETRACYCLIC CYCLIC GMP-SPECIFIC PHOSPHODIESTERASE INHIBITORS, PROCESS OF PREPARATION AND USE

[75] Inventors: Alain Claude-Marie Daugan; Francoise Gellibert, both of Marly le Roi Cedex, France

[73] Assignee: ICOS Corporation, Bothell, Wash.

[*] Notice: This patent is subject to a terminal disclaimer.

[21] Appl. No.: 09/154,051

[22] Filed: Sep. 16, 1998

Related U.S. Application Data

[63] Continuation-in-part of application No. PCT/EP95/00183, Jan. 19, 1995, Pat. No. 5,859,006, which is a continuation-in-part of application No. PCT/EP96/03025, Jul. 11, 1996, Pat. No. 5,981,527, which is a continuation-in-part of application No. PCT/EP96/03024, Jul. 11, 1996.

[30] Foreign Application Priority Data

Jan. 21, 1994 [GB] United Kingdom ............ 9401090
Jul. 14, 1995 [GB] United Kingdom ............ 9514465
Jul. 14, 1995 [GB] United Kingdom ............ 9514474

[51] Int. Cl.$^7$ .................................................. A61K 31/50
[52] U.S. Cl. ........................ 514/249; 514/250; 514/292
[58] Field of Search ........................ 514/249, 250, 514/292

[56] References Cited

U.S. PATENT DOCUMENTS

| | | | |
|---|---|---|---|
| 3,644,384 | 2/1972 | Schulenberg | 260/295 C |
| 3,717,638 | 2/1973 | Schulenberg | 260/268 PC |
| 3,917,599 | 11/1975 | Saxena et al. | 260/268 PC |
| 4,188,390 | 2/1980 | Campbell | 424/251 |
| 4,686,228 | 8/1987 | Campbell et al. | 514/307 |
| 4,801,587 | 1/1989 | Voss et al. | 514/248 |
| 5,145,852 | 9/1992 | Virag | 514/253 |
| 5,270,323 | 12/1993 | Milne, Jr. et al. | 514/309 |
| 5,770,606 | 6/1998 | El-Rashidy et al. | 514/284 |
| 5,859,006 | 1/1999 | Daugan | 514/249 |
| 5,874,437 | 2/1999 | Garvey et al. | 514/258 |

FOREIGN PATENT DOCUMENTS

| | | |
|---|---|---|
| 0 357 122 | 3/1990 | European Pat. Off. . |
| 0 362 555 | 4/1990 | European Pat. Off. . |
| 459 666 | 4/1991 | European Pat. Off. . |
| 463 756 | 2/1992 | European Pat. Off. . |
| 526 004 | 3/1993 | European Pat. Off. . |
| 0 611 248 A1 | 8/1994 | European Pat. Off. . |
| 42 20 264 A1 | 12/1993 | Germany . |
| 03044324 | 2/1991 | Japan . |
| 1454171 | 10/1976 | United Kingdom . |
| WO 94/05661 | 3/1974 | WIPO . |
| WO 89/10123 | 11/1989 | WIPO . |
| WO 92/11851 | 7/1992 | WIPO . |
| WO 94/28902 | 12/1994 | WIPO . |
| WO 95/05172 | 2/1995 | WIPO . |
| WO 95/11683 | 5/1995 | WIPO . |
| WO 95/19978 | 7/1995 | WIPO . |
| WO 98/31368 | 7/1995 | WIPO . |
| WO 95/29172 | 11/1995 | WIPO . |
| WO 96/27372 | 9/1996 | WIPO . |
| WO 96/28142 | 9/1996 | WIPO . |
| WO 96/34583 | 11/1996 | WIPO . |
| WO 96/38131 | 12/1996 | WIPO . |
| WO 97/03675 | 2/1997 | WIPO . |
| WO 97/03985 | 2/1999 | WIPO . |

OTHER PUBLICATIONS

A. Bowman et al., *Br. J. Pharmac.*, (1984), 81, 665–674.
F. Trigo–Rocha et al., *Am. J. Physiol.*, (Feb. 1993), 264, H419–H422.
J. Reiser et al., *Br. J. Dis. Chest*, (1986), 80, 157–163.
P. Bush et al., *J. Urol.*, (Jun. 1992), 147, 1650–1655.
F. Holmquist et al., *J. Urol.* (Oct. 1993), 150, 1310–1315.
R. Rudd et al., *Br. J. Dis. Chest*, (1983), 77, 78–86.

(List continued on next page.)

*Primary Examiner*—Marianne M. Cintins
*Assistant Examiner*—C. Delacroix-Muirheid
*Attorney, Agent, or Firm*—Marshall, O'Toole, Gerstein, Murray & Borun

[57] ABSTRACT

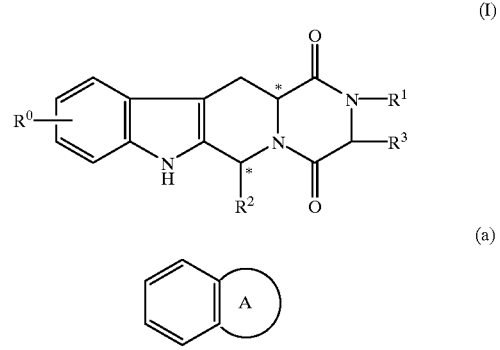

A compound of formula (I) and salts and solvates thereof, in which: $R^0$ represents hydrogen, halogen, or $C_{1-6}$alkyl; $R^1$ represents hydrogen, $C_{1-6}$alkyl, $C_{2-6}$alkenyl, $C_{2-6}$alkynyl, halo$C_{1-6}$alkyl, $C_{3-8}$cycloalkyl, $C_{3-8}$cycloalkyl$C_{1-3}$alkyl, aryl$C_{1-3}$alkyl, or heteroaryl$C_{1-3}$alkyl; $R^2$ represents an optionally substituted monocyclic aromatic ring selected from benzene, thiophene, furan, and pyridine, or an optionally substituted bicyclic ring (a) attached to the rest of the molecule via one of the benzene ring carbon atoms, and wherein the fused ring (A) is a 5- or 6-membered ring which may be saturated or partially or fully unsaturated, and comprises carbon atoms and optionally one or two heteroatoms selected from oxygen, sulphur, and nitrogen; and $R^3$ represents hydrogen or $C_{1-3}$alkyl, or $R^1$ and $R^3$ together represent a 3- or 4-membered alkyl or alkenyl chain. A compound of formula (I) is a potent and selective inhibitor of cyclic guanosine 3',5'-monophosphate specific phosphodiesterase (cGMP specific PDE) having a utility in a variety of therapeutic areas where such inhibition is beneficial, including the treatment of cardiovascular disorders and erectile dysfunction.

13 Claims, No Drawings

OTHER PUBLICATIONS

E. McMahon et al., *J. Pharmacol. Exp. Thera.*, (1989), 251, 1000–1005.
F. Holmquist et al., *Acta Physiol. Scand.*, (1991), 143, 299–304.
G. Barbanti, *Urol. Res.*, (1988), 16, 299–302.
L. Ignarro et al., *Biochem. and Biophys. Res. Comm.*, (1990), 170(2), 843–850.
J. Krall et al., *Bio. Reprod.*, (1988), 39, 913–922.
M. Wilkins et al., *Proc. Natl. Acad. Sci., USA*, (Aug. 1990), 87, 6465–6469.
M. Wilkins et al., *J. Clin. Invest.*, (Apr. 1990), 85, 1274–1279.
J. Rajfer, *N. Eng. J. Med.*, (Jan. 1992), 326(2), 90–94.
H. Knispel, *Urol. Res.*, (1992), 20, 253–257.
G. Gwinup, *Annals. of Internal Medicine*, (Jul. 1988), 162–163.
A. Zorgniotti, *J. Urol.*, (Apr. 1992), 147(4), 308A.
K. Azadzoi et al., *J. Urol.*, (Nov. 1992), 148, 1587–1591.
K. Azadzoi et al., *J. Urol.*, (Jan. 1992), 147, 220–225.
C. Sparwasser et al., *J. Urol.*, (Dec. 1994), 152, 2159–2163.
T. Lue, "Campbell's Urology," 6th Ed., Chap. 16, P. Walsh et al., Eds., W.B. Saunders Co., 709–728 (1991).
N. Kim et al., *J. Clin. Invest.*, (1991), 88, 112–118.
S. Francis et al., in J. Beavo et al. eds. "Cyclic Nucleotide PDEs," Ch. 5 (1990) 117–140.
R. Weishaar et al., *J. Med. Chem.*, (1985), 28:5, 537–542.
H. Ahn et al., *Biochem. Pharmacol.*, (1989), 39:19, 3331–3339.
C. Lugnier et al., *Biochem. Pharmacol.*, (1986), 35:10, 1743–1751.
J. Doremieux et al., *Ann. Urol. Paris*, (1987), 21(6), 429–434.
D. Green et al., *Geriatrics*, (Jan. 1993), 48(1), 46–58.
M. Webster et al., *Hematol. Oncol. Cl. of N. Am.*, (Feb. 1990), 4(1), 265–289.
F. Holmquist et al., *Acta. Physiol. Scand.*, (1991), 141, 441–442.
J. Taher et al., *J. Urol.*, (Apr. 1993), 149, 285A.
S. Uckert et al., *J. Urol.*, 151 (5 Supp.), (1994), 495A.
W. Aronson et al., *J. Urol.*, (1991), 145 (4 Supp.), 341A.
P. Bush et al., *Fed. Am. Soc. Exp. Biol.*, (1991), 5(4), 175.
P. Bush et al., *Fed. Am. Soc. Exp. Biol.*, (1992), 6(4), 2092.
W. Aronson et al., *J. Urol.*, (1992), 147 (4 Supp.), 454A.
P. Bush et al., *Circulation*, (May 1993), 87 Supp. V, V–30–V–32.
R. Pickard et al., *J. Urol.*, (May 1993) 149 (4 Supp.), 245A.
R. Pickard et al., *Clin. Pharmacol.*, (Jan. 1993), 35(5), 536P–537P.
F. Trigo–Rocha et al., *J. Urol.*, (Apr. 1993), 149, 872–877.
M. Krupp et al., *J. Cardiovas. Pharmacol.*, (1989), 13 (Supp. 2), S11–S19.
"Physician' Desk Reference," (1992), 683,1099–1100, 1344, 1941–1943.
R. Morales et al., *World J. Urol.*, (1990), 8, 80–83.
J. Cortijo, *Br. J. Pharmacol.*, (Feb. 1993), 108(2), 562–568.
E. Kim et al., *J. Urol.*, (1995), 153, 361–365.
S. Korenman et al., *JAGS*, (Apr. 1993), 41(4), 363–366.
K. Allenby et al., *Angiology*, (1991), 42, 418–420.
H. Hamilton et al., *J. Med. Chem.*, (1987), 30, 91–96.
H. Padma–Nathan et al., *Sem. in Urol.*, (Nov. 1986), vol. IV, No. 4, 236–238.
J. Beavo et al., *TiPS*, (Apr. 1990), 11, 150–155.
S. Korenman et al., *Clin. Res.*, (1988), 36, 123A.
D. Halsted et al., *J. Urol.*, (Jul. 1986), 136, 109–110.
W. Thompson, *Pharmac. Ther.*, (1991), 51, 13–33.
M. Giembycz et al., *Clin. and Exper. Allergy*, (1992), 22, 337–344.
C. Nicholson et al., *TIPS*, (Jan. 1991), 12, 19–27.
J. LeBlanc et al., *Eur. J. Cardiothorac Surg.*, (1993), 7, 211–215.
C. Stief et al., *J. Urol.*, (Nov. 1992), 148, 1437–1440.
C. Stief et al., *World J. Urol.*, (1991), 9, 237–239.
C. Clyne et al., *Br. J. Surg.*, (Apr. 1987), 74, 246–248.
V. Mirone et al., *Acta. Urol. Ltd.*, (1992), Suppl. 4, 11–12.
P. Bush, Ph.D. Thesis (1992), pp. 159–160.
T. Lincoln, *Pharmac. Ther.*, (1989), 41, 479–502.
J. Heaton et al., *Urology*, (Feb. 1995), 45(2), 200–206.
Saxena et al., *Journal of Medicinal Chemistry*, vol. 16, No. 5, 560–564 (1973).
Ishida et al., *Chem. Pharm. Bull.*, vol. 33, No. 8, 3237–3249 (1985).
Gillespie et al., *Molecular Pharmacology*, 36:773–781 (1989).
Braña et al., *Synthetic Communications*, 20(12), 1793–1820 (1990).
Dellouve–Courillon et al., *Tetrahedron*, 46, No. 9, 3245–3266 (1990).
Murray, *DN&P* 6(3), 150–156 (1993).
Zorgniotti et al. *Int. J. Impotence Res.*, 6, 33–36 (1994).
Beyer et al., *Phys. and Behav.*, (1981), 27, 731–733.
Pickard et al., *Br. J. Pharmacol.*, (1991), 104 755–759.
Martinez–Pineiro et al., *Eur. Urol.*, (1993), 24, 492–499.
Mirone et al., *Br. J. Urol.*, (Mar., 1993), 71(3), 365.
Murray et al., *Biochemical Soc. Trans.*, (1992), 20, 460–464.
Raeburn et al., *Prog. Drug Res.*, (1993), 12–32.
Merkel, *Cardio. Drug. Rev.*, (1993), 11(4), 501–515.
"Physicians' Desk Reference," (1992) 2207–2208.
Cimino et al., *Biochem. Pharmacology*, (1988), 37(14), 2739–2745.
Watanabe et al., *Federation Proceedings*, (1982), 41(7), 2292–2399.
Earl et al., *Life Sciences*, (1984), 35, 525–534.
Brindley, *Brit. J. Phychiat.*, (1983), 143, 332–337.
Keogh, *Aust. NZ. J. Med.*, (1989), 19, 108–112.
Funderbunk, *New Engl. J. Med.*, (1974), 290, 630–631.
Beretta, *Acta European Fertilitatis*, (1986), 17, 43–45.
"Physicians' Desk Reference," (1992), 1778–1779.
Hess in "Prazosin: Evaluation of a New Antihypertensive Agent," D. Cotton ed., American Elsevier, NY, (1974), 3–15.
Dadkar et al., *Ind. J. Exp. Biol.*, (1982), 20, 484–487.
D'Armiento et al., *Eur. J. Pharmacol.*, (1980), 65, 234–247.
Bhalla et al., *Brit. Med. J.*, (1979), 2, 1059.
Burke et al., *Med. J. Aust.*, (1980), 382–383.
Segasouthy et al., *Med. J. Malaysia*, (1982), 37(4), 384.
Ylitalo et al., *Acta Med. Scand.*, (1983), 213, 319–320.
Robbins et al., *J. Urol.*, (1983), 130, 975.
Adams et al., *J. Urol.*, (1984), 132, 1208.
Russell et al., *Med. J. Aust.*, (1985), 143, 321.
Taher et al., *Int. J. Impotence Res., Abstracts*, Milan, Italy (Sep. 14–17, 1992).
Trigo–Rocha et al., *Neurology and Urodynamics*, 13, (1998) 71–80.

TETRACYCLIC CYCLIC GMP-SPECIFIC PHOSPHODIESTERASE INHIBITORS, PROCESS OF PREPARATION AND USE

CROSS REFERENCE TO RELATED APPLICATION

This is a continuation-in-part of PCT application Ser. No. PCT/EP95/00183, filed Jan. 19, 1995, (U.S. Ser. No. 08/669,389), now U.S. Pat. No. 5,859,006, a continuation-in-part of PCT application Ser. No. PCT/EP96/03025, filed Jul. 11, 1996, (U.S. Ser. No. 09/000,192), now U.S. Pat. No. 5,981,527, and a continuation-in-part of PCT application Ser. No. PCT/EP96/03024, filed Jul. 11, 1996, (U.S. Ser. No. 08/981,989), pending.

FIELD AND BACKGROUND OF THE INVENTION

This invention relates to a series of tetracyclic derivatives, to processes for their preparation, pharmaceutical compositions containing them, and to their use as therapeutic agents. In particular, the invention relates to tetracyclic derivatives that are potent and selective inhibitors of cyclic guanosine 3',5'-monophosphate specific phosphodiesterase (cGMP-specific PDE) having utility in a variety of therapeutic areas where such inhibition is thought to be beneficial, including the treatment of cardiovascular disorders and erectile dysfunction.

SUMMARY OF THE INVENTION

Thus, according to a first aspect, the present invention provides compounds of formula (I)

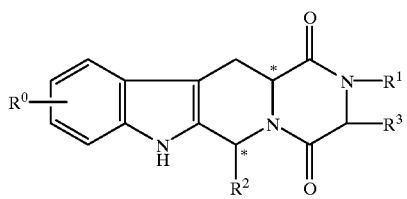

(I)

and salts and solvates (e.g., hydrates) thereof, in which:
$R^0$ represents hydrogen, halogen, or $C_{1-6}$alkyl;
$R^1$ represents hydrogen, $C_{1-6}$alkyl, $C_{2-6}$alkenyl, $C_{2-6}$alkynyl, halo$C_{1-6}$alkyl, $C_{3-8}$cycloalkyl, $C_{3-8}$cycloalkyl$C_{1-3}$alkyl, aryl$C_{1-3}$alkyl, or heteroaryl$C_{1-3}$alkyl;
$R^2$ represents an optionally substituted monocyclic aromatic ring selected from benzene, thiophene, furan, and pyridine, or an optionally substituted bicyclic ring

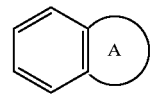

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur, and nitrogen; and
$R^3$ represents hydrogen of $C_{1-3}$alkyl, or $R^1$ and $R^3$ together represent a 3- or 4-membered alkyl or alkenyl chain.

There is further provided by the present invention a subgroup of compounds for formula (I), the subgroup comprising compounds of formula (Ia)

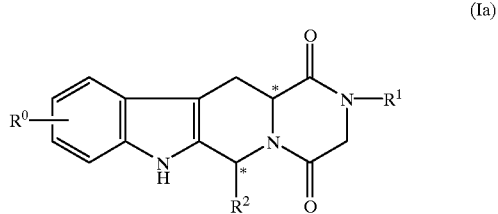

(Ia)

and salts and solvates (e.g., hydrates) thereof, in which:
$R^0$ represents hydrogen, halogen, or $C_{1-6}$alkyl;
$R^1$ represents hydrogen, $C_{1-6}$alkyl, halo$C_{1-6}$alkyl, $C_{3-8}$cycloalkyl$C_{1-3}$alkyl, aryl$C_{1-3}$alkyl, or heteroaryl$C_{1-3}$alkyl; and
$R^2$ represents an optionally substituted monocyclic aromatic ring selected from benzene, thiophene, furan, and pyridine, or an optionally substituted bicyclic ring

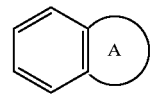

attached to the rest of the molecule via one of the benzene ring carbon atoms, and wherein the fused ring A is a 5- or 6-membered ring which can be saturated or partially or fully unsaturated and comprises carbon atoms and optionally one or two heteroatoms selected from oxygen, sulphur, and nitrogen.

There is yet further provided by the present invention a further subgroup of compounds of formula (I), the compounds comprising compounds of formula (Ib)

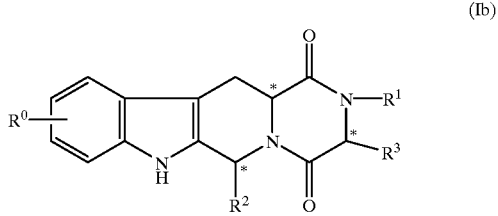

(Ib)

and solvates (e.g., hydrates) thereof, in which:
$R^0$ represents hydrogen, halogen, or $C_{1-6}$alkyl;
$R^1$ represents hydrogen or $C_{1-6}$alkyl;
$R^2$ represents the bicyclic ring which can be optionally substituted by one or more groups selected from halogen and $C_{1-3}$alkyl; and
$R^3$ represents hydrogen or $C_{1-3}$alkyl.

Within $R^1$ above, the term "aryl" as part of an aryl$C_{1-3}$alkyl group means phenyl or phenyl substituted by one or more (e.g., 1, 2, or 3) substituents selected from halogen, $C_{1-6}$alkyl, $C_{1-6}$alkoxy, and methylenedioxy. The term "heteroaryl" as part of a heteroaryl$C_{1-3}$alkyl group means thienyl, furyl, or pyridyl, each optionally substituted by one or more (e.g., 1, 2, or 3) substituents selected from halogen, $C_{1-6}$alkyl, and $C_{1-6}$alkoxy. The term "$C_{3-8}$cycloalkyl" as a group or part of a $C_{3-8}$cycloalkyl$C_{1-3}$alkyl group means a monocyclic ring comprising three to eight carbon atoms. Examples of suitable cycloalkyl rings include the $C_{3-6}$cycloalkyl rings cyclopropyl, cyclobutyl, cyclopentyl, and cyclohexyl.

Within $R^2$ above, optional benzene ring substituents are selected from one or more (e.g., 1, 2, or 3) atoms or groups comprising halogen, hydroxy, $C_{1-6}$alkyl, $C_{1-6}$alkoxy, $CO_2R^b$, halo$C_{1-6}$alkyl, halo$C_{1-6}$alkoxy, cyano, nitro, and $NR^aR^b$, where $R^a$ and $R^b$ are each hydrogen or $C_{1-6}$alkyl, or $R^a$ also can represent $C_{2-7}$alkanoyl or $C_{1-6}$alkylsulphonyl. Optional substituents for the remaining ring systems are selected from one or more (e.g., 1, 2, or 3) atoms or groups comprising halogen, $C_{1-6}$alkyl, $C_{1-6}$alkoxy, and aryl$C_{1-3}$alkyl as defined above. The bicyclic ring

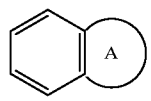

can, for example, represent naphthalene, a heterocycle such as benzoxazole, benzothiazole, benzisoxazole, benzimidazole, quinoline, indole, benzothiophene, benzofuran, or

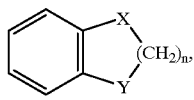

wherein n is an integer 1 or 2 and X and Y each can represent $CH_2$, O, S, or NH.

In the above definitions, the term "alkyl," as a group or part of a group, means a straight chain or, where available, a branched chain moiety containing the indicated number of carbon atoms. For example, it can represent a $C_{1-4}$alkyl function as represented by methyl, ethyl, n-propyl, i-propyl, n-butyl, s-butyl, and t-butyl. The term "alkenyl" as used herein includes straight chained and branched alkenyl groups containing the indicated number of carbon atoms, such as vinyl and allyl groups. The term "alkynyl" as used herein includes straight chained and branched alkynyl groups containing the indicated number of carbon atoms, suitably acetylene.

The term "halogen" herein means a fluorine, chlorine, bromine, or iodine atom.

The term "halo$C_{1-6}$alkyl" means an alkyl group as defined above comprising one to six carbon atoms substituted at one or more carbon atoms by one or more (e.g., 1, 2, or 3) halogen atoms. Similarly, a halo$C_{1-6}$alkoxy group is a halo$C_{1-6}$alkyl group as defined above linked to the $R^2$ benzene ring via an oxygen atom. Examples of halo$C_{1-6}$alkyl groups include trifluoromethyl and 2,2,2-trifluoroethyl. An example of a halo$C_{1-6}$alkoxy group is trifluoromethoxy. The term "$C_{2-7}$alkanoyl" means a $C_{1-6}$alkanoyl group where the $C_{1-6}$alkyl portion is as defined above. An example of a suitable $C_{2-7}$alkanoyl group is the $C_2$alkanoyl group acetyl.

When $R^0$ is a halogen atom or a $C_{1-6}$alkyl group, this substituent can be sited at any available position on the phenyl portion of the tetracyclic ring. However, a particular site of attachment is the ring 10-position.

The compounds of formula (I) can contain two or more asymmetric centers, and, thus, can exist as enantiomers or diastereoisomers. In particular, in formula (I) above, two ring chiral centers are denoted with asterisks. It is to be understood that the invention includes both mixture and separate individual isomers of the compounds of formula (I).

The compounds of formula (I) also can exist in tautomeric forms, and the invention includes both mixtures and separate individual tautomers thereof.

The pharmaceutically acceptable salts of the compounds of formula (I) which contain a basic center are acid addition salts formed with pharmaceutically acceptable acids. Examples include the hydrochloride, hydrobromide, sulfate or bisulfate, phosphate or hydrogen phosphate, acetate, benzoate, succinate, fumarate, maleate, lactate, citrate, tartrate, gluconate, methanesulphonate, and p-toluenesulphonate salts. Compounds of formula (I) also can provide pharmaceutically acceptable metal salts, in particular alkali metal salts, with bases. Examples include the sodium and potassium salts.

A particular group of compounds of the invention are those compounds of formula (I) in which $R^0$ is hydrogen or halogen (e.g., fluorine), especially hydrogen.

Another particular group of compounds of the invention are those compounds of formula (I) in which $R^1$ represents hydrogen, $C_{1-4}$alkyl, halo$C_{1-4}$alkyl, $C_{3-6}$cycloalkyl, $C_{3-6}$cycloalkylmethyl, pyridyl$C_{1-3}$alkyl, furyl$C_{1-3}$alkyl, or optionally substituted benzyl. Within this particular group of compounds, examples of $C_{1-4}$alkyl groups are methyl, ethyl, n-propyl, i-propyl, and n-butyl. Examples of $C_{3-6}$cycloalkylmethyl groups are cyclopropylmethyl and cyclohexylmethyl. Examples of optionally substituted, benzyl groups include benzyl and halobenzyl (e.g., fluorobenzyl).

A further group of compounds of the invention are those compounds of formula (I) in which $R^2$ represents an optionally substituted benzene, thiophene, furan, pyridine, or naphthalene ring, or an optionally substituted bicyclic ring

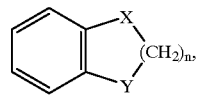

wherein n is 1 or 2, and X and Y are each $CH_2$ or O. Within this particular group of compounds, examples of substituted benzene groups are benzene substituted by one of halogen (e.g., chlorine), hydroxy, $C_{1-3}$alkyl (e.g., methyl, ethyl, or i-propyl), $C_{1-3}$alkoxy (e.g., methoxy or ethoxy), $CO_2R^b$, halomethyl (e.g., trifluoromethyl), halomethoxy (e.g., trifluoromethoxy), cyano, nitro, or $NR^aR^b$ wherein $R^a$ and $R^b$ are each hydrogen or methyl, or $R^a$ is acetyl, or benzene substituted by dihalo (e.g., dichloro) or by $C_{1-3}$alkoxy (e.g., methoxy) and one of halogen (e.g., chlorine) and hydroxy. An example of a substituted thiophene ring is a halo (e.g., bromo) substituted thiophene ring.

A still further particular group of compounds of formula (I) are those where $R^3$ represents hydrogen or $R^1$ and $R^3$ together represent a 3-membered alkyl chain.

A preferred group of compounds of the invention are the cis isomers of formula (I) represented by formula (Ic)

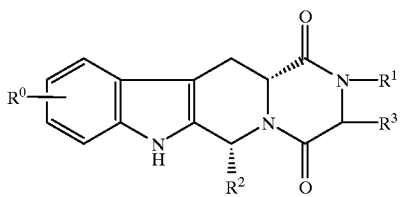

(Ic)

and mixtures thereof with their cis optical enantiomers, including racemic mixtures, and salts and solvates (e.g., hydrates) of these compounds in which $R^0$ is hydrogen or halogen (e.g., fluorine), especially hydrogen, and $R^1$, $R^2$, and $R^3$ are as defined previously.

The single isomers represented by formula (Ic), i.e., the 6R, 12aR isomers, are particularly preferred.

Within the above definitions, $R^1$ preferably can represent $C_{1-4}$alkyl (e.g., methyl, ethyl, i-propyl, and n-butyl), $C_{3-6}$cycloalkyl (e.g., cyclopentyl) or $C_{3-6}$cycloalkylmethyl (e.g., cyclopropylmethyl).

$R^2$ preferably can represent a substituted benzene ring such as benzene substituted by $C_{1-3}$alkoxy (e.g., methoxy) or by $C_{1-3}$alkoxy (e.g., methoxy) and halogen (e.g., chlorine), particularly 4-methoxyphenyl or 3-chloro-4-methoxyphenyl, or $R^2$ preferably can represent 3,4-methylenedioxyphenyl.

A particularly preferred subgroup of compounds according to the present invention are compounds wherein $R^0$ represents hydrogen.

A further preferred subgroup includes compounds wherein $R^1$ is selected from hydrogen, methyl, and isopropyl.

Preferably, $R^2$ represents the unsubstituted bicyclic ring

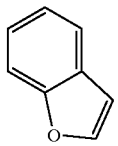

A still further subgroup of compounds of formula (I), are compounds wherein $R^3$ represents hydrogen or methyl.

It is to be understood that the present invention covers all appropriate combinations of particular and preferred groupings hereinabove.

Particular individual compounds of the invention include:

cis-2,3,6,7,12,12a-hexahydro-2-(4-pyridyl-methyl)-6-(3, 4-methylenedioxyphenyl)-pyrazino[2',1';6,1]-pyrido[3, 4-b]indole-1,4-dione;

cis-2,3,6,7,12,12a-hexahydro-6-(2,3-dihydrobenzo[b]furan-5-yl)-2-methyl-pyrazino[2',1';6,1]pyrido-[3,4-b]indole-1,4-dione;

cis-2,3,6,7,12,12a-hexahydro-6-(5-bromo-2-thienyl)-2-methylpyrazino[2',1';6,1]pyrido[3,4-b]indole-1,4-dione;

cis-2,3,6,7,12,12a-hexahydro-2-butyl-6-(4-methylphenyl)-pyrazino[2',1';6,1]pyrido[3,4-b]indole-1,4-dione;

(6R,12aR)-2,3,6,7,12,12a-hexahydro-2-isopropyl-6-(3,4-methylenedioxyphenyl)-pyrazino[2',1';6,1]pyrido-[3,4-b]indole-1,4-dione;

(6R,12aR)-2,3,6,7,12,12a-hexahydro-2-cyclopentyl-6-(3, 4-methylenedioxyphenyl)-pyrazino[2',1';6,1]-pyrido[3, 4-b]indole-1,4-dione;

(6R,12aR)-2,3,6,7,12,12a-hexahydro-2-cyclopropylmethyl-6-(4-methoxyphenyl)-pyrazino[2', 1';6,1]-pyrido[3,4-b]indole-1,4-dione;

(6R,12aR)-2,3,6,7,12,12a-hexahydro-6-(3-chloro-4-methoxyphenyl)-2-methyl-pyrazino[2',1';6,1]pyrido[3, 4-b]indole-1,4-dione;

(6R,12aR)-2,3,6,7,12,12a-hexahydro-2-methyl-6-(3,4-methylenedioxyphenyl)-pyrazino[2',1';6,1]pyrido[3,4-b]indole-1,4-dione;

(6R,12aR)-2,3,6,7,12,12a-hexahydro-6-(3,4-methylenedioxyphenyl)-pyrazino[2',1';6,1]pyrido[3,4-b]indole-1,4-dione;

(5aR, 12R, 14aS)-1,2,3,5,6,11,12,14a-octahydro-12-(3,4-methylenedioxyphenyl)-pyrrolo[1",2":4'5']-pyrazino[2',1';6,1]pyrido[3,4-b]indole-5–1,4-dione;

(6R,12aR)-2,3,6,7,12,12a-hexahydro-6-(5-benzofuranyl)-2-methyl-pyrazino[2',1';6,1]pyrido[3,4-b]indole-1,4-dione;

(6R,12aR)-2,3,6,7,12,12a-hexahydro-6-(5-benzofuranyl)-pyrazino[2',1';6,1]pyrido[3,4-b]indole-1,4-dione;

(3S, 6R, 12aR)-2,3,6,7,12,12a-hexahydro-6-(5-benzofuranyl)-3-methyl-pyrazino[2',1';6,1]pyrido[3,4-b]indole-1,4-dione;

(3S, 6R, 12aR)-2,3,6,7,12,12a-hexahydro-6-(5-benzofuranyl)-2,3-dimethyl-pyrazino[2',1';6,1]pyrido[3,4-b]indole-1,4-dione;

(6R, 12aR)-2,3,6,7,12,12a-hexahydro-6-(5-benzofuranyl)-2-isopropyl-pyrazino[2',1';6,1]pyrido[3,4 -b]indole-1,4-dione; and physiologically acceptable solvates (e.g., hydrates) thereof.

Specific compounds of the invention are:

(6R,12aR)-2,3,6,7,12,12a-hexahydro-2-methyl-6-(3,4-methylenedioxyphenyl)-pyrazino[2',1';6,1]pyrido[3,4-b]indole-1,4-dione; and (6R,12aR)-2,3,6,7,12,12a-hexahydro-6-(5-benzofuranyl)-2-methyl-pyrazino[2',1';6,1]pyrido[3,4-b]indole -1,4-dione; and physiologically acceptable solvates (e.g., hydrates) thereof.

DETAILED DESCRIPTION OF THE PREFERRED EMBODIMENTS

It has been shown that compounds of the present invention are potent and selective inhibitors of cGMP-specific PDEs 1, 5, and 6, and particularly PDE5. Thus, compounds of formula (I) are of interest for use in therapy, specifically for the treatment of a variety of conditions where selective inhibition of PDE5 is considered to be beneficial.

In summary, the biochemical, physiological, and clinical effects of PDE5 inhibitors suggest their utility in a variety of disease states in which modulation of smooth muscle, renal, hemostatic, inflammatory, and/or endocrine function is desirable. The compounds of formula (I), therefore, have utility in the treatment of a number of disorders, including stable, unstable, and variant (Prinzmetal) angina, hypertension, pulmonary hypertension, congestive heart failure, acute respiratory distress syndrome, acute and chronic renal failure, atherosclerosis, conditions of reduced blood vessel patency (e.g., postpercutaneous transluminal coronary or carotid angioplasty, or post-bypass surgery graft stenosis), peripheral vascular disease, vascular disorders, such as Raynaud's disease, thrombocythemia, inflammatory diseases, stroke, bronchitis, chronic asthma, allergic asthma, allergic rhinitis, glaucoma, osteoporosis, preterm labor, benign prostatic hypertrophy, male and female erectile dysfunction, and diseases characterized by disorders of gut motility (e.g., irritable bowel syndrome).

An especially important use is the treatment of male erectile dysfunction, which is one form of impotence and is a common medical problem. Impotence can be defined as a lack of power, in the male, to copulate and can involve an inability to achieve penile erection or ejaculation, or both. The incidence of erectile dysfunction increases with age, with about 50% of men over the age of 40 suffering from some degree of erectile dysfunction.

Many compounds have been investigated for their therapeutic potential in the treatment of MED, including phenoxybenzamine, papaverine, prostaglandin E1 (PGE1), and phentolamine. These compounds, either alone or in combination, are typically self-administered by intracavernosal (i.c.) injection. While such treatments are effective, a treatment that is less invasive than injection therapy is preferred because pain, priapism, and fibrosis of the penis are associated with the i.c. administration of these agents.

For example, alprostadil (i.e., prostaglandin E1) delivered by intraurethral deposition has been approved for the treatment of MED. However, clinical studies showed that this route of administration is not effective in all patients. In addition, phentolamine and apomorphine are being evaluated as oral and sublingual therapies for MED, but neither compound has demonstrated efficacy across a broad range of subjects. Potassium channel openers (KCO) and vasoactive intestinal polypeptide (VIP) also have been shown to be active i.c., but cost and stability issues could limit development of the latter. An alternative to the i.c. route is the use of glyceryl trinitrate (GTN) patches applied to the penis, which has been shown to be effective but produces side effects in both patient and partner.

As an alternative to pharmacological treatment, a variety of penile prostheses have been used to assist achievement of an erection. The short-term success rate is good, but problems with infection and ischemia, especially in diabetic men, make this type of treatment a final option rather than a first-line therapy.

Because of the disadvantages of prior treatments for MED, new strategies to improve erectile response that exploit different physiological mechanisms are being investigated. One area of investigation is increasing the intracellular concentration of cGMP by providing a new type of oral therapy for the treatment of MED.

Increasing cGMP concentration is an important step in the physiology of penile erections. A penile erection is caused by neural stimuli that ultimately cause vasodilation of the arteries and sinusoidal spaces of the corpus cavernosum. Research indicates that nitric oxide plays a central role in this vasodilation.

In particular, atrial natriuretic peptides (ANP) and nitric oxide (NO, sometimes referred to as endothelium-derived relaxing factor or EDRF) relax smooth muscle by increasing guanylyl cyclase activity, which raises intracellular cGMP concentration. Intracellular cGMP is hydrolyzed by phosphodiesterases (PDEs), thereby terminating the action of the cyclic nucleotide. PDE5 is the major cGMP hydrolyzing enzyme in vascular smooth muscle. Accordingly, PDE5 inhibition potentiates the relaxant effects of ANP and nitric oxide by increasing the cGMP levels. Therefore, a compound that inhibits the PDE5 enzyme (and thereby indirectly inhibits the hydrolysis of cGMP) should potentiate the vascular response to nitric oxide, thereby facilitating the achievement and maintenance of erection.

PDE5 inhibitors have potential for use in treating male erectile dysfunction (MED), hypertension, heart failure, and other disease states because of their ability to facilitate the action of ANP and NO. For example, sildenafil, a PDE inhibitor showing little selectivity with respect to PDE6, has the structure:

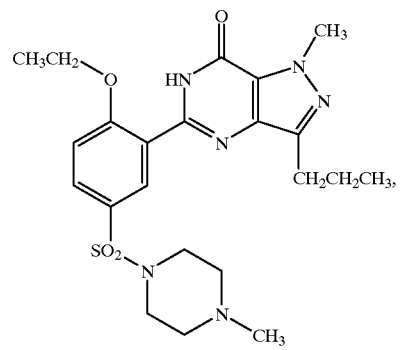

and has shown efficacy in oral administration clinical trials for MED, which supports the hypothesis that augmenting normal or subnormal guanylyl cyclase stimuli has therapeutic benefits.

It is envisioned, therefore, that compounds of formula (I) are useful in the treatment of erectile dysfunction. Furthermore, the compounds can be administered orally, thereby obviating the disadvantages associated with intracavernosal administration. Thus, the present invention concerns the use of compounds of formula (I), or a pharmaceutically acceptable salt thereof, or a pharmaceutical composition containing either entity, for the manufacture of a medicament for the curative or prophylactic treatment of erectile dysfunction in a male animal, including man.

It also has been observed that human corpus cavernosum contains three distinct PDE enzymes (see A. Taher et al., *J. Urol.*, 149, p. 285A (1993)), one of which is the cGMP-specific PDE5. As a consequence of the selective PDE5 inhibition exhibited by compounds of the present invention, the present compounds sustain cGMP levels, which in turn mediate relaxation of the corpus cavernosum tissue and consequent penile erection.

Although the compounds of the invention are envisioned primarily for the treatment of erectile dysfunction in humans, such as male erectile dysfunction and female sexual dysfunction, including orgasmic dysfunction related to clitoral disturbances, they also can be used for the treatment of premature labor and dysmenorrhea.

It is understood that references herein to treatment extend to prophylaxis, as well as treatment of established conditions.

It also is understood that "a compound of formula (I)," or a physiologically acceptable salt or solvate thereof, can be administered as the neat compound, or as a pharmaceutical composition containing either entity.

A further aspect of the present invention is providing a compound of formula (I) for use in the treatment of stable, unstable, and variant (Prinzmetal) angina, hypertension, pulmonary hypertension, chronic obstructive pulmonary disease, congestive heart failure, acute respiratory distress syndrome, acute and chronic renal failure, atherosclerosis, conditions of reduced blood vessel patency (e.g., post-PTCA or post-bypass graft stenosis), peripheral vascular disease, vascular disorders such as Raynaud's disease, thrombocythemia, inflammatory diseases, prophylaxis of myocardial infarction, prophylaxis of stroke, stroke, bronchitis, chronic asthma, allergic asthma, allergic rhinitis, glaucoma, osteoporosis, preterm labor, benign prostatic hypertrophy, male and female erectile dysfunction, or diseases characterized by disorders of gut motility (e.g., IBS).

According to another aspect of the present invention, there is provided the use of a compound of formula (I) for the manufacture of a medicament for the treatment of the above-noted conditions and disorders.

In a further aspect, the present invention provides a method of treating the above-noted conditions and disorders in a human or nonhuman animal body which comprises administering to said body a therapeutically effective amount of a compound of formula (I).

Compounds of the invention can be administered by any suitable route, for example by oral, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or using a high pressure technique, like POWDER-JECT™. Oral administration generally is preferred.

With respect to treating sexual dysfunction and particularly erectile dysfunction in humans, oral administration of the compounds of the invention is the preferred route. Oral administration is the most convenient and avoids the disadvantages associated with intracavernosal administration. For patients suffering from a swallowing disorder or from impairment of drug absorption after oral administration, the drug can be administered parenterally, e.g., sublingually or buccally.

For administration to man in the curative or prophylactic treatment of the conditions and disorders identified above, oral dosages of a compound of formula (I) generally are about 0.5 to about 1000 mg daily for an average adult patient (70 kg). Thus, for a typical adult patient, individual tablets or capsules contain 0.2 to 500 mg of active compound, in a suitable pharmaceutically acceptable vehicle or carrier, for administration in single or multiple doses, once or several times per day. Dosages for intravenous, buccal, or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of this invention.

For human use, a compound of the formula (I) can be administered alone, but generally is administered in admixture with a pharmaceutical carrier selected with regard to the intended route of administration and standard pharmaceutical practice. For example, the compound can be administered orally, buccally, or sublingually in the form of tablets containing excipients such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents (e.g., methylcellulose, a semisynthetic glyceride such as witepsol, or mixtures of glycerides such as a mixture of apricot kernel oil and PEG-6 esters, or mixtures of PEG-8 and caprylic/capric glycerides). A compound also can be injected parenterally, for example, intravenously, intramuscularly, subcutaneously, or intracoronarily. For parenteral administration, the compound is best used in the form of a sterile aqueous solution which can contain other substances, for example, salts, or monosaccharides, such as mannitol or glucose, to make the solution isotonic with blood.

For veterinary use, a compound of formula (I) or a nontoxic salt thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (I), together with a pharmaceutically acceptable diluent or carrier therefor.

There is further provided by the present invention a process of preparing a pharmaceutical composition comprising a compound of formula (I), which process comprises mixing a compound of formula (I), together with a pharmaceutically acceptable diluent or carrier therefor.

In a particular embodiment, the invention includes a pharmaceutical composition for the curative or prophylactic treatment of erectile dysfunction in a male animal, including man, comprising a compound of formula (I) or a pharmaceutically acceptable salt thereof, together with a pharmaceutically acceptable diluent or carrier.

A compound of formula (I) also can be used in combination with other therapeutic agents which can be useful in the treatment of the above-mentioned and other disease states. The invention thus provides, in another aspect, a combination of a compound of formula (I), together with a second therapeutically active agent.

A compound of formula (I) can be used in the preparation of a medicament for co-administration with the second therapeutically active agent in treatment of conditions where inhibition of a cGMP-specific PDE is beneficial. In addition, a compound of formula (I) can be used in the preparation of a medicament for use as adjunctive therapy with a second therapeutically active compound to treat such conditions. Appropriate doses of known second therapeutic agents for use in combination with a compound of formula (I) are readily appreciated by those skilled in the art.

In particular, because compounds of the present invention maintain cGMP levels, the compounds of formula (I) can provide beneficial antiplatelet, antineutrophil, antivasospastic, vasodilatory, natriuretic, and diuretic activities, as well as potentiate the effects of endothelium-derived relaxing factor (EDRF), gastric NO administration, nitrovasodilators, atrial natriuretic factor (ANF), brain natriuretic peptide (BNP), C-type natriuretic peptide (CNP), and endothelium-dependent relaxing agents such as bradykinin, acetylcholine, and 5-HT$_1$.

The present selective PDE5 inhibitors in combination with vasodilators, including nitric oxide and nitric oxide donators and precursors, such as the organic nitrate vasodilators which act by releasing nitric oxide in vivo, are especially useful in treatment of angina, congestive heart failure, and malignant hypertension (e.g., pheochromocytoma). Related to the capacity of the present PDE5 inhibitors to potentiate nitric oxide donors and precursors is their ability, in spontaneously hypertensive rats, to reverse the desensitization to these agents that occurs with chronic use.

Examples of vasodilators that can be used in conjunction with the compounds of formula (I) include, but are not limited to, (a) organic nitrates, such as nitroglycerin, isosorbide dinitrate, pentaerythrityl tetranitrate, isosorbide-5-mononitrate, propatyl nitrate, trolnitrate, nicroandil, mannitol hexanitrate, inositol hexanitrate, N-[3-nitratopivaloyl]-L-cysteine ethyl ester, (b) organic nitrites, like isoamyl nitrite, (c) thionitrites, (d) thionitrates, (e) S-nitrosothiols, like S-nitroso-N-acetyl-D,L-penicillamine, (f)

nitrosoproteins, (g) substituted furoxanes, such as 1,2, 5oxadiazole-2-oxide and furazan-N-oxide, (h) substituted sydnonimines, such as molsidomine and mesocarb, (i) nitrosyl complex compounds, like iron nitrosyl compounds, especially sodium nitroprusside, and (j) nitric oxide (NO) itself.

Other classes of therapeutic agents that can be used in conjunction with the compounds of formula (I), in addition to vasodilators, include, but are not limited to, α-adrenergic blockers, mixed α,β-blockers, prostaglandin EI (PGEI) and prostacyclin (PGI2), angiotensin converting enzyme inhibitors (ACE inhibitors), neutral endopeptidase (NEP) inhibitors, centrally acting dopaminergic agents (such as apomorphine), vasoactive intestinal peptides (VIP), calcium channel blockers, and compounds like thiazides.

Alpha-adrenergic blockers inhibit vasoconstriction in the corpus cavernosum. Because PDE5 inhibitors enhance vasodilation of the same smooth muscle tissue, a PDE5 inhibitor of formula (I) and an α-adrenergic blocker, like phentolamine or prazocin, or a centrally acting dopaminergic agent, like apomorphine, can be expected to potentiate one another in a treatment for MED or other disorders. Potentiation of mixed α,β-blockers, like carvedilol, which is employed in treatment of hypertension, also is expected Similarly, α$_2$-adrenergic blockers, like yohimbine, can be potentiated.

Prostaglandin E1 enhances relaxation of the corpus cavernosum by increasing the formation of cyclic AMP. Cyclic AMP can be degraded in the corpus cavernosum by PDE3, which is inhibited by cyclic GMP. By maintaining cyclic GMP levels, a PDE5 inhibitor can indirectly inhibit PDE3 activity, and hence block degradation of cyclic AMP. Therefore, a PDE5 inhibitor of formula (I) can be expected to potentiate the activity of PGE1 in the treatment of MED or compounds having similar activities, such as PGI2, in the treatment of pulmonary hypertension, for example.

Angiotensin converting enzyme (ACE) inhibitors block the conversion of angiotensin I into angiotensin II, which causes systemic vasoconstriction and the retention of sodium and water. PDE5 inhibitors cause vasodilation in hypertensive animals, and stimulate the excretion of sodium and water in normotensive animals. Therefore, a PDE5 inhibitor of formula (I) can be combined with an ACE inhibitor to achieve more powerful vasodilatory and natriuretic effects in, for example, treatment of congestive heart failure or hypertensive states.

Neutral endopeptidase (NEP) inhibitors inhibit the degradation of atrial natriuretic peptide (ANP) by NEP. PDE5 inhibitors can be expected to potentiate the action of ANP by inhibiting degradation of its second messenger, cyclic GMP, and, therefore, a compound of formula (I) can potentiate the effects of agents, like NEP inhibitors, that increase blood levels of ANP.

The combination referred to above can be presented for use in the form of a single pharmaceutical formulation, and, thus, pharmaceutical compositions comprising a combination as defined above together with a pharmaceutically acceptable diluent or carrier comprise a further aspect of the invention.

The individual components of such a combination, therefore, can be administered either sequentially or simultaneously from the same or separate pharmaceutical formulations. As is the case for the PDE5 inhibitors of formula (I), a second therapeutic agent can be administered by any suitable route, for example, by oral, buccal, inhalation, sublingual, rectal, vaginal, transurethral, nasal, topical, percutaneous (i.e., transdermal), or parenteral (including intravenous, intramuscular, subcutaneous, and intracoronary) administration.

In some embodiments, the compound of formula (I) and the second therapeutic agent are administered by the same route, either from the same or from different pharmaceutical compositions. However, in other embodiments, using the same route of administration for the compound of formula (I) and the second therapeutic agent either is impossible or is not preferred. For example, if the second therapeutic agent is nitric oxide, which typically is administered by inhalation, the compound of formula (I) must be administered by a different route. Furthermore, if a compound of formula (I) is used in combination with a nitrate vasodilator, for example, in treatment of an erectile dysfunction, it is preferred that the compound of formula (I) is administered orally and the vasodilator is administered topically, and preferably in a manner which avoids substantial systemic delivery of the nitrate.

The combination of a compound of formula (I) and a second therapeutic agent is envisioned in the treatment of several disease states. Examples of such treatments are the systemic and topical treatment of male and female sexual dysfunction, wherein a compound of formula (I) is used in combination with phentolamine, prazocin, apomorphine, PDE1, or a vasoactive intestinal peptide. The compound of formula (I) can be administered orally or transuretherally, and the second therapeutic agent can be administered orally, topically, or intracavernosally, for example. Persons skilled in the art are aware of the best modes of administration for each therapeutic agent, either alone or in a combination.

Other disease states that can be treated by a combination of a compound of formula (I) and a second therapeutic agent include, but are not limited to:

(a) treatment of hypertension using a compound of formula (I) in combination with an α-adrenergic blocker, a mixed α,β-blocker, like carvedilol, a thiazide, sodium nitroprusside, an ACE inhibitor, or a calcium channel blocker;

(b) treatment of pulmonary hypertension using a compound of formula (I) in combination with inhaled NO on other inhaled vasodilators, or with PGI2 administered via an IV pump; and (c) treatment of chronic obstructive pulmonary disease using a compound of formula (I) in combination with inhaled NO.

Examples of individual compounds of the invention for use in the treatment of erectile dysfunction include:

cis-2,3,6,7,12,12a-hexahydro-2-(4-pyridylmethyl)-6-(3,4-methylenedioxyphenyl)-pyrazino[2',1';6,1]-pyrido[3,4-b]indole-1,4-dione;

cis-2,3,6,7,12,12a-hexahydro-6-(2,3-dihydrobenzo[b]furan-5-yl)-2-methyl-pyrazino[2',1';6,1]-pyrido[3,4-b]indole-1,4-dione;

cis-2,3,6,7,12,12a-hexahydro-6-(5-bromo-2thienyl)-2-methyl-pyrazino[2',1';6,1]pyrido[3,4-b]indole-1,4-dione;

cis-2,3,6,7,12,12a-hexahydro-2-butyl-(4-methylphenyl)-pyrazino[2',1';6,1]pyrido[3,4-b]indole-1,4-dione;

(6R,12aR)-2,3,6,7,12,12a-hexahydro-2-isopropyl-6-(3,4-methylenedioxyphenyl)-pyrazino[2',1';6,1]pyrido-[3,4-b]indole-1,4-dione;

(6R,12aR)-2,3,6,7,12,12a-hexahydro-2-cyclopentyl-6-(3,4-methylenedioxyphenyl)-pyrazino[2',1';6,1]pyrido-[3,4-b]indole-1,4-dione;

(6R,12aR)-2,3,6,7,12,12a-hexahydro-2-cyclopropylmethyl-6-(4-methoxyphenyl)-pyrazino[2',1';6,1]pyrido[3,4-b]indole-1,4-dione;

(6R,12aR)-2,3,6,7,12,12a-hexahydro-6-(3-chloro-4-methoxyphenyl)-2-methyl-pyrazino[2',1';6,1]pyrido[3,4-b]indole-1,4-dione;

(6R,12aR)-2,3,6,7,12,12a-hexahydro-2-methyl-6-(3,4-methylenedioxyphenyl)-pyrazino[2',1';6,1]pyrido[3,4-b]indole-1,4-dione;

(6R,12aR)-2,3,6,7,12,12a-hexahydro-6-(3,4-methylenedioxyphenyl)-pyrazino[2',1';6,1]pyrido[3,4-b]indole-1,4-dione;

(5aR, 12R, $^{14}$aS)-1,2,3,5,6,11,12,14a-octahydro-12-($^{3}$,$^{4}$-methylenedioxyphenyl)-pyrrolo[1",2":4',5']-pyrazino[2',1',;6,1]pyrido[3,4-b]indole-5–1,4-dione;

cis-2,3,6,7,12,12a-hexahydro-2-cyclopropyl-6-(3,4-methylenedioxyphenyl)-pyrazino[2',1';6,1]pyrido[3,4-b]indole-1,4-dione;

(3S, 6R, 1$^{2}$aR)-2,3,6,7,12,12a-hexahydro-3-methyl-6-(3,4-methylenedioxyphenyl)-pyrazino[2',1';6,1]-pyrido[3,4-b]indole-1,4-dione; and physiologically acceptable salts and solvates (e.g., hydrates) thereof.

Especially useful specific compounds of the invention are:

(6R,12aR)-2,3,6,7,12,12a-hexahydro-2-methyl-6-(3,4-methylenedioxyphenyl)-pyrazino[2',1';6,1]pyrido[3,4-b]indole-1,4-dione; and (3S, 6R, 12aR)-2,3,6,7,12,12a-hexahydro-2,3-dimethyl-6-(3,4-methylenedioxyphenyl)-pyrazino-[2',1';6,1]pyrido[3,4-b]indole-1,4-dione; and physiologically acceptable salts and solvates (e.g., hydrates) thereof.

Compounds of formula (I) can be prepared by any suitable method known in the art or by the following processes which form part of the present invention. In the methods below, $R^0$, $R^1$, and $R^2$ are as defined in formula (I) above unless otherwise indicated.

Thus, a process (A) for preparing a compound of formula (I) wherein $R^3$ represents hydrogen comprises treating a compound of formula (II)

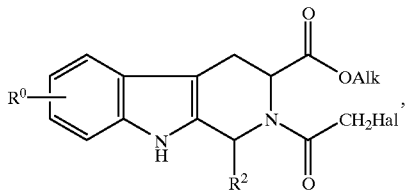

(II)

in which Alk represents $C_{1-6}$alkyl, e.g., methyl or ethyl, and Hal is a halogen atom, e.g., chlorine, with a primary amine $R^1NH_2$ in a suitable solvent, such as an alcohol (e.g., methanol or ethanol) or a mixture of solvents, conveniently at a temperature of from 20° C. to reflux (e.g., at about 50° C.).

A compound of formula (II) can be conveniently prepared by treating a compound of formula (III)

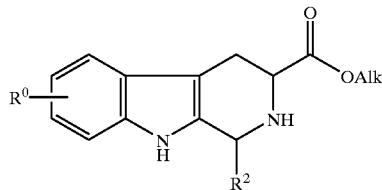

(III)

with a haloacetyl halide (e.g., chloroacetyl chloride) in a suitable solvent, such as a halogenated hydrocarbon (e.g., trichloromethane or dichloromethane) or an ether (e.g., tetrahydrofuran), preferably in the presence of a base such as an organic amine (e.g., a trialkylamine such as triethylamine) or an alkali metal carbonate or bicarbonate (e.g., NaHCO$_3$). The reaction conveniently can be effected at a temperature of from –20° C. to +20° C. (e.g., at about 0° C.).

A compound of formula (I) also can be prepared from a compound of formula (III) in a two-step procedure via a compound of formula (II) isolated without purification.

Compounds of formula (I) can be prepared as individual enantiomers in two steps from the appropriate enantiomer of formula (III) or as mixtures (e.g., racemates) of either pairs of cis or trans isomers from the corresponding mixtures of either pairs of cis or trans isomers of formula (III).

Individual enantiomers of the compounds of the invention can be prepared from racemates by resolution using methods known in the art for the separation of racemic mixtures into their constituent enantiomers, for examples, using HPLC (high performance liquid chromatography) on a chiral column such as Hypersil naphthylurea.

A compound of formula (III) conveniently can be prepared from a tryptophan alkyl ester of formula (IV)

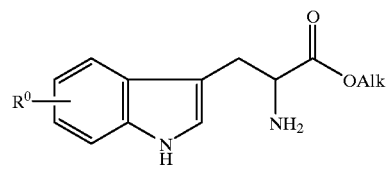

(IV)

(where Alk is as previously defined) or a salt thereof (e.g., the hydrochloride salt) according to either of the following procedures (a) and (b). Procedure (b) is only suitable for preparing cis isomers of formula (III) and can be particularly suitable for preparing individual cis enantiomers of formula (III) from D- or L-tryptophan alkyl esters as appropriate.

Procedure (a)

This comprises a Pictet-Spengler cyclization between a compound of formula (IV) and an aldehyde $R^2$CHO. The reaction can be conveniently effected in a suitable solvent such as a halogenated hydrocarbon (e.g., dichloromethane) or an aromatic hydrocarbon (e.g., toluene) in the presence of an acid, such as trifluoroacetic acid. The reaction conveniently can be carried out at a temperature of from –20° C. to reflux to provide a compound of formula (III) in one step. The reaction also can be carried out in a solvent such as an aromatic hydrocarbon (e.g., benzene or toluene) under reflux, optionally using a Dean-Stark apparatus to trap the water produced.

The reaction provides a mixture of cis and trans isomers which can be either individual enantiomers or racemates of pairs of cis or trans isomers, depending upon whether racemic or enantiomerically pure tryptophan alkyl ester was used as the starting material. Individual cis or trans enantiomers conveniently can be separated from mixtures thereof by fractional crystallization or by chromatography (e.g., flash column chromatography) using appropriate solvents and eluents. Similarly, pairs of cis and trans isomers can be separated by chromatography (e.g., flash column chromatography) using appropriate eluents. An optically pure trans isomer also can be converted to an optically pure cis isomer using suitable epimerization procedures. One such procedure comprises treating the trans isomer or a mixture (e.g., 1:1 mixture) of cis and trans isomers with methanolic or aqueous hydrogen chloride at a temperature of from 0° C. to the refluxing temperature of the solution. The mixture then can be subjected to chromatography (e.g., flash column chromatography) to separate the resulting diastereoisomers, or in the procedure utilizing aqueous hydrogen chloride, the desired cis isomer precipitates out as the hydrochloride salt which then can be isolated by filtration.

Procedure (b)

This comprises a four-step procedure from a compound of formula (IV) or a salt thereof (e.g., the hydrochloride salt). The procedure is particularly suitable for preparing a 1R, 3R isomer of formula (III) from a D-tryptophan alkyl ester of formula (IV) or a salt thereof (e.g., the hydrochloride salt). Thus, a first step (i) comprises treating a compound of formula (IV) with an acid halide R²COHal (where Hal is as previously defined) in the presence of a base, e.g., an organic base such as a trialkylamine (for example, triethylamine), to provide a compound of formula (V).

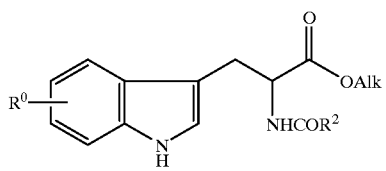

(V)

The reaction can be conveniently carried out in a suitable solvent, such as a halogenated hydrocarbon (e.g., dichloromethane) or an ether (e.g., tetrahydrofuran), and at a temperature of from −20° C. to +40° C.

Step (ii) comprises treating a compound of formula (V) with an agent to convert the amide group to a thioamide group. Suitable sulfurating agents are well known in the art. Thus, for example, the reaction can be conveniently effected by treating (V) with Lawesson's reagent. This reaction can be conveniently carried out in a suitable solvent, such as ether (e.g., dimethoxyethane) or an aromatic hydrocarbon (e.g., toluene), at an elevated temperature, such as from 40° C. to 80° C. to provide a compound of formula (VI)

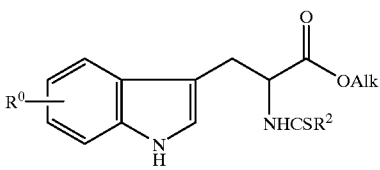

(VI)

Step (iii) comprises treating a compound of formula (VI) with a suitable agent to provide a compound of formula (VII)

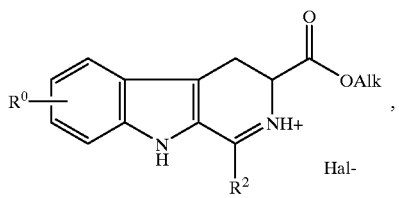

(VII)

wherein Hal is a halogen atom, e.g., iodine. The reaction can be conveniently effected by treating (VI) with an alkylating agent, such as a methyl halide (e.g., methyl iodide), or an acylating agent, such as an acetyl halide (e.g., acetyl chloride), in a suitable solvent, such as a halogenated hydrocarbon (e.g., dichloromethane) at an elevated temperature (e.g., under reflux).

In step (iv), the resulting iminium halide of formula (VII) can be treated with a reducing agent, such as a boron hydride, e.g., sodium borohydride, to provide the desired compound of formula (III). The reduction can be conveniently effected at a low temperature, e.g., within the range of −100° C. to 0° C., in a suitable solvent, such as an alcohol (e.g., methanol).

There is further provided by the present invention a process (B) for preparing a compound of formula (I), wherein $R^1$ and $R^3$ together represent a 3- or 4-membered alkyl or alkenyl chain, which process (B) comprises cyclization of a compound of formula (VIII)

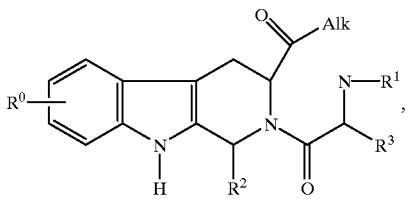

(VIII)

wherein Alk represents $C_{1-6}$alkyl and $R^1$ and $R^3$ together represent a 3- or 4-membered chain, both as hereinbefore described. The cyclization is suitably carried out in an organic solvent or solvents, such as an alcoholic solvent (e.g., methanol), and optionally an ether solvent such as tetrahydrofuran, and in the presence of a reducing agent, aptly a palladium catalyst, such as palladium on carbon.

Conveniently, a compound of formula (VIII) is prepared by reaction of a compound of formula (III) as hereinbefore described with a compound of formula (IX)

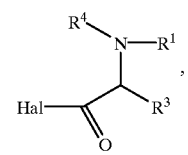

(IX)

wherein Hal represents a halogen atom as hereinbefore described, $R^1$ and $R^3$ together represent a 3- or 4-membered chain as hereinbefore described, and $R^4$ represents a protecting group, suitably a benzyloxycarbonyl group or the like. Typically, the reaction is carried out in a chlorinated organic solvent, such as dichloromethane, and a tertiary amine, such as triethylamine or the like.

According to a further aspect of the present invention, there is provided a process (C) for preparing a compound of formula (I) wherein $R^3$ represents $C_{1-3}$alkyl, which process comprises cyclization of a compound of formula (X)

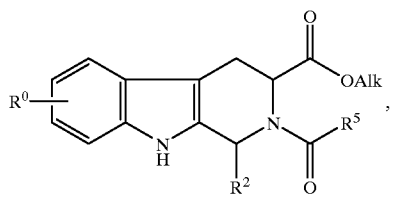

wherein Alk represents $C_{1-6}$alkyl as hereinbefore described and $R^5$ represents $C_{2-5}$alkyl, substituted at $C_1$ by a halogen atom, the halogen atom being as hereinbefore described. Suitably, the cyclization is achieved by reflux for many hours, such as 22 to 26 hours, in the presence of an ether solvent, such as tetrahydrofuran, and a suitable amine as hereinafter described in the accompanying examples.

Aptly, a compound of formula (X) can be prepared from a compound of formula (III) by suitable acylation techniques, such as reaction with a $C_{3-6}$carboxylic acid, substituted at C-2 by a halogen atom in a halogenated organic solvent, such as dichloromethane.

Compounds of formula (I) can be converted to other compounds of formula (I). Thus, for example, when $R^2$ is a substituted benzene ring, it may be necessary or desirable to prepare the suitably substituted compound of formula (I) subsequent to process (A), (B), or (C), as above. Examples of appropriate interconversions include nitro to amino or aralkyloxy to hydroxy by suitable reducing means (e.g., using a reducing agent such as $SnCl_2$ or a palladium catalyst, such as palladium-on-carbon), or amino to substituted amino, such as acylamino or sulphonylamino using standard acylating or sulphonylating conditions. In the case where $R^2$ represents a substituted bicyclic system, suitable interconversion can involve removal of a substituent, such as by treatment with a palladium catalyst (e.g., palladium-on-carbon) whereby, for example, a benzyl substituent can be removed from a suitable bicyclic system.

The pharmaceutically acceptable acid addition salts of the compounds of formula (I), which contain a basic center, can be treated with a suitable acid, either neat or in a suitable solution, and the resulting salt isolated either by filtration or by evaporation under vacuum of the reaction solvent. Pharmaceutically acceptable base addition salts can be obtained in an analogous manner by treating a solution of a compound of formula (I) with a suitable base. Both types of salt can be formed or interconverted using ion-exchange resin techniques.

Compounds of the invention can be isolated in association with solvent molecules by crystallization from or evaporation of an appropriate solvent.

Thus, according to a further aspect of the invention, we provide a process for preparing a compound of formula (I) or a salt or solvate (e.g., hydrate) thereof which comprises process (A), (B), or (C) as hereinbefore described followed by
(i) an interconversion step, and/or either
(ii) salt formation, or
(iii) solvate (e.g., hydrate) formation.

There is further provided by the present invention compounds of formulae (II), (VIII), (X), and further compounds of formulae (III), (V), (VI), and (VII), with the exception for compounds (III), (V), (VI), and (VII), wherein $R^0$ is hydrogen, $R^2$ is phenyl, and Alk is methyl.

The pharmaceutically acceptable acid addition salts of the compounds of formula (I) which contain a basic center can be prepared in a conventional manner. For example, a solution of the free base can be treated with a suitable acid, either neat or in a suitable solution, and the resulting salt isolated either by filtration or by evaporation under vacuum of the reaction solvent. Pharmaceutically acceptable base addition salts can be obtained in an analogous manner by treating a solution of a compound of formula (I) with a suitable base. Both types of salt can be formed or interconverted using ion-exchange resin techniques.

Thus, according to a further aspect of the invention, a method for preparing a compound of formula (I) or a salt or solvate (e.g., hydrate) is provided, wherein the method comprises process (A), (B), or (C) as hereinbefore described, followed by (i) salt formation, or (ii) solvate (e.g., hydrate) formation. The following additional abbreviations are used hereafter in the accompanying examples: rt (room temperature), min (minute), g (gram), mmol (millimole), m.p. (melting point), eq (equivalents), mL (milliliter), μL (microliters), DMSO (dimethyl sulfoxide), $Na_2SO_4$ (sodium sulfate), $NaHCO_3$ (sodium bicarbonate), DCM or $CH_2Cl_2$ (dichloromethane), $CHCl_3$ (chloroform), $CDCl_3$ (deuterated chloroform), NaCl (sodium chloride), TFA (trifluoracetic acid), MeOH (methanol), EtOH (ethanol), DMF (dimethylformamide), EtOAc (ethyl acetate), and THF (tetrahydrofuran).

Intermediates 1 and 2
Methyl 1,2,3,4-tetrahydro-1-(3,4-methylenedioxyphenyl)-9H-pyrido[3,4-b]indole-3-carboxylate, cis and trans isomers To a stirred solution of racemic tryptophan methyl ester (13 g) and piperonal (9.7 g) in anhydrous $CH_2Cl_2$ (300 mL) cooled at 0° C. was added dropwise trifluoroacetic acid (9 mL) and the solution was allowed to react at ambient temperature. After 4 days, the yellow solution was diluted with $CH_2Cl_2$ (100 mL), washed with a saturated aqueous solution of $NaHCO_3$, then with water and dried over $Na_2SO_4$. The organic layer was evaporated to dryness under reduced pressure and the residue was purified by flash chromatography eluting with $CH_2Cl_2$/MeOH (99/1) to give first Intermediate 1, the cis isomer (6.5 g) m.p.: 90–93° C. followed by Intermediate 2, the trans isomer (6.4 g) m.p.: 170° C.

The following compounds were obtained in a similar manner:

Intermediates 3 and 4
Methyl 1,2,3,4-tetrahydro-1-(4-methoxyphenyl)-9H-pyrido[3,4-b]indole-3-carboxylate, cis and trans isomers The same method but starting from racemic tryptophan methyl ester and 4-methoxybenzaldehyde gave Intermediate 3, the cis isomer as white crystals m.p.: 142° C. and Intermediate 4, the trans isomer as white crystals m.p.: 209–210° C.

Intermediate 5
Methyl 1,2,3,4-tetrahydro-1-(3-methoxyphenyl)-9H-pyrido[3,4-b]indole-3-carboxylate, cis isomer The same method but starting from racemic tryptophan methyl ester and 3-methoxybenzaldehyde gave the title compound as white crystals m.p.: 146° C.

Intermediates 6 and 7
Methyl 1,2,3,4-tetrahydro-1-(4-ethoxyphenyl)-9H-pyridol[3,4-b]indole-3-carboxylate, cis and trans isomers The same method but starting from racemic tryptophan methyl ester and 4-ethoxybenzaldehyde gave Intermediate 6, the cis isomer as white crystals m.p.: 180° C., and Intermediate 7, the trans isomer as white crystals m.p.: 196–198° C.

Intermediates 8 and 9
Methyl 1,2,3,4-tetrahydro-1-(2,3-dihydrobenzo[b]furan-5-yl)-9H-pyrido[3,4-b]indole-3-carboxylate, cis and trans isomers The same method but starting from racemic tryptophan methyl ester and 2,3-dihydrobenzo[b]furan-5-carboxaldehyde gave Intermediate 8, the cis isomer as white crystals m.p.: 106–109° C., and Intermediate 9, the trans isomer as white crystals m.p.: 219–222° C.

Intermediates 10 and 11
Methyl 1,2,3,4-tetrahydro-1-(3,4-ethylenedioxyphenyl)-9H-pyrido[3,4-b]indole-3-carboxylate, cis and trans isomers The same method but starting from racemic tryptophan methyl ester and 1,4-benzodioxan-6-carboxaldehyde gave Intermediate 10, the cis isomer as white crystals m.p.: 104–106° C., and Intermediate 11, the trans isomer as white crystals m.p.: 207–209° C.

Intermediate 12
Methyl 1,2,3,4-tetrahydro-1-(2-chlorophenyl)-9H-pyrido[3,4-b]indole-3-carboxylate, mixture of cis and trans isomers The same method but starting from racemic tryptophan methyl ester and 2-chlorobenzaldehyde gave the title compound as white crystals m.p.: 154° C.

Intermediates 13 and 14
Methyl 1,2,3,4-tetrahydro-1-(4-chlorophenyl)-9H-pyrido[3,4-b]indole-3-carboxylate, cis and trans isomers The same method but starting from racemic tryptophan methyl ester and 4-chlorobenzaldehyde gave Intermediate 13, the cis isomer as white crystals m.p.: 208–209°c, and Intermediate 14, the trans isomer as white crystals m.p.: 108–109° C.

Intermediates 15 and 16
Methyl 1,2,3,4-tetrahydro-1-(3,4-dichlorophenyl)-9H-pyrido[3,4-b]indole-3-carboxylate, cis and trans isomers The same method but starting from racemic tryptophan methyl ester and 3,4-dichlorobenzaldehyde gave Intermediate 15, the cis isomer as a white solid $^1$H NMR (CDCl$_3$) δ (ppm): 7.8–7 (m, 8H, H aromatic); 5.15 (brs, 1H, H-1); 3.9–3.8 (dd, 1H, H-3) 3.7 (s, 3H, CO$_2$CH$_3$); 3.2–3.1 (ddd, 1H, H-4) 2.9 (m, 1H, H-4); 2.4 (brs, 1H, NH), and Intermediate 16, the trans isomer as a white solid m.p.: 204° C.

Intermediate 17
Methyl 1,2,3,4-tetrahydro-1-(1,2,3,4-tetrahydro-6-naphthyl)-9H-pyrido[3,4-b]indole-3-carboxylate, cis isomer The same method but starting from racemic tryptophan methyl ester and 1,2,3,4-tetrahydronaphthyl-6-carboxaldehyde gave the title compound as a white solid $^1$H NMR (CDCl$_3$) δ (ppm): 7.7–7(m, 8H, H aromatic); 5.2 (s, 1H, H-1); 4.0 (dd, 1H, H-3); 3.8 (s, 3H, CO$_2$CH$_3$); 3.2 (m, 1H, H-4); 3.0 (m, 1H, H-4); 2.7 (m, 4H, CH$_2$Ar); 1.7 (s, 4H, CH$_2$CH$_2$Ar).

Intermediates 18 and 19
Methyl 1,2,3,4-tetrahydro-1-(2-naphthyl)-9H-pyrido[3,4-b]indole-3-carboxylate, cis and trans isomers The same method but starting from racemic tryptophan methyl ester and 2-naphthaldehyde gave Intermediate 18, the cis isomer as a white solid $^1$H NMR (CDCl$_3$) δ (ppm): 8–6.9 (m, 12H, H aromatic); 5.4 (s, 1H, H-1); 3.95 (dd, 1H, H-3); 3.7 (s, 3H, CO$_2$CH$_3$) 3.2 (ddd, 1H, H-4); 3 (m, 1H, H-4); 2.5 (brs, 1H, NH), and Intermediate 19, the trans isomer as a white solid (0.6 g) m.p.: 119° C.

Intermediates 20 and 21
Methyl 1,2,3,4-tetrahydro-1-(2-thienyl)-9H-pyrido[3,4-b]indole-3-carboxylate, cis and trans isomers The same method but starting from racemic tryptophan methyl ester and 2-thiophenecarboxaldehyde gave Intermediate 20, the cis isomer as a pale yellow solid m.p.: 134–137° C., and Intermediate 21, the trans isomer as white crystals m.p.: 169° C.

Intermediates 22 and 23
Ethyl 1,2,3,4-tetrahydro-1-(3-thienyl)-9H-pyrido[3,4-b]indole-3-carboxylate, cis and trans isomers The same method but starting from racemic tryptophan ethyl ester and 3-thiophenecarboxaldehyde gave Intermediate 22, the cis isomer as white crystals m.p.: 130° C., and Intermediate 23, the trans isomer as white crystals m.p.: 182–184° C.

Intermediates 24 and 25
Methyl 1,2,3,4-tetrahydro-1-(5-bromo-2-thienyl)-9H-pyrido[3,4-b]indole-3-carboxylate, cis and trans isomers The same method but starting from racemic tryptophan methyl ester and 5-bromo-2-thiophenecarboxaldehyde gave Intermediate 24, the cis isomer as a cream solid m.p.: 130° C., and Intermediate 25, the trans isomer as a cream solid m.p.: 205° C.

Intermediates 26 and 27
Methyl 1,2,3,4-tetrahydro-1-(4-bromo-2-thienyl))-9H-pyrido[3,4-b]indole-3-carboxylate, cis and trans isomers The same method but starting from racemic tryptophan methyl ester and 4-bromo-2-thiophenecarboxaldehyde gave Intermediate 26, the cis isomer as a cream solid m.p.: 200° C., and Intermediate 27, the trans isomer as a cream solid m.p.: 120° C.

Intermediate 28
Methyl 1,2,3,4-tetrahydro-1-(3-furyl)-9H-pyrido-[3,4-b]indole-3-carboxylate, mixture of cis and trans isomers The same method but starting from racemic tryptophan methyl ester and 3-furaldehyde gave the title compound as a yellow solid m.p.: 130° C..

Intermediates 29 and 30
Ethyl 1,2,3,4-tetrahydro-1-(5-methyl-2-furyl)-9H-pyrido[3,4-b]indole-3-carboxylate, cis and trans isomers The same method but starting from racemic tryptophan ethyl ester and 5-methylfurfural gave Intermediate 29, the cis isomer as a oily compound $^1$H NMR (CDCl$^3$) δ (ppm): 7.7 (brs, 1H, NH indole); 7.5 (d, 1H, H aromatic); 7.25–6.9 (m, 3H, H aromatic); 6.15 (d, 1H, H aromatic); 5.85 (m, 1H, H aromatic); 5.25 (brs, 1H, H-1); 4.2 (q, 2H, CO$_2$CH$_2$CH$_3$); 3.8 (dd, 1H, H-3); 3.2–2.8 (m, 2H, H-4); 2.2 (s, 3H, CH$_3$); 1.25 (t, 3H, CQ$_2$CH$_2$CH$_3$), and Intermediate 30, the trans isomer as a cream solid m.p.: 152° C.

Intermediates 31 and 32
Ethyl 1,2,3,4-tetrahydro-1-(4-methylphenyl)-9H-pyrido[3,4-b]indole-3-carboxylate, cis and trans isomers The same method but starting from racemic tryptophan ethyl ester and p-tolualdehyde gave Intermediate 31, the cis isomer as white crystals m.p.: 148° C., and Intermediate 32, the trans isomer as white crystals m.p.: 180° C.

Intermediates 33 and 34
Methyl 1,2,3,4-tetrahydro-1-(3-methylphenyl)-9H-pyrido[3,4-b]indole-3-carboxylate, cis and trans isomers The same method but starting from racemic tryptophan methyl ester and m-tolualdehyde gave Intermediate 33, the cis isomer as white crystals $^1$H NMR (CDCl$_3$) δ (ppm): 7.6–7 (m, 9H, H aromatic); 5.2 (brs, 1H, H-l);
4–3.9 (dd, 1H, H-3) 3.8 (s, 3H, CO$_2$CH$_3$); 3.2–3.1 (ddd, 1H, H-4) 3 (m, 1H, H-4); 2.35 (s, 3H, CH$_3$); 1.7 (brs, 1H, NH), and Intermediate 34, the trans isomer as a white solid m.p.: 175° C.

Intermediates 35 and 36
Methyl 1,2,3,4-tetrahydro-1–14-trifluoromethylphenyl)-9H-pyrido[3,4-b]indole-3-carboxylate, cis and trans isomers The same method but starting from racemic tryptophan methyl ester and 4-trifluoromethylbenzaldehyde gave Intermediate 35, the cis isomer as pale yellow crystals m.p.: 190° C., and Intermediate 36, the trans isomer as pale yellow crystals m.p.: 203° C.

Intermediates 37 and 38
Ethyl 1,2,3,4-tetrahydro-1-(4-cyanophenyl)-9H-pyrido[3,4-b]indole-3-carboxylate, cis and trans isomers The same method but starting from racemic tryptophan ethyl ester and 4-cyanobenzaldehyde gave Intermediate 37, the cis isomer as white crystals m.p.: 200° C., and Intermediate 38, the trans isomer as white crystals m.p.: 156° C.

Intermediate 39

Methyl 1,2,3,4-tetrahydro-1-(4-hydroxyphenyl)-9H-pyrido[3 4-b]indole-3-carboxylate, cis isomer The same method but starting from racemic tryptophan ethyl ester and 4-hydroxybenzaldehyde gave the title compound as pale yellow crystals $^1$H NMR (DMSO) δ (ppm): 10.3 (s, 1H, NH-indole) 9.4 (s, 1H, OH); 7.8 7.5 (m, 8H, H aromatic); 5.1 (brs, 1H, H-1); 3.9 (m, 1H, H-3); 3.75 (s, 3H, $CO_2CH$,) 3.1 (m, 1H, H-4); 2.8 (m, 1H, H-4).

Intermediate 40

Methyl 1,2,3,4-tetrahydro-1-(3-hydroxy-4-methoxyphenyl) 9H-pyrido[3,4-b]indole-3-carboxylate, cis isomer The same method but starting from racemic tryptophan methyl ester and 3-hydroxy-4-methoxybenzaldehyde gave the title compound as a yellow solid m.p.: 140–148° C.

Intermediate 41

Methyl 1,2,3,4-tetrahydro-1-(4-hydroxy-3-methoxyphenyl)-9H-pyrido[3,4-b]indole-3-carboxylate, cis isomer The same method but starting from racemic tryptophan methyl ester and 4-hydroxy-3-methoxybenzaldehyde gave the title compound as a cream solid m.p.: 195° c.

Intermediate 42

Methyl 1,2,3,4-tetrahydro-1-(4-ethylphenyl)-9H-pyrido[3,4-b]indole-3-carboxylate, cis and trans isomers The same method but starting from racemic tryptophan methyl ester and 4-ethylbenzaldehyde gave the cis and trans isomer of the title compound.

Cis isomer: white solid $^1$H NMR ($CDCl_3$) δ (ppm): 7.65–7.1 (m, 9H, H aromatic); 5.25 (brs, 1H, H-1); 4(dd, 1H, H-3); 3.9 (s, 3H, $CO_2CH_3$); 3.4 (ddd, 1H, H-4); 3.1 (m, 1H, H-4) 2.7 (q, 2H, C$\underline{H}_2CH_3$) 1.4 (t, 3H, $CH_2C\underline{H}_3$).

Trans isomer: white solid m.p.: 187° C.

Intermediates 43 and 44

Methyl 1,2,3,4-tetrahydro-1-(4-isopropylphenyl)-9H-pyrido[3,4-b]indole-3-carboxylate, cis and trans isomers The same method but starting from racemic tryptophan ethyl ester and 4-isopropylbenzaldehyde gave Intermediate 43, the cis isomer as a white solid $^1$H NMR (DMSO) δ (ppm): 10.15 (s, 1H, NH indole); 7.3–6.7 (m, 8H, H aromatic); 5 (brs, 1H, H-1); 3.6 (m, 1H, H-3); 3.5 (s, 3H, $CO_2CH_3$); 2.95–2.5 (m, 3H, H-4+C$\underline{H}$—(Me)$_2$) 2.4 (brs, 1H, NH); 1 (d, 6H, 2x$CH_3$), and Intermediate 44, the trans isomer as a white solid m.p.: 189° C.

Intermediates 45 and 46

Ethyl 1.2,3,4-tetrahydro-1-(4-nitrochenyl)-9H-pyrido[3,4-b]indole-3-carboxylate, cis and trans isomers The same method but starting from racemic tryptophan ethyl ester and 4-nitrobenzaldehyde gave Intermediate 45, the cis isomer as yellow crystals m.p.: 168° C., and Intermediate 46, the trans isomer as yellow crystals m.p.: 195° C.

Intermediate 47

Ethyl 1,2,3,4-tetrahydro-1-(4-dimethylaminophenyl)-9H-pyrido[3,4-b]indole-3-carboxylate, mixture of cis and trans isomers The same method but starting from racemic tryptophan ethyl ester and 4-dimethylaminobenzaldehyde gave the title compound as white crystals m.p.: 170° C.

Intermediates 48 and 49

Ethyl 1,2,3,4-tetrahydro-1-(3-pyridyl)-9H-pyrido[3,4-b]indole-3-carboxylate, cis and trans isomers The same method but starting from racemic tryptophan ethyl ester and 3-pyridinecarboxaldehyde gave Intermediate 48, the cis isomer as pale yellow crystals m.p.: 230–232° C., and Intermediate 49, the trans isomer as white crystals m.p.: 210–214° C.

Intermediates 50 and 51

Methyl 1,2,3,4 tetrahydro-6-fluoro-1-(3,4-methylenedioxyphenyl)-9H-pyrido[3,4-b]indole-3-carboxylate, cis and trans isomers The same method but starting from racemic 5fluoro-tryptophan methyl ester and piperonal gave Intermediate 50, the cis isomer as a cream solid m.p.: 60° C., and Intermediate 51, the trans isomer as a cream solid m.p.: 213° C.

Intermediates 52 and 53

Methyl 1,2,3,4-tetrahydro-6-fluoro-1-(4-methoxyphenyl)-9H-pyrido[3,4-b]indole-3-carboxylate, cis and trans isomers The same method but starting from racemic 5-fluorotryptophan methyl ester and 4-methoxybenzaldehyde gave Intermediate 52, the cis isomer as a solid $^1$H NMR ($CDCl_3$) δ (ppm): 7.4–6.8 (m, 8H, H aromatic); 5.15 (brs, 1H, H-1); 3.9 (dd, 1H, H-3) 3.8 (s, 3H, $CO_2CH_3$); 3.2–2.9 (m, 2H, H-4), and Intermediate 53, the trans isomer as a solid m.p.: 197° C.

Intermediates 54 and 55

(1R,3R)-Methyl 1,2,3,4-tetrahydro-1-(3,4-methylenedioxyphenyl)-9H-pyrido[3,4-b]indole-3-carboxylate, cis isomer and (1S,3R)-methyl 1,2,3,4-tetrahydro-1-(3,4-methylenedioxyphenyl)-9H-pyrido[3,4-b]indole-3-carboxylate trans isomer To a stirred solution of D-tryptophan methyl ester (11 g) and piperonal (7.9 g) in anhydrous $CH_2Cl_2$ (400 mL) cooled at 0° C. was added dropwise trifluoroacetic acid (7.7 mL) and the solution was allowed to react at ambient temperature. After 4 days, the yellow solution was diluted with $CH_2Cl_2$ (200 mL) and washed with a saturated aqueous solution of $NaHCO_3$, then with water (3×200 mL) and dried over $Na_2SO_4$. The organic layer was evaporated under reduced pressure and the residue was purified by flash chromatography eluting with dichlormethane/ethyl acetate (97/3) to give first Intermediate 54, the cis isomer (6.5 g) m.p.: 154° C. followed by Intermediate 55, the trans isomer (8.4 g) m.p.: 188° C.

The following compounds were obtained in a similar manner:

Intermediate 56

(1S, 3S) Methyl-1,2,3,4-tetrahydro-1-(3,4-methylenedioxyphenyl)-9H-pyrido[3,4-b]indole-3-carboxylate, cis isomer and (1R, 3S) methyl-1,2,3.4-tetrahydro-1-(3,4-methylenedioxyphenyl)-9H-pyrido[3,4-b]indole-3-carboxylate, trans isomer The same method but starting from L-tryptophan methyl ester and piperonal gave the cis and trans isomers of the title compound.

Cis isomer: white crystals m.p.: 154° C.

Trans isomer: white crystals m.p.: 187–189° C.

Intermediates 57 and 58

(1R,3R)-Methyl 1,2,3,4-tetrahydro-1-(4-methoxyphenyl)-9H-pyrido[3,4-b]indole-3-carboxylate, cis isomer and (1S, 3R)-methyl 1,2,3,4-tetrahydro-1-(4-methoxyphenyl)-9H-pyrido[3,4-b]indole-3-carboxylate, trans isomer The same method but starting from D-tryptophan methyl ester and 4-methoxybenzaldehyde gave Intermediate 57, the cis isomer as white crystals m.p.: 124–125SC, and Intermediate 58, trans isomer as white crystals m.p.: 219–222° C.

Intermediates 59 and 60

(1R, 3R)-Methyl 1,2,3,4-tetrahydro-1-(3-chloro-4-methoxyphenyl)-9H-pyrido[3,4-b]indole-3-carboxylate, cis isomer and (1S, 3R)-methyl 1,2,3,4-tetrahydro-1-(3-chloro-4-methoxyphenyl)-9H-pyrido[3,4-b]indole-3-carboxylate, trans isomer The same method, but starting from D-tryptophan methyl ester and 3-chloro-4-methoxybenzaldehyde gave Intermediate 59, the cis isomer isolated as the hydrochloride salt as white crystals m.p.: 200° C., and Intermediate 60, the trans isomer as white crystals m.p.: 164° C.

Intermediates 61 and 62

(1R,3R)-Methyl 1,2,3,4-tetrahydro-1-(2,3-dihydrobenzo-[b]furan-5-yl)-9H-pyrido[3,4-b]indole-3-carboxylate, cis isomer and (1S,3R)-methyl 1,2,3,4-tetrahydro-1-(5-(2,3-dihydrobenzo-[b]furan))-9H-pyrido[3,4-b]indole-3-carboxylate, trans isomer The same method but starting from D-tryptophan methyl ester and 2,3-dihydrobenzo[b]furan-5-carboxaldehyde gave Intermediate 61, the cis isomer as white crystals m.p.: 282° C., and Intermediate 62, the trans isomer as white crystals m.p.: 204° C.

Intermediates 63 and 64

(1R,3R)-Methyl 1,2,3,4-tetrahydro-1-(5-indanyl)-9H-pyrido[3,4-b]indole-3-carboxylate cis isomer and (1S,3R)-methyl 1,2,3,4-tetrahydro-1-(5-indanyl)-9H-pyrido[3,4-b]indole-3-carboxylate trans isomer The same method but starting from D-tryptophan methyl ester and indan-5-carboxaldehyde gave Intermediate 63, the cis isomer as white crystals m.p.: 130–131° C., and Intermediate 64, the trans isomer as white crystals m.p.: 196° C.

Intermediate 65

Ethyl 1,2,3,4-tetrahydro-1-(4-trifluoromethoxyphenyl)-9H-pyrido[3,4-b]indole-3-carboxylate, cis and trans isomers The same method but starting from racemic tryptophan ethyl ester and 4-trifluoromethoxybenzaldehyde gave cis and trans isomers of the title compound.

Cis isomer: white crystals m.p.: 88° C.

Trans isomer: white crystals m.p.: 152° C.

Intermediate 66

Methyl 1,2,3,4-tetrahydro-1-(5-methyl-2-thienyl)-9H-pyrido [3,4-b]indole-3-carboxylate, cis and trans isomers The same method but starting from racemic tryptophan methyl ester and 5-methyl-2-thiophenecarboxaldehyde gave the cis and trans isomers of the title compound.

Cis isomer: oily compound $^1$H NMR (CDCl$_3$) δ (ppm): 8.4 (brs, 1H, NH-indole); 7.7–6.6 (m, 6H, H aromatic); 5.5 (brs, 1H, H-1); 3.9 (dd, 1H, H-3); 3.85 (s, 3H, CO$_2$CH$_3$); 3.3–2.9 (m, 2H, H-4); 2.5 (s, 3H, CH$_3$).

Trans isomer: white crystals m.p.: 194° C.

Intermediates 67 and 68

(1S,3R)-Methyl 1,2,3,4-tetrahydro-1-(3,4-methylenedioxyphenyl)-9H-pyrido[3,4-b]indole-3-carboxylate and (1R,3R)-methyl 1,2,3,4-tetrahydro-1-(3,4-methylenedioxyphenyl)-9H-pyrido[3,4-b]indole-3-carboxylate To a stirred solution of D-tryptophan methyl ester (obtained by treating the corresponding hydrochloride salt in water with saturated aqueous NaHCO$_3$ solution and extraction with CH$_2$Cl$_2$) (25.7 g) and piperonal (19.4 g) in anhydrous dichloromethane (700 ml) cooled to 0° C. was added dropwise trifluoroacetic acid (18.1 ml) and the solution was allowed to react at 4° C. After 5 days, the yellow solution was diluted with dichloromethane (500 ml). The organic layer was washed with a saturated aqueous solution of NaHCO$_3$, then with water (3×500 ml) until the pH was neutral and dried over Na$_2$SO$_4$. The organic layer was evaporated under reduced pressure to a volume of about 500 ml. The trans isomer, which crystallized, was filtered and the filtrate was reduced to 200 ml. Another fraction of the trans isomer crystallized. The fractions of trans isomer were combined to give the (1S,3R) isomer, Intermediate 67, as white crystals (11.4 g) m.p.: 188° C. [α]$_D^{20°}$=+32.4° (c=1.03, CHCl$_3$).

The filtrate containing mainly the cis isomer was reduced to 100 ml and isopropyl ether (200 ml) was added. Upon cooling, the (1R,3R) isomer, Intermediate 68, crystallized as a white solid (17.4 g).

mp: 154–155° C.

[α]$_D^{20°}$=+24.4° ©=1.03, CHCl$_3$)

Intermediate 69

(1R,3R)-Methyl 1,2,3,4-tetrahydro-1-(3,4-methylenedioxyphenyl)-9H-pyrido[3,4-b]indole-3-carboxylate Method A Intermediate 67 (5.0 g) was dissolved in methanol (150 ml). Hydrogen chloride was bubbled into the solution for several minutes at 0° C. and the resulting yellow solution was refluxed for 24 hours. The solvent was removed under reduced pressure and the residue was basified with a saturated aqueous solution of NaHCO$_3$ and extracted with dichloromethane. The organic layer was washed with water, dried over Na$_2$SO$_4$, and purified by flash chromatography eluting with dichloromethane/methanol (99/1) to give the title compound (2.3 g) corresponding to an authentic sample of Intermediate 68.

Method B

Intermediate 67 (25 g) was heated in 1N hydrochloric acid (78.5 ml) and water (400 ml) at 60° C. for 36 hours. From the initial pale yellow solution, a white solid precipitated. The mixture then was allowed to cool to 0° C. and the solid filtered. The solid then was washed with diisopropyl ether (3×200 ml) and dried to give the hydrochloride salt of the title compound (20 g) as a white solid.

mp (dec.): 209–212° C.

Method C

A 1:1 mixture of the cis and trans isomers of Intermediates 54 and 55 (2 g) was heated in 1N hydrochloric acid (6.8 ml) and water (15 ml) at 50° C. for 72 hours. A similar work-up as described in Method B above gave the hydrochloride salt of the title compound (1.7 g) as a white solid.

Intermediate 70

(R)-N$^α$-(3,4-Methylenedioxyphenylcarbonyl)-tryptophan methyl ester

To a suspension of D-tryptophan methyl ester hydrochloride (10.2 g) in anhydrous CH$_2$Cl$_2$ (150 ml) cooled at 0° C. was added dropwise triethylamine (12.3 ml). To the resulting solution solid piperonyloyl chloride (8.16 g) was added portionwise at the same temperature, and the mixture was stirred at room temperature for 2 h. The mixture was washed successively with water, 0.5N hydrochloric acid, water, a saturated aqueous solution of NaHCO$_3$, and again with water. After drying over Na$_2$SO$_4$ and evaporation of the solvent under reduced presure, the resulting oil on trituration from hot cyclohexane afforded the title compound as a white solid (14.7 g).

mp: 123–124° C.

[α]$_D^{20°}$=−84.4° (c=1.04, CHCl$_3$).

Intermediate 71

(R)-N$^α$-(3,4-Methylenedioxyphenylthiocarbonyl)-tryptophan methyl ester

A mixture of Intermediate 70 (14 g) and Lawesson's reagent (9.28 g) in dimethoxyethane (280 ml) was heated at 60° C. under N$_2$ for 16 hours with stirring. The reaction mixture was evaporated to dryness and the resulting oil was dissolved in ethyl acetate, then washed successively with an aqueous saturated solution of NaHCO$_3$ and water, and dried over Na$_2$SO$_4$. The oily residue obtained after evaporation under reduced pressure gave, on trituration from cyclohexane, a yellow powder which was filtered and washed with cooled methanol to afford the title compound (9.74 g).

mp: 129–130° C.

$[\alpha]_D^{20°}$=–186.8° (c=1.14, CHCl$_3$)

Intermediate 72

(1R,3R)-Methyl 1,2,3,4-tetrahydro-1-(3,4-methylenedioxyphenyl)-9H-pyrido[3,4-b]indole-3-carboxylate A solution of Intermediate 71 (9 g) and methyl iodide (10 ml) in anhydrous dichloromethane (200 ml) was heated at reflux under an argon atmosphere with protection from light. After 24 hours, the solvent was removed under reduced pressure to give an orange oil which on trituration from hexane gave a solid which was washed with ether and used without further purification in the next step. This compound (13.11 g) was dissolved in methanol (250 ml) and the solution was cooled to –78° C. sodium borohydride (0.99 g) then was added by portions and the mixture was stirred at the same temperature for 1 hour. The reaction was quenched by addition of acetone (10 ml) and the solvent was removed under reduced pressure. The residue was dissolved in CH$_2$Cl$_2$, washed with water and then with brine, and dried over Na$_2$SO$_4$. After evaporation of the solvent, the orange oil gave on trituration from a hot mixture of diethyl ether/cyclohexane an orange powder which was recrystallized from diethyl ether/pentane to afford the title compound as a pale yellow solid (5.15 g) corresponding to an authentic sample of Intermediate 68.

Intermediate 73

(1R,3R)-Methyl 1,2,3,4-tetrahydro-2-chloroacetyl-(3,4-methylenedioxyphenyl)-9H-pyrido[3,4-b]indole-3-carboxylate Method A To a stirred solution of Intermediate 72 (9.7 g) and NaHCO$_3$ (2.79 g) in anhydrous CHCl$_3$ (200 ml) was added dropwise chloroacetyl chloride (5.3 ml) at 0° C. under N$_2$. The resulting mixture was stirred for 1 hour at the same temperature and diluted with CHCl$_3$ (100 ml). Water (100 ml) was then added dropwise with stirring to the mixture, followed by a saturated aqueous solution of NaHCO$_3$. The organic layer was washed with water until neutrality and dried over Na$_2$SO$_4$. After evaporation of the solvent under reduced pressure, the oily compound obtained was crystallized from ether to give the title compound as a pale yellow solid (9.95 g).

mp: 233° C.

$[\alpha]_D^{20°}$=–125.4° (c=1.17, CHCl$_3$).

Method B

Chloroacetyl chloride (4 ml) was added dropwise to a solution of Intermediate 72 (16.1 g) and triethylamine (7 ml) in anhydrous CH$_2$Cl$_2$ (200 ml) at 0° C. under N$_2$. The solution was stirred at 0° C. for 30 minutes, then diluted with CH$_2$Cl$_2$ (300 ml). The solution was washed with water (200 ml), a saturated aqueous solution of NaHCO$_3$ (300 ml) and brine (400 ml). After drying over Na$_2$SO$_4$ and evaporation under reduced pressure, the resulting solid was washed with ether (300 ml) to give the title compound as a pale yellow solid (18.3 g).

Intermediate 74

Methyl 1,2,3,4-tetrahydro-6-methyl-1-(3,4-methylenedioxyphenyl)-9H-pyrido[3,4-b]indole-3-carboxylate, cis and trans isomers The cis and trans isomers of the title compound were prepared using the method described in Intermediate 1 but starting from racemic 5-methyl-tryptophan methyl ester and piperonal.

Cis isomer: yellow solid m.p.: 85° C.

Trans isomer: yellow solid m.p.: 185° C.

Intermediates 75 and 76

(1R, 3R)-Methyl 1,2,3,4-tetrahydro-1-(7-(4-methyl-3,4-dihydro-2H-benzo[1,4]oxazinyl))-9H-pyrido[3,4-b]indole-3-carboxylate, cis isomer and (1S, 3R)-Methyl 1,2,3,4-tetrahydro-1-(7-(4-methyl-3,4-dihydro-2H-benzo[1,4]-oxazinyl))-9H-pyrido[3,4-b]indole-3-carboxylate, trans isomer The same method, as described for Intermediates 54 and 55, but starting from D-tryptophan methyl ester and 4-methyl-3,4-dihydro-2H-benzo[1,4]oxazine-7-carboxaldehyde gave Intermediate 75 the cis isomer as an oily compound $^1$H NMR (CDCl$_3$) δ (ppm): 7.6–7.1 (m, 5H); 6.9–6.6 (m, 3H); 5.15 (br s, 1H); 4.3 (t, 2H); 4 (dd, 1H); 3.8 (s, 3H); 3.3 (t, 2H); 3.3–2.95 (m, 2H); 2.9 (s, 3H); 1.6 (br s), and Intermediate 76, the trans isomer as white crystals m.p.: 119–121° C.

Intermediate 77

Methyl 1,2,3,4-tetrahydro-1-(5-(N-benzylindolinyl))-9H-pyrido[3,4-b]indole-3-carboxylate, mixture of (1R, 3R) and (iS, 3R) isomers The same method, as described for Intermediates 54 and 55, but starting from D-tryptophan methyl ester and N-benzylindoline-5-carboxaldehyde gave Intermediate 77 as an oily compound.

Intermediates 78 and 79

(1R 3R)-Methyl 1,2,3,4-tetrahydro-1-(4-carbomethoxyphenyl)-9H-pyrido[3,4-b]indole-3-carboxylate, cis isomer and (1S, 3R)-methyl 1,2,3,4-tetrahydro-1-(4-carbomethoxyphenyl)-9H-pyrido[3,4-b]indole-3-carboxylate, trans isomer The same method, as described for Intermediates 54 and 55, but starting from D-tryptophan methyl ester and methyl 4-formylbenzoate gave Intermediate 78, the cis isomer as white crystals m.p.: 157–160° C. and Intermediate 79, the trans isomer as pale yellow crystals m.p.: 124–126° C.

Intermediate 80

(1R, 3R)-Methyl 1,2,3,4-tetrahydro-2-[2-(benzyloxycarbonyl)-R-prolyl]-1-(3,4-methylenedioxyphenyl)-9H -pyrido[3,4-b]indole-3-carboxylate A solution of N-(benzyloxycarbonyl)-D-proline acid chloride (0.64 g, 2.4 mmol) in anhydrous dichloromethane (10 mL) was added dropwise to a stirred solution of Intermediate 54 (0.7 g, 2 mmol) and triethylamine (0.33 mL, 2.4 mmol) in dichloromethane (15 mL) at 10° C.

The mixture was stirred for 2 h at –10° C. after which it was diluted with dichloromethane (50 mL), washed with hydrochloric acid (1N), water, a saturated solution of NaHCO$_3$, a saturated NaCl solution, and dried over Na$_2$SO$_4$. Evaporation of the solvent and recrystallization of the crude product from methanol gave the title compound as pale yellow crystals (0.75 g) m.p.: 268–270° C.

Intermediate 81

(1R, 3R)-Methyl 1,2,3,4-tetrahydro-2-[2-(benzyloxycarbonyl)-S-prolyl]-1-(3,4-methylenedioxyphenyl)-9H pyrido[3.4-b]indole-3-carboxylate A solution of N-(benzyloxycarbonyl)-L-proline acid chloride (0.86 g, 3.2 mmol) in anhydrous dichloromethane (10 mL) was added dropwise to a stirred solution of Intermediate 54 (0.91 g, 2.6 mmol) and triethylamine (0.44 mL, 3.2 mmol) in dichloromethane (20 mL) at 10° C. The mixture was stirred for 2 hours at 10° C. after which it was diluted with dichloromethane (60 mL), washed with hydrochloric acid (1N), water, a saturated solution of NaHCO$_3$, a saturated NaCl solution, and dried over Na$_2$SO$_4$. Evaporation of the solvent and recrystallization of the crude product from methanol/water gave the title compound as pale yellow crystals (0.8 g) m.p.: 115–120° C.

Intermediate 82

(1R, 3R)-Methyl 1,2,3,4-tetrahydro-2-(2-chloropropionyl)-1-(3,4-methylenedioxyphenyl)-9H-pyrido[3,4-b]indole-3-carboxylate To a solution of (S)-(−)-2-chloropropionic acid (87 μl, 1 mmol) in anhydrous dichloromethane (15 mL), was added dicyclohexylcarbodiimide (0.23 g, 1.1 mmol). Intermediate 54 (0,35 g, 1 mmol) then was added and the mixture was stirred at room temperature for 20 hours. The formed precipitate of dicyclohexylurea was removed by filtration, the filtrate was evaporated in vacuo and the crude product was purified by flash chromatography eluting with toluene/ethyl acetate: 95/5. The oily compound obtained then was crystallized from ether/hexane to give the title compound as pale yellow crystals (0.31 g) m.p.: 125–127° C.

Intermediate 83

(1R, 3R)-Methyl 1,2,3,4-tetrahydro-2-(2-chloropropionyl)-1-(3,4-methylenedioxyphenyl)-9H-pyrido[3,4-b]indole-3-carboxylate To a solution of (R)-(+)-2-chloropropionic acid (191 μl, 2.2 mmol) in anhydrous dichloromethane (30 mL), was added dicyclohexylcarbodiimide (0.45 g, 2.2. mol). Intermediate 54 (0.7 g, 2 mmol) then was added and the mixture was stirred at room temperature for 20 hours. The formed precipitate of dicyclohexylurea was removed by filtration, the filtrate was evaporated in vacuo and the crude product was purified by flash chromatography eluting with toluene/ethyl acetate: 95/5. The oily compound obtained then was crystallized from ether/hexane to give the title compound as pale yellow crystals (0.74 g) m.p.: 126–128° C.

Intermediates 84 and 85

(1R, 3R)-Methyl 1,2,3,4-tetrahydro-1-(3,4-dibenzyloxyphenyl)-9H-pyrido[3,4-b]indole-3-carboxylate cis isomer and (1S, 3R)-methyl 1,2,3,4-tetrahydro-1-(3,4-dibenzyloxyphenyl)-9H-pyrido[3,4-b]indole-3-carboxylate trans isomer The same method as described for Intermediates 54 and 55 but starting from D-tryptophan methyl ester and 3,4-dibenzyloxybenzaldehyde gave Intermediate 84, the cis isomer as an oily compound $^1$H NMR (CDCl$_3$) δ (ppm): 7.5–6.95 (m, 15H); 6.85 (s, 1H); 6.75 (s, 2H); 5.1 (s, 2H); 5 (br s, 1H); 4.95 (d, 2H) 3.85 (dd, 1H); 3.7 (s, 3H); 3.2–2.8 (m, 2H); 2.3 (br s, 1H), and Intermediate 85, the trans isomer as an oily compound $^1$HNMR (CDCl$_3$) δ (ppm) 7.6–7 (m, 15H); 6.9–6.7 (m, 3H); 5.2 (br s, 1H); 5.1 (s, 2H); 5 (s, 2H); 3.8 (t, 1H); 3.65 (s, 3H); 3.3–3 (m, 2H); 2.25 (br s, 1H).

Intermediate 86

(6R, 12aR)-2,3,6,7,12,12a-Hexahydro-6-(3,4-dibenzyloxyohenyl)-2-methyl-pyrazino[2',1';6,1]pyrido[3,4-b]indole-1,4-dione The same two-step procedure but starting from Intermediate 84 and methylamine gave, after recrystallization from dichloromethane/ether, the title compound as white crystals m.p.: 158–160° C., [α]$^{20°}_D$=+11.7° (c=1.23; CHCl$_3$)

Intermediate 87

Methyl 1,2,3,4-tetrahydro-1-(5-(2-methylisoindolinyl))-9H-pyrido[3,4-b]indole-3-carboxylate, mixture of (1R,3R) and (1S,3R) isomers The same method, as described for Intermediates 54 and 55, but starting from D-tryptophan methyl ester and N-methylisoindoline-5-carboxaldehyde gave Intermediate 87 as an oily compound.

Intermediates 88 and 89

(1R,3R)-Methyl 1,2,3,4-tetrahydro-1-(5-benzofuranyl)-9H-pyrido[3,4-b]indole-3-carboxylate, cis isomer and (1S,3R)-methyl 1,2,3,4-tetrahydro-1-(5-benzofuranyl)-9H-pyrido[3,4-b]indole-3-carboxylate trans isomer To a stirred solution of D-tryptophan methyl ester (3.73 g) and 5-formyl-benzofuran (2.5 g) in anhydrous dichloromethane (100 mL) cooled at 0° C. was added dropwise trifluoroacetic acid (2.63 mL) and the solution was allowed to react at ambient temperature. The synthesis of 5-formyl-benzofuran is described in *Chimie Therapeutique*, 4, pp. 221–227 (1966), incorporated herein by reference. After 72 hours, the solution was washed with a saturated aqueous solution of NaHCO$_3$, then with water, and dried over Na$_2$SO$_4$. The organic layer was evaporated under reduced pressure and the residue was purified by flash chromatography eluting with dichloromethane/ethyl acetate (90/10) to give first the cis isomer (Intermediate 1) (3 g) as an amorphous compound, followed by the trans isomer (Intermediate 2) (2.5 g) as white crystals, m.p.: 194–195° C.

Intermediate 90

(1R,3R)-Methyl 1,2,3,4-tetrahydro-1-(5-benzofuranyl)-2-chloroacetyl-9H-pyrido[3,4-b]indole-3-carboxylate To a stirred solution of Intermediate 88 (2 g) and triethylamine (0.88 mL) in anhydrous dichloromethane (40 mL) cooled at 0° C. was added dropwise chloroacetyl-chloride (0.5 mL) and the solution was stirred at the same temperature for 1 hour. The solution was washed with water, dried over Na$_2$SO$_4$, and evaporated to dryness and the residue was crystallized from methanol to give the title compound (1.8 g) as page yellow crystals). m.p.: 227–228° C.

Intermediate 91

(1R,3R)-Methyl 1,2,3,4-tetrahydro-1-(5-benzofuranyl)-2-(2-(S)-benzyloxycarbonylaminopropionyl)-9H-pyrido[3,4-b]indole-3-carboxylate To a stirred solution of (S)-2-benzyloxycarbonylaminopropionic acid (1.3 g) and 1,3-dicyclohexyl carbodiimide (DCC) (1.2 g) in anhydrous dichloromethane (50 ml) at 0° C. was added Intermediate 88 (1.0 g). The resulting mixture was stirred for 72 hours, then the resulting precipitate filtered off. The filtrate was evaporated to dryness and the residue purified by flash chromatography, eluting with cyclohexane/ethyl acetate (60/40) to give the title compound as white crystals (1.4 g) m.p.: 91–92° C.

Intermediate 92

(1R,3R)-Methyl 1,2,3,4-tetrahydro-1-(5-benzofuranyl)-2-[2-(S)-benzyloxycarbonylmethylamino)-propionyl]-9H-pyrido-3,4-b[indole-3-carboxylate The same procedure as employed in the preparation of Intermediate 91 but starting rom 2-(S)-benzyloxycarbonylmethylamino)propionic acid (0.82 g) and using Intermediate 1 (0.6 g), DCC (0.72 g) and dichloromethane (25 ml) gave after chromatography, eluting with cyclohexane/ethyl acetate (70/30), the title compound as a white foam. $^1$H NMR (240 MHZ, CDCl$_3$) δ 7.7 (s, 1H), 7.6 (d, 2H), 7.4–7.05 (m, 11H), 6.6 (d, 1H), 5.4–5.0 (m, 4H), 3.5 (d, 1H), 30 (m, 1H), 2.9–2.7 (m, 6H), 2.6 (dd, 1H), 1.3 (s, 3H).

EXAMPLE 1

Cis-2,3,6,7,12,12a-hexahydro-2-methyl-6-(3,4-methylenedioxyphenyl)-pyrazino[2',1';6,1]pyrido[3,4-b]indole-1,4-dione a) To a stirred solution of Intermediate 1 (2 g) and NaHCO$_3$ (0.6 g) in anhydrous CHCl$_3$ (40 mL) was added dropwise chloroacetyl chloride (1.1 mL) at 0° C.. The resulting mixture was stirred for 1 hour at the same temperature and diluted with CHCl$_3$. Water (20 mL) then was added dropwise with stirring to the mixture, followed by a saturated solution of NaHCO$_3$. The organic layer was washed with water until neutrality and dried over Na$_2$SO$_4$. After evaporation of the solvent under reduced pressure, cis-methyl 1,2,3,4-tetrahydro-2-chloroacetyl-1-(3, 4methylenedioxyphenyl)-9H-pyrido[3,4-b]indole-3-carboxylate was obtained as an oil, which was crystallized from ether (2 g, m.p.: 215–218°) and was used without further purification in the next step.

(b) To a stirred suspension of the chloroacetyl Intermediate (0.34 g) in MeOH (20 mL) was added at ambient temperature a solution of methylamine (33% in EtOH) (0.37 mL) and the resulting mixture was heated at 50° C. under N$_2$ for 14 hours. The solvent was removed under reduced pressure and the residue was dissolved in CH$_2$Cl$_2$ (50 mL). After washing with water (3×30 mL), drying over Na$_2$SO$_4$, and evaporating to dryness, the residue was purified by flash chromatography eluting with CH$_2$Cl$_2$/MeOH (99/1) and recrystallized from MeOH to give the title compound as white crystals (0.19 g) m.p.: 253–255° C.

Analysis for C$_{22}$H$_{19}$N$_3$O$_4$:
Calculated: C,67.86; H,4.92; N,10.79;
Found: C,67.53; H,4.99; N,10.62%.

The following compounds were obtained in a similar manner:

EXAMPLE 2

Cis-2,3,6,7,12,12a-hexahydro-2-butyl-10-fluoro-6-(4-methoxyphenyl)-pyrazino[2',1';6,1]pyrido[3,4-b]indole-1,4-dione The same two-step procedure, but starting from butylamine and Intermediate 52 gave, after recrystallization from ethanol, the title compound as white crystals
m.p.: 182° C.
Analysis for C$_{25}$H$_{26}$FN$_3$O$_3$ (0.1 H$_2$O)
Calculated: C, 68.67; H, 6.04; N, 9.61;
Found: C, 68.38; H, 6.11; N, 9.53%.

EXAMPLE 3

Trans-2,3,6,7,12,12a-hexahydro-2-methyl-6-(3,4-methylenedioxyphenyl)-pyrazino[2',1';6,1]pyrido[3,4-b]indole-1,4-dione The same two-step procedure, but starting from methylamine and Intermediate 2 gave, after recrystallization from toluene, the title compound as white crystals
m.p.: 301–303° C.
Analysis for C$_{22}$H$_{19}$N$_3$O$_4$:
Calculated: C,67.86; H,4.92; N,10.79;
Found: C,67.98; H,4.98; N,10.73%.

EXAMPLE 4

Cis-2,3,6,7,12,12a-hexahydro-6-(3,4-methylenedioxyphenyl)-pyrazino[2',1';6,1]pyrido[3,4-b]indole-1,4-dione The same two-step procedure but starting from ammonia and Intermediate 1 gave, after recrystallization from methanol, the title compound as white crystals m.p.: 283–285° C.
Analysis for C$_{21}$H$_{17}$N$_3$O$_4$:
Calculated: C,67.19; H,4.56; N,11.19;
Found: C,67.04; H,4.49; N,11.10%.

EXAMPLE 5

Cis-2,3,6,7,12,12a-hexahydro-10-fluoro-6-(4-methoxyphenyl)-2-(2,2,2-trifluoroethyl)-pyrazino[2',1';6,1]-pyrido[3,4-b]indole-1,4-dione The same two-step procedure, but starting from 2,2,2-trifluoroethylamine and Intermediate 52 gave, after recrystallization from ethanol/diisopropyl ether, the title compound as white crystals m.p.: 190° C.
Analysis for C$_{23}$H$_{19}$F$_4$N$_3$O$_3$:
Calculated: C, 59.87; H, 4.15; N, 9.11;
Found: C, 59.81; H, 4.18; N, 9.21%.

EXAMPLE 6

Cis-2,3,6,7,12,12a-hexahydro-10-fluoro-2-methyl-6-(3,4-methylenedioxyphenyl)-pyrazino[2',1';6,1]pyrido[3,4-b]indole-1,4-dione The same two-step procedure but starting from methylamine and Intermediate 50 gave, after recrystallization from ethanol, the title compound as white crystals m.p.: 292° C.
Analysis for C$_{22}$H$_{18}$FN$_3$O$_4$:
Calculated: C, 64.86; H, 4.45; N, 10.31;
Found: C, 64.66; H, 4.60; N, 10.21%.

EXAMPLE 7

(6R, 12aS)-2,3,6,7,12,12a-hexahydro-2-methyl-6-(3,4-methylenedioxyphenyl)-pyrazino[2',1';6.1]pyrido[3,4-b]indole-1,4-dione The same two-step procedure but starting from methylamine and the trans isomer of Intermediate 56 gave, after recrystallization from toluene, the title compound as white crystals m.p.: 287–289° C.
Analysis for C$_{22}$H$_{19}$N$_3$O$_4$ (0.25 toluene):
Calculated: C, 69.16; H, 5.13; N, 10.19;
Found: C,69.09; H,5.14; N,10.19%.
$[\alpha]_D^{20°}$=−293.40 (C=1.28; CHCl$_3$)

EXAMPLE 8

(6S, 12aR)-2,3,6,7,12,12a-hexahydro-2-methyl-6-(3,4-methylenedioxyphenyl)-pyrazino [2',1';6.1]pyrido[3,4-b]indole-1,4-dione The same two-step procedure but starting from methylamine and Intermediate 55 gave, after recrystal lization from toluene, the title compound as white crystals m.p.: 287° C.
Analysis for C$_{22}$H$_{19}$N$_3$O$_4$ (0.3 toluene)
Calculated: C, 69.41; H, 5.17; N, 10.08;
Found: C, 69.56; H,5.24; N, 10.08%.
$[\alpha]_D^{20°}$=+297.9° (c=1.21; CHCl$_3$)

EXAMPLE 9

Cis-2,3,6,7,12,12a-hexahydro-2-[2-(2-pyridyl)-ethyl]-6-(3,4-methylenedioxyphenyl)-pyrazino[2',1'-6,1]pyrido[3,4-b]indole-1,4-dione The same two-step procedure but starting from 2-(2-pyridyl)ethylamine and Intermediate 1 gave, after recrystallization from 2-propanol, the title compound as white crystals m.p.: 218–222° C.
Analysis for C$_{28}$H$_{24}$N$_4$O$_4$:
Calculated: C, 69.99; H, 5.03; N, 1166;
Found: C, 69.92; H. 5.16; N, 11.48%.

EXAMPLE 10

Cis-2,3,6,7,12,12a-hexahydro-2-(2-pyridylmethyl)-6-(3,4-methylenedioxyphenyl)-pyrazino[2',1';6,1]pyrido[3,4-b]indole-1,4-dione The same two-step procedure but starting from 2-pyridylmethylamine and Intermediate 1 gave, after recrystallization from DMF/water, the title compound as cream crystals m.p: 285–286° C.
Analysis for C$_{27}$H$_{22}$N$_4$O$_4$ (0.4 H$_2$O)
Calculated: C, 68.46; H,4.85; N, 11.83;
Found: C, 68.58; H, 4.88; N, 11.90%.

EXAMPLE 11

Cis-2,3,6,7,12,12a-hexahydro-2-(3-pyridylmethyl)-6-(3,4-methylenedioxyphenyl)-pyrazino[2',1';6,1]pyrido[3,4-b]indole-1,4-dione The same two-step procedure but starting from 3-pyridylmethylamine and Intermediate 1 gave, after recrystallization from $CH_2Cl_2$/MeOH, the title compound as cream crystals m.p.: 292–293° C.

Analysis: $C_{27}H_{22}N_4O_4$:
Calculated: C, 69.52; H, 4.75; N, 12.01;
Found: C, 69.27; H, 4.74; N, 11.37%.

EXAMPLE 12
Cis-2,3,6,7,12,12a-hexahydro-2-(4-pyridylmethyl)-6-(3,4-methylenedioxyphenyl)-pyrazino[2',1';6,1]pyrido[3,4-b]indole-1,4-dione The same two-step procedure but starting from 4-pyridylmethylamine and Intermediate 1 gave, after recrystallization from MeOH, the title compound as pale yellow crystals m.p.: 273–274° C.

Analysis for $C_{27}H_{22}N_4O_4$ (1.8 $H_2O$):
Calculated: C, 65.00; H, 5.17; N, 11.23;
Found: C, 65.11; H, 4.85; N, 11.07%.

EXAMPLE 13
Cis-2,3,6,7,12,12a-hexahydro-2-ethyl-6-(3,4-methylenedioxyphenyl)-pyrazino[2',1';6,1]pyrido[3,4-b]indole-1,4-dione The same two-step procedure but starting from ethylamine and Intermediate 1 gave, after recrystallization from methanol, the title compound as white crystals m.p.: 272–274° C.

Analysis for $C_{23}H_{21}N_3O_4$:
Calculated: C,68.47; H,5.25; N,10.42;
Found: C,68.52; H,5.35; N,10.53%.

EXAMPLE 14
Cis-2,3,6,7,12,12a-hexahydro-2-(2,2,2-trifluoroethyl)-6-(3,4-methylenedioxyphenyl)-pyrazino2',1';6,1]pyrido[3,4-b]indole-1,4-dione The same two-step procedure but starting from 2,2,2-trifluoroethylamine and Intermediate 1 gave, after recrystallization from EtOH, the title compound as white crystals m.p.: 303° C.

Analysis for $C_{23}H_{18}F_3N_3O_4$:
Calculated: C,60.40; H,3.97; N,9.19;
Found: C,60.43; H,4.15; N,9.16%.

EXAMPLE 15
Cis-2,3,6,7,12,12a-hexahydro-6-(3,4-methylenedioxyphenyl)-2-propyl-pyrazino[2',1';6,1]pyrido[3,4-b]indole-1,4-dione The same two-step procedure but starting from propylamine and Intermediate 1 gave, after recrystallization from methanol, the title compound as white crystals m.p.: 270–271° C.

Analysis for $C_{24}H_{23}N_3O_4$:
Calculated: C,69.05; H,5.55; N,10.07;
Found: C,69.22; H,5.50; N,9.80%.

EXAMPLE 16
Cis-2,3,6,7,12,12a-hexahydro-2-isopropyl-6-(3,4-methylenedioxyphenyl)-pyrazino[2',1';6,1]pyrido[3,4-b]indole-1,4-dione The same two-step procedure but starting from isopropylamine and Intermediate 1 gave, after recrystallization from methanol, the title compound as white crystals m.p.: 248–250° C.

Analysis for $C_{24}H_{23}N_3O_4$:
Calculated: C,69.05; H,5.55; N,10.07;
Found: C,68.86; H,5.66; N,10.21%.

EXAMPLE 17
Cis-2,3,6,7,12,12a-hexahydro-2-cyclopropyl-6-(3,4-methylenedioxyphenyl)-pyrazino[2',1';6,1]pyrido[3,4-b]indole-1,4-dione The same two-step procedure but starting from cyclopropylamine and Intermediate 1 gave, after recrystallization from methanol, the title compound as white crystals m.p.: 290–292° C.

Analysis for $C_{24}H_{21}N_3O_4$:
Calculated: C,69.39; H,5.10; N,10.11;
Found: C,69.11; H,5.20; N,9.94%.

EXAMPLE 18
Cis-2,3,6,7,12,12a-hexahydro-2-butyl-6-(3,4-methylenedioxyphenyl)-pyrazino[2',1';6,1]pyrido[3,4-b]indole-1,4-dione The same two-step procedure but starting from butylamine and Intermediate 1 gave, after recrystallization from methanol/water, the title compound as white crystals m.p.: 241–243° C.

Analysis for $C_{25}H_{25}N_3O_4$:
Calculated: C,69.59; H,5.84; N,9.74;
Found: C,69.77; H,5.82; N,9.81%.

EXAMPLE 19
Trans-2,3,6,7,12,12a-hexahydro-2-butyl-6-(3,4-methylenedioxyphenyl)-pyrazino[2',1';6,1]pyrido[3,4-b]indole-1,4-dione The same two-step procedure but starting from butylamine and Intermediate 2 gave, after recrystallization from toluene, the title compound as white crystals m.p.: 243° C.

Analysis for $C_{25}H_{25}N_3O_4$:
Calculated: C,69.59; H,5.84; N,9.74;
Found: C,69.80; H,5.78; N,9.52%.

EXAMPLE 20
Cis-2,3,6,7,12,12a-hexahydro-2-cyclopropylmethyl-6-(3,4-methylenedioxyphenyl)-pyrazino[2',1';6,1]pyrido[3,4-b]indole-1,4-dione The same two-step procedure but starting from cyclopropylmethylamine and Intermediate 1 gave, after recrystallization from methanol, the title compound as white crystals m.p.: 217–218° C.

Analysis for $C_{25}H_{23}N_3O_4$:
Calculated: C,69.92; H,5.40; N,9.78;
Found: C,70.02; H,5.47; N,9.84%.

EXAMPLE 21
Cis-2,3,6,7,12,12a-hexahydro-2-cyclopentyl-6-(3,4-methylenedioxyphenyl)-pyrazino[2',1';6,1]pyrido[3,4-b]indole-1,4-dione The same two-step procedure but starting from cyclopentylamine and Intermediate 1 gave, after recrystallization from acetone, the title compound as white crystals m.p.: 270° C.

Analysis for $C_{26}H_{25}N_3O_4$:
Calculated: C,70.41; H,5.68; N,9.47;
Found: C,70.58; H,5.63; N,9.38%.

EXAMPLE 22
Cis-2,3,6,7,12,12a-hexahydro-2-cyclohexyl-6-(3,4-methylenedioxyphenyl)-pyrazino[2',1';6,1]pyrido[3,4-b]indole-1,4-dione The same two-step procedure but starting from cyclohexylamine and Intermediate 1 gave, after recrystallization from methanol/water, the title compound as white crystals m.p.: 268–269° C.

Analysis for $C_{27}H_{27}N_3O_4$:
Calculated: C,70.88; H,5.95; N,9.18;
Found: C,70.82; H,5.89; N,9.21%.

EXAMPLE 23
Cis-2,3,6,7,12,12a-hexahydro-2-benzyl-6-(3,4-methylenedioxyphenyl)-pyrazino[2',1';6,1]pyrido[3,4-b]indole-1,4-dione The same two-step procedure but starting from benzylamine and Intermediate 1 gave, after recrystallization from dichloromethane/hexane, the title compound as white crystals m.p.: 285–287° C.

Analysis for $C_{28}H_{23}N_3O_4$ (1 $H_2O$):
Calculated: C,69.55; H,5.21; N,8.69;
Found: C,69.30; H,5.06; N,8.48%.

EXAMPLE 24

Cis-2,3,6,7,12,12a-hexahydro-2-(4-fluorobenzyl)-6-(3,4-methylenedioxyphenyl)-pyrazino[2',1';6,1]pyrido[3,4-b]-indole-1,4-dione The same two-step procedure but starting from 4-fluorobenzylamine and Intermediate 1 gave, after recrystallization from acetone, the title compound as white crystals m.p.: 281–283° C.

Analysis for $C_{28}H_{22}FN_3O_4$:
Calculated: C,69.56; H,4.59; F,3.93; N,8.69;
Found: C69.54; H,4.58; F,3.82; N,8.63%.

EXAMPLE 25

Cis-2,3,6,7,12,12a-hexahydro-6-(4-methoxyphenyl)-2-methyl-pyrazino[2',1';6,1]pyrido[3,4-b]indole-1,4-dione The same two-step procedure but starting from methylamine and Intermediate 3 gave, after recrystallization from 2-propanol, the title compound as white crystals m.p.: 257–263° C.

Analysis for $C_{22}H_{21}N_3O_3$:
Calculated: C,70.38; H,5.64; N,11.19;
Found; C,70.11; H,5.55; N,11.15%.

EXAMPLE 26

Trans-2,3,6,7,12,12a-hexahydro-6-(4-methoxyphenyl)-2-methyl-pyrazino[2',1';6,1]pyrido[3,4-b]indole-1,4-dione The same two-step procedure but starting from methylamine and Intermediate 4 gave, after recrystallization from diisopropyl ether, the title compound as white crystals m.p.: 225–228° C.

Analysis for $C_{22}H_{21}N_3O_3$:
Calculated: C,70.38; H,5.64; N,11.19;
Found: C,70.34; H,5.77; N,11.19%.

EXAMPLE 27

Cis-2,3,6,7,12,12a-hexahydro-2-ethyl-6-(4-methoxyphenyl)-pyrazino[2',1';6,1]pyrido[3,4-b]indole-1,4-dione The same two-step procedure but starting from ethylamine and Intermediate 3 gave, after recrystallization from methanol, the title compound as white crystals m.p.: 245–255° C.

Analysis for $C_{23}H_{23}N_3O_3$:
Calculated: C,70.93; H,5.95; N,10.79;
Found: C,70.74; H,6.06; N,10.87%.

EXAMPLE 28

Cis-2,3,6,7,12,12a-hexahydro-6-(4-methoxyphenyl)-2-(2,2,2-trifluoroethyl)pyrazino[2',1';6,1]pyrido[3,4-b]-indole-1,4-dione The same two-step procedure but starting from 2,2,2-trifluoroethylamine and Intermediate 3 gave, after recrystallization from ethanol, the title compound as white crystals m.p.: 232° C.

Analysis for $C_{23}H_{20}F_3N_3O_3$:
Calculated: C,62.30; H,4.55; N,9.48;
Found: C,62.08; H,4.66; N,9.54%.

EXAMPLE 29

Cis-2,3,6,7,12,12a-hexahydro-2-butyl-6-(4-methoxyphenyl)-pyrazino[2',1';6,1]pyrido[3,4-b]indole-1,4-dione The same two-step procedure but starting from butylamine and Intermediate 3 gave, after recrystallization from methanol, the title compound as white crystals m.p.: 157° C.

Analysis for $C_2H_{27}N_3O_3$(0.5 $H_2O$)
Calculated: C,70.40; H,6.62; N,9.85;
Found: C,70.25; H,6.60; N,9.83%.

EXAMPLE 30

Trans-2,3,6,7,12,12a-hexahydro-2-butyl-6-(4-methoxyphenyl)-pyrazino[2',1';6,1]pyrido[3,4-b]indole-1,4-dione The same two-step procedure but starting from butylamine and Intermediate 4 gave, after recrystallization from methanol, the title compound as white crystals m.p.: 212–214° C.

Analysis for $C_{25}H_{27}N_3O_3$:
Calculated: C,71.92; H,6.52; N,10.06;
Found: C,71.81; H,6.55; N,10.03%.

EXAMPLE 31

Cis-2,3,6,7,12,12a-hexahydro-6-(4-methoxyphenyl)-2-cyclopropylmethyl-pyrazino[2',1';6,1]pyrido[3,4-b]indole-1,4-dione The same two-step procedure but starting from cyclopropylmethylamine and Intermediate 3 gave, after recrystallization from methanol, the title compound as white crystals m.p.: 180–185° C.

Analysis for $C_{25}H_{25}N_3O_3$ (0.5 $H_2O$):
Calculated: C,70.74; H,6.17; N,9.90;
Found: C,70.91; H, 6.16; N, 9.80%.

EXAMPLE 32

Cis-2,3,6,7,12,12a-hexahydro-2-benzyl-6-(4-methoxyphenyl)-pyrazino[2',1';6,1]pyrido[3,4-b]indole-1,4-dione The same two-step procedure but starting from benzylamine and Intermediate 3 gave, after recrystallization from acetone, the title compound as white crystals m.p.: 275–279° C.

Analysis for $C_2H_{25}N_3O_3$:
Calculated: C,74.48; H,5.58; N,9.31;
Found: C,74.53; H,5.60; N,9.20%.

EXAMPLE 33

Cis-2,3,6,7,12,12a-hexahydro-6-(3-methoxyphenyl)-2-methyl-pyrazino[2',1';6,1]pyrido[3,4-b]indole-1,4-dione The same two-step procedure but starting from methylamine and Intermediate 5 gave, after recrystallization from methanol, the title compound as white crystals m.p.: 267–269° C.

Analysis for $C_{22}H_{21}N_3O_3$:
Calculated: C,70.38; H,5.64; N,11.19;
Found: C,70.32; H,5.59; N,11.25%.

EXAMPLE 34

Cis-2,3,6,7,12,12a-hexahydro-6-(4-ethoxyphenyl)-2-methyl-pyrazino[2',1';6,1]pyrido[3,4-b]indole-1,4-dione The same two-step procedure but starting from methylamine and Intermediate 6 gave, after recrystallization from methanol, the title compound as white crystals m.p.: 247–248° C.

Analysis for $C_{23}H_{23}N_3O_3$:
Calculated: C,70.93; H,5.95; N,10.79;
Found: C,71.23; H,5.95; N,10.63%.

EXAMPLE 35

Cis-2,3,6,7,12,12a-hexahydro-6-(4-ethoxyphenyl)-2-cyclopropylmethyl-pyrazino[2',1';6,1]pyrido[3,4-b]indole 1,4-dione The same two-step procedure but starting from cyclopropylmethylamine and Intermediate 6 gave, after recrystallization from 2-propanol, the title compound as white crystals m.p.: 160–162° C.

Analysis for $C_2H_{27}N_3O_3$:
Calculated: C,72.71; H,6.34; N,9.78;
Found: C,72.28; H,6.39; N,9.71%.

EXAMPLE 36
Cis-2,3,6,7,12,12a-hexahydro-6-(2,3-dihydrobenzo[b]furan-5-yl)-2-methyl-pyrazino[2',1';6,1]pyrido[3,4-b]indole-1,4-dione The same two-step procedure but starting from methylamine and Intermediate 8 gave, after recrystallization from methanol, the title compound as white crystals m.p.: 292–294° C.

Analysis for $C_{23}H_{21}N_3O_3$:
Calculated: C,71.30; H,5.46; N,10.85;
Found: C,71.15; H,5.56; N,10.84%.

EXAMPLE 37
Cis-2,3,6,7,12,12a-hexahydro-6-(2,3-dihydrobenzo[b]furan-5-yl)-2-cyclopropylmethyl-pyrazino[2',1';6,1]pyrido[3,4-b]indole-1,4-dione The same two-step procedure but starting from cyclopropylmethylamine and Intermediate 8 gave, after recrystallization from methanol, the title compound as white crystals m.p.: 165–166° C.

Analysis for $C_{26}H_{25}N_3O_3$:
Calculated: C,73.05; H,5.89; N,9.83;
Found: C,73.08; H,5.97; N,9.87%.

EXAMPLE 38
Cis-2,3,6,7,12,12a-hexahydro-6-(3,4-ethylenedioxyphenyl)-2-methyl-pvrazino[2',1';6,1]pyrido[3,4-b]indole-1,4-dione The same two-step procedure but starting from methylamine and Intermediate 10 gave, after recrystallization from acetone, the title compound as white crystals m.p.: 303–305° C..

Analysis for $C_{23}H_{21}N_3O_4$:
Calculated: C,68.47; H,5.25; N,10.42;
Found: C,68.35; H,5.31; N,10.27%.

EXAMPLE 39
Cis-2,3,6,7,12,12a-hexahydro-6-(3,4-ethylenedioxyphenyl)-2-cyclopropylmethyl-pyrazino[2',1';6,1]pyrido[3,4-b]-indole-1,4-dione The same two-step procedure but starting from cyclopropylmethylamine and Intermediate 10 gave, after recrystallization from dichloromethane/ether, the title compound as white crystals m.p.: 288–290° C.

Analysis for $C_{26}H_{26}N_3O_4$:
Calculated: C,70.41; H,5.68; N,9.47;
Found: C,70.15; H,5.62; N,9.30%.

EXAMPLE 40
Cis-2,3,6,7,12,12a-hexahydro-2-butyl-6-(2-chlorophenyl)-pyrazino[2',1';6,1]pyrido[3,4-b]indole-1,4-dione The same two-step procedure but starting from butylamine and Intermediate 12 gave, after recrystallization from methanol/water, the title compound as white crystals m.p.: 146° C.

Analysis for $C_{24}H_{24}ClN_3O_2$ (0.75 $H_2O$)
Calculated: C,66.20; H,5.90; N,9.65;
Found: C,66.15; H,5.95; N,9.69%.

EXAMPLE 41
Cis-2,3,6,7,12,12a-hexahydro-6-(4-chlorophenyl)-2-methyl-pyrazino[2',1';6,1]pyrido[3,4-b]indole-1,4-dione The same two-step procedure but starting from methylamine and Intermediate 13 gave, after recrystallization from methanol, the title compound as white crystals m.p.: 274° C.

Analysis for $C_{21}H_{18}ClN_3O_2$ (0.25 $H_2O$)
Calculated: C,65.63; H,4.85; N,10.93;
Found: C,65.39; H,4.84; N,10.85%.

EXAMPLE 42
Cis-2,3,6,7,12,12a-hexahydro-2-butyl-6-(4-chlorophenyl)-pyrazino[2',1';6,1]pyrido[3,4-b]indole-1,4-dione The same two-step procedure but starting from butylamine and Intermediate 13 gave, after recrystallization from ethanol/water, the title compound as white crystals m.p.: 164–166° C.

Analysis for $C_{24}H_{24}ClN_3O_2$:
Calculated: C,68.32; H,5.73; Cl,8.40; N,9.96;
Found: C,68.48; H,5.64; Cl,8.37; N,9.99%.

EXAMPLE 43
Cis-2,3,6,7,12,12a-hexahydro-6-(3,4-dichlorophenyl)-2-methyl-pyrazino[2',1';6,1]pyrido[3,4-b]indole-1,4-dione The same two-step procedure but starting from methylamine and Intermediate 15 gave, after recrystallization from ethanol/DMF, the title compound as white crystals m.p.: >260° C.

Analysis for $C_{21}H_{17}Cl_2N_3O_2$ (0.5 $H_2O$)
Calculated: C,59.39; H,4.29; N,9.93;
Found: C,59.32; H,4.16; N,9.99%.

EXAMPLE 44
Cis-2,3,6,7,12,12a-hexahydro-2-butyl-6-phenyl-pyrazino[2',1';6,1]pyrido[3,4-b]indole-1,4-dione The same two-step procedure but starting from butylamine and cis-methyl 1,2,3,4-tetrahydro-1-phenyl-9H-pyrido[3,4-b]indole-3-carboxylate (see D. Soerens et al., *J. Org. Chem.*, 44, 535–545 (1979)) gave, after recrystallization from methanol/water, the title compound as white crystals m.p.: 243–245SC.

Analysis for $C_{24}H_{25}N_3O_2$:
Calculated: C,74.39; H,6.50; N,10.84;
Found: C,74.54; H,6.51; N,10.86%.

EXAMPLE 45
Cis-2,3,6,7,12,12a-hexahydro-2-benzyl-6-phenyl-pyrazino[2',1';6,1]pyrido[3,4-b]indole-1,4-dione The same two-step procedure but starting from benzylamine and cis-methyl-1,2,3,4-tetrahydro-1-phenyl-9H-pyrido[3,4-b]indole-3-carboxylate gave, after recrystallization from methanol, the title compound as white crystals m.p.: 193–195° C.

Analysis for $C_{27}H_{23}N_3O_2$:
Calculated: C,76.94; H,5.50; N.9.97;
Found: C,77.23; H,5.54; N,9.97%.

EXAMPLE 46
Trans-2,3,6,7,12,12a-hexahydro-2-benzyl-6-phenyl-pyrazino[2',1';6,1]pyrido[3,4-b]indole-1,4-dione The same two-step procedure but starting from benzylamine and cis-methyl-1,2,3,4-tetrahydro-1-phenyl-9H-pyrido[3,4-b]indole-3-carboxylate gave, after recrystallization from methanol, the title compound as white crystals m.p.: 284° C.

Analysis for $C_{27}H_{23}N_3O_2$:
Calculated: C,76.94; H,5.50; N,9.97;
Found: C,76.88; H,5.45; N,9.89%.

EXAMPLE 47
Cis-2,3,6,7,12,12a-hexahydro-2-methyl-6-(1,2,3,4-tetrahydro-6-naphthyl)-pyrazino[2',1';6,1]pyrido[3,4-b]-indole-1,4-dione

EXAMPLE 48
Cis-2,3,6,7,12,12a-hexahydro-2-isopropyl-6-(1,2,3,4-tetrahydro-6-naphthyl)-pyrazino[2',1';6,1]pyrido[3,4-b]indole-1,4-dione The same two-step procedure but starting from isopropylamine and Intermediate 17 gave, after recrystallization from the title compound as off-white crystals m.p.: 244–246° C.

Analysis for $C_{27}H_{29}N_3O_2$ (0.25 $H_2O$)
Calculated: C,75.06; H,6.88; N,9.73;
Found: C,75.00; H,6.83; N,9.69%.

EXAMPLE 49
Cis-2,3,6,7,12,12a-hexahydro-2-cyclopropylmethyl-6-(1,2,3,4-tetrahydro-6-naphthyl))-pyrazino[2',1';6,1]pyrido[3,4-b]indole-1,4-dione The same two-step procedure but starting from cyclopropylmethylamine and Intermediate 17 gave, after recrystallization from ethanol/pentane, the title compound as white crystals map.: 125° C.

Analysis for $C_{28}H_{29}N_3O_2$ (0.25 $H_2O$)
Calculated: C,75.73; H,6.70; N,9.46;
Found: C,75.45; H,6.86; N,9.14%.

EXAMPLE 50
Cis-2,3,6,7,12,12a-hexahydro-2-methyl-6-(2-naphthyl)-pyrazino[2',1';6,1]pyrido[3,4-b]indole-1,4-dione The same two-step procedure but starting from methylamine and Intermediate 18 gave, after recrystallization from dichloromethane/methanol, the title compound as white crystals m.p.: >260° C.

Analysis for $C_{25}H_{21}N_3O_2$ (0.25 $H_2O$):
Calculated: C,75.08; H,5.42; N,10.51;
Found: C,75.35; H,5.42; N,10.49%.

EXAMPLE 51
Cis-2,3,6,7,12,12a-hexahydro-2-butyl-6-(2-thienyl)-pyrazino[2',1';6,1]pyrido[3,4-b]indole-1,4-dione The same two-step procedure but starting from butylamine and Intermediate 20 gave, after recrystallization from ethanol, the title compound as white crystals m.p.: 226° C.

Analysis for $C_{22}H_{23}N_3O_2S$:
Calculated: C,67.15; H,5.89; N,10.68;
Found: C,67.39; H,5.88; N,10.77%.

EXAMPLE 52
Cis-2,3,6,7,12,12a-hexahydro-6-(5-bromo-2-thienyl)-2-methyl-pyrazino[2',1';6,1]pyrido[3,4-b]indole-1,4-dione The same two-step procedure but starting from methylamine and Intermediate 24 gave, after recrystallization from ethanol, the title compound as a cream powder m.p.: 258° C.

Analysis for $C_{19}H_{16}BrN_3O_2S$:
Calculated: C,53.03; H,3.75; N,9.76;
Found: C,53.01; H,3.78; N,9.69%.

EXAMPLE 53
Cis-2,3,6,7,12,12a-hexahydro-6-(4-bromo-2-thienyl)-2-methyl-pyrazino[2',1';6,1]pyrido[3,4-b]indole-1,4-dione The same two-step procedure but starting from methylamine and Intermediate 26 gave, after recrystallization from ethanol, the title compound as white crystals m.p.: 292° C.

Analysis for $C_{19}H_{16}BrN_3O_2S$ (0.25 $H_2O$):
Calculated: C,52.48; H,3.82; N,9.66;
Found: C,52.46; H,3.81; N,9.60%.

EXAMPLE 54
Cis-2,3,6,7,12,12a-hexahydro-6-(5-bromo-2-thienyl)-2-cyclopropylmethyl-pyrazino[2',1';6,1]pyrido[3,4-b]indole-1,4-dione The same two-step procedure but starting from cyclopropylmethylamine and Intermediate 24 gave, after recrystallization from ethanol, the title compound as white crystals m.p.: 190° C.

Analysis for $C_{22}H_{20}BrN_3O_2S$:
Calculated: C,56.18; H,4.29; N.8.93;
Found: C,55.92; H,4.28; N,8.74%.

EXAMPLE 55
Cis-2,3,6,7,12,12a-hexahydro-6-(5-bromo-2-thienyl)-2-cyclopentyl-pyrazino[2',1';6,1]pyrido[3,4-b]indole-1,4-dione The same two-step procedure but starting from cyclopentylamine and Intermediate 24 gave, after recrystallization from ethanol, the title compound as white crystals m.p.: 252° C.

Analysis for $C_{23}H_{22}BrN_3O_2S$:
Calculated: C,57.03; H,4.58; N,8.67;
Found: C,56.87; H,4.66; N,8.68%.

EXAMPLE 56
Cis-2,3,6,7,12,12a-hexahydro-2-methyl-6-(5-methyl-2-thienyl)-pyrazino[2',1';6,1]pyrido[3,4-b]indole-1,4-dione The same two-step procedure but starting from methylamine and the cis isomer of Intermediate 66 gave, after recrystallization from ethanol, the title compound as white crystals m.p.: 282° C.

Analysis for $C_{20}H_{19}N_3O_2S$ (0.25 $H_2O$)
Calculated: C,64.93; H,5.31; N,11.36;
Found: C,64.84; H,5.28; N,10.81%.

EXAMPLE 57
Cis-2,3,6,7,12,12a-hexahydro-2-methyl-6-(3-thienyl)-pyrazino[2',1';6,1]pyrido[3,4-b]indole-1,4-dione The same two-step procedure but starting from methylamine and Intermediate 22 gave, after recrystallization from acetone, the title compound as white crystals m.p.: 290–295° C.

Analysis for $C_{19}H_{17}N_3O_2S$:
Calculated: C,64.94; H,4.88; N, 1196;
Found: C,64.81; H,4.95; N,11.68%.

EXAMPLE 58
Cis-2,3,6,7,12,12a-hexahydro-2-butyl-6-(3-thienyl)-pyrazino[2',1';6,1]pyrido[3,4-b]indole-1,4-dione The same two-step procedure but starting from butylamine and Intermediate 22 gave, after recrystallization from methanol, the title compound as white crystals m.p.: 236–239° C.

Analysis for $C_{22}H_{23}N_3O_2S$:
Calculated: C,67.15; H,5.89; N,10.68; S,8.15;
Found: C,67.42; H,5.76; N,10.57; S,8.01%.

EXAMPLE 59
Cis-2,3,6,7,12,12a-hexahydro-2-methyl-6-(3-furyl)-pyrazino[2',1';6,1]pyrido[3,4-b]indole-1,4-dione The same two-step procedure but starting from methylamine and the cis isomer of Intermediate 28 gave, after recrystallization from ether, the title compound as a white solid m.p.: 250° C..

---

The same two-step procedure but starting from methylamine and Intermediate 17 gave, after recrystallization from methanol, the title compound as white crystals m.p.: >260° C.

Analysis for $C_{25}H_{25}N_3O_2$:
Calculated: C,75.16; H,6.31; N,10.52;
Found: C,74.93; H,6.43; N,10.63%.

Analysis for $C_{19}H_{17}N_3O_3$ (0.5 $H_2O$)
Calculated: C,66.27; H,5.27; N,12.20;
Found: C,66.33; H,5.48; N,12.02%.

EXAMPLE 60
Cis-2,3,6,7,12,12a-hexahydro-2-methyl-6-(5-methyl-2-furyl)-pyrazino[2',1';6,1]-pyrido[3,4-b]indole-1,4-dione The same two-step procedure but starting from methylamine and Intermediate 29 gave, after recrystallization from ethanol, the title compound as a cream powder m.p.: 303° C.
Analysis for $C_{20}H_{19}N_3O_3$ (0.25 $H_2O$)
Calculated: C,67.88; H,5.55; N,11.87;
Found: C,67.90; H,5.50; N,11.98%.

EXAMPLE 61
Cis-2,3,6,7,12,12a-hexahydro-2-methyl-6-(4-methylphenyl)-pyrazino[2',1';6,1]pyrido[3,4-b]indole-1,4-dione The same two-step procedure but starting from methylamine and Intermediate 31 gave, after recrystallization from ethanol, the title compound as white crystals m.p.: >260° C.
Analysis for $C_{22}H_{21}N_3O_2$ (0.25 $H_2O$)
Calculated: C,72.61; H,5.95; N,11.55;
Found: C,72.73; H,5.96; N,11.59%.

EXAMPLE 62
Cis-2,3,6,7,12,12a-hexahydro-2-isopropyl-6-(4-methylphenyl)-pyrazino[2',1';6,1]pyrido[3,4-b]indole-1,4-dione The same two-step procedure but starting from isopropylamine and Intermediate 31 gave, after recrystallization from the title compound as white crystals m.p.: 170° C.
Analysis for $C_{24}H_{25}N_3O_2$ (0.5 $H_2O$)
Calculated: C,72.70; H,6.61; N,10.60;
Found: C,73.06; H,6.43; N,9.66%.

EXAMPLE 63
Cis-2,3,6,7,12,12a-hexahydro-2-butyl-6-(4-methylphenyl)-pyrazino[2',1';6,1]pyrido[3,4-b]indole-1,4-dione The same two-step procedure but starting from butylamine and Intermediate 31 gave, after recrystallization from methanol, the title compound as white crystals m.p.: 194° C.
Analysis for $C_{25}H_{27}N_3O_2$ (0.5 $H_2O$)
Calculated: C,73.15; H,6.87; N,10.24;
Found: C,73.01; H,6.84; N,10.26%.

EXAMPLE 64
Cis-2,3,6,7,12,12a-hexahydro-2-cyclopropylmethyl-6-(4-methylphenyl)-pyrazino[2',1';6,1]pyrido[3,4-b]indole-1,4-dione The same two-step procedure but starting from cyclopropylmethylamine and Intermediate 31 gave, after recrystallization from methanol/water, the title compound as white crystals m.p.: 194° C.
Analysis for $C_{25}H_{25}N_3O_2$ (1.1 $H_2O$)
Calculated: C,71.61; H,6.54; N,10.02;
Found: C,71.42; H,6.07; N,9.95%.

EXAMPLE 65
Cis-2,3,6,7,12,12a-hexahydro-2-methyl-6-(3-methylphenyl)-pyrazino[2',1';6,1]pyrido[3,4-b]indole-1,4-dione The same two-step procedure but starting from methylamine and Intermediate 33 gave, after recrystallization from ethanol, the title compound as white crystals m.p.: >260° C.
Analysis for $C_{22}H_{21}N_3O_2$:
Calculated: C,73.52; H,5.89; N,11.69;
Found: C,73.60; H,5.97; N,11.66%.

EXAMPLE 66
Cis-2,3,6,7,12,12a-hexahydro-2-butyl-6-(4-trifluoromethylphenyl)-pyrazino[2',1';6,1]pyrido[3,4-b]indole-1,4-dione The same two-step procedure but starting from butylamine and Intermediate 35 gave, after recrystallization from methanol/water, the title compound as white crystals m.p.: 155° C.
Analysis for $C_{25}H_{24}F_3N_3O_2$ (0.5 $H_2O$)
Calculated: C,64.65; H,5.43; N,9.05;
Found: C,64.78; H,5.40; N,9.01%.

EXAMPLE 67
Cis-2,3,6,7,12,12a-hexahydro-2-methyl-6-(4-trifluoromethoxyphenyl)-pyrazino[2',1';6,1]pyrido[3,4-b]indole-1,4-dione The same two-step procedure but starting from methylamine and the cis isomer of Intermediate 65 gave, after recrystallization from methanol, the title compound as white crystals m.p.: 174–180° C.
Analysis for $C_{22}H_{18}F_3N_3O_3$ (0.5 $H_2O$):
Calculated: C,60.27; H,4.37; N,9.58;
Found: C,60.24; H,4.28; N,9.50%.

EXAMPLE 68
Cis-2,3,6,7,12,12a-hexahydro-2-methyl-6-(4-hydroxyphenyl)-pyrazino[2',1';6,1]pyrido[3,4-b]indole-1,4-dione The same two-step procedure but starting from methylamine and Intermediate 39 gave, after recrystallization from methanol, the title compound as yellow crystals m.p.: 179–180° C..
Analysis for $C_{21}H_{19}N_3O_3$ (1.25 $H_2O$)
Calculated: C,65.70; H,5.64; N,10.94;
Found: C,65.46; H,5.45; N,10.92%.

EXAMPLE 69
Cis-2,3,6,7,12,12a-hexahydro-6-(3-hydroxy-4-methoxyphenyl)-2-methyl-pyrazino[2',1';6,1]pyrido[3,4-b]indole-1 4-dione The same two-step procedure but starting from methylamine and Intermediate 40 gave, after recrystallization from ethanol, the title compound as white crystals m.p.: 320° C.
Analysis for $C_{22}H_{21}N_3O_4$ (0.25 $H_2O$)
Calculated: C,66.74; H,5.47; N,10.61;
Found: C,66.72; H,5.46; N,10.53%.

EXAMPLE 70
Cis-2,3,6,7,12,12a-hexahydro-6-(4-hydroxy-3-methoxyphenyl)-2-methyl-pyrazino[2',1';6,1]pyrido[3,4-b]indole-1,4-dione The same two-step procedure but starting from methylamine and Intermediate 41 gave, after recrystallization from dichloromethane/ethanol, the title compound as yellow crystals m.p.: 264–265° C.
Analysis for $C_{22}H_{21}N_3O_4$:
Calculated: C,67.51; H,5.41; N,10.74;
Found: C,67.05; H,5.41; N,10.62%.

EXAMPLE 71
Cis-2,3,6,7,12,12a-hexahydro-2-butyl-6-(4-cyanophenyl)-pyrazino[2',1';6,1]pyrido[3,4-b]indole-1,4-dione The same two-step procedure but starting from butylamine and Intermediate 37 gave, after recrystallization from methanol/water, the title compound as white crystals m.p.: 246° C.
Analysis for $C_{25}H_{24}N_4O_2$ (1$H_2O$)
Calculated: C,69.75; H,6.09; N,13.01;

Found: C,69.50; H,5.96; N,12.86%.

EXAMPLE 72
Cis-2,3,6,7,12,12a-hexahydro-6-(4-ethylphenyl)-2-isopropyl-pyrazino[2',1';6,1]pyrido[3,4-b]indole-1,4-dione The same two-step procedure but starting from isopropylamine and the cis isomer of Intermediate 42 gave, after recrystallization from n-pentane, the title compound as white crystals m.p.: 130° C.

Analysis for $C_{25}H_{27}N_3O_2$ (0.5 $H_2O$):
Calculated: C,73.15; H,6.87; N,10.24;
Found: C,73.39; H,7.08; N,9.81%.

EXAMPLE 73
Cis-2,3,6,7,12,12a-hexahydro-6-(4-ethylphenyl)-2-cyclopropylmethyl-pyrazino[2',1';6,1]pyrido[3,4-b]indole-1,4-dione The same two-step procedure but starting from cyclopropylmethylamine and the cis isomer of Intermediate 42 gave, after recrystallization from ethanol, the title compound as white crystals m.p.: 160° C.

Analysis for $C_{26}H_{27}N_3O_2$:
Calculated: C,75.52; H,6.58; N,10.16;
Found: C,75.54; H,6.62; N,10.08%.

EXAMPLE 74
Cis-2,3,6,7,12,12a-hexahydro-6-(4-isopropylphenyl)-2-methyl-pyrazino[2',1';6,1]pyrido[3,4-b]indole-1,4-dione The same two-step procedure but starting from methylamine and Intermediate 43 gave, after recrystallization from ethanol, the title compound as white crystals m.p.: 244° C.

Analysis for $C_{24}H_{25}N_3O_2$:
Calculated: C,74.39; H,6.50; N,10.84;
Found: C,74.27; H,6.53; N,11.05%.

EXAMPLE 75
Cis-2,3,6,7,12,12a-hexahydro-2-butyl-6-(4-nitrophenyl)-pyrazino[2',1';6,1]pyrido[3,4-b]indole-1,4-dione The same two-step procedure but starting from butylamine and Intermediate 45 gave, after recrystallization from methanol, the title compound as white crystals m.p.: 182° C.

Analysis for $C_{24}H_{24}N_4O_4$ (0.25 $H_2O$)
Calculated: C,65.97; H,5.65; N,12.82;
Found: C,65.92; H,5.62; N,12.96%.

EXAMPLE 76
Cis-2,3,6,7,12,12a-hexahydro-6-(4-dimethylaminophenyl)-2-methyl-pyrazino[2',1';6,1]pyrido[3,4-b]indole-1,4-dione The same two-step procedure but starting from methylamine and the cis isomer of Intermediate 47 gave after recrystallization from methanol, the title compound as white crystals m.p.: 266° C.

Analysis for $C_{23}H_{24}N_4O_2$:
Calculated: C,71.11; H,6.23; N,14.42;
Found: C,71.19; H,6.24; N,14.34%.

EXAMPLE 77
Cis-2,3,6,7,12,12a-hexahydro-2-methyl-6-(3-pyridyl)-pyrazino[2',1';6,1]pyrido[3,4-b]indole-1,4-dione The same two-step procedure but starting from methylamine and Intermediate 48 gave after recrystallization from chloroform, the title compound as white crystals m.p.: 312° C.

Analysis for $C_{20}H18N_4O_2$:
Calculated: C,69.35; H,5.24; N,16.17;
Found: C,69.08; H,5.20; N,16.19%.

EXAMPLE 78
(6R,12aR)-2,3,6,7,12,12a-Hexahydro-2-methyl-6-(3,4methylenedioxyphenyl)-pyrazino[2',1';6,1]pyrido[3,4-b]-indole-1,4-dione a) To a stirred solution of Intermediate 54 (0.5 g) and $NaHCO_3$ (0.14 g) in anhydrous $CHCl_3$ (20 mL) was added dropwise chloroacetyl chloride (0.27 mL) at 0° C. The resulting mixture was stirred for 1 hour at the same temperature and diluted with $CHCl_3$ (20 mL). Water (10 mL) then was added dropwise with stirring to the mixture, followed by a saturated solution of $NaHCO_3$. The organic layer was washed with water until neutrality and dried over $Na_2SO_4$. After evaporation of the solvent under reduced pressure, (6R,12aR)-methyl 1,2,3,4-tetrahydro-2-chloroacetyl-1-(3,4-methylenedioxyphenyl)-9H-pyrido[3,4-b]indole-3-carboxylate was obtained as an oil which was crystallized from ether to give a solid (0.38 g, m.p.: 233° C.) which was used without further purification in the next step.

b) To a stirred suspension of the chloroacetyl Intermediate (0.37 g) in MeOH (20 mL) was added at room temperature a solution of methylamine (33% in EtOH) (0.4 mL) and the resulting mixture was heated at 50° C. under $N_2$ for 16 hours. The solvent was removed under reduced pressure and the residue was dissolved in $CH_2Cl_2$. After washing with water (3×20 mL), drying over $Na_2SO_4$ and evaporating to dryness, the residue was purified by flash chromatography eluting with $CH_2Cl_2$/MeOH (99/1) and recrystallized from 2-propanol to give the title compound as white crystals (0.22 g) m.p.: 302–303° C.

Analysis for $C_{22}H_{19}N_3O_4$:
Calculated: C,67.86; H,4.92; N,10.79;
Found: C,67.77; H,4.92; N,10.74%.
$[\alpha]_D^{20°}=+71.0°$ (c=1.00; $CHCl_3$).

The following compounds were obtained in a similar manner:

EXAMPLE 79
(6R, 12aR)-2,3,6,7,12,12a-Hexahydro-2-isopropyl-6-(3,4-methylenedioxyphenyl)-pyrazino[2',1';6,1]pyrido[3,4-b]-indole-1,4-dione The same two-step procedure but starting from isopropylamine and Intermediate 54 gave, after recrystallization from methanol, the title compound as white crystals m.p.: 290–293° C.

Analysis for $C_{24}H_{23}N_3O_4$:
Calculated: C,69.05; H,5.55; N,10.07;
Found: C,69.06; H,5.49; N,10.12%.
$[\alpha]_D^{20°}=+52.6°$ (c=1.14; $CHCl_3$)

EXAMPLE 80
(6R,12aR)-2,3,6,7,12,12a-Hexahydro-2-butyl-6-(3,4-methylenedioxyphenyl)-pyrazino[2', 1';6,1]pyrido[3,4-b]-indole-1,4-dione The same two-step procedure but starting from butylamine and Intermediate 54 gave, after recrystallization from toluene/hexane, the title compound as white crystals m.p.: 209–210° C.

Analysis for $C_{25}H_{25}N_3O_4$:
Calculated: C,69.59; H,5.84; N,9.74;
Found: C,69.70; H,5.93; N,9.74%.
$[\alpha]_D^{20°}=+50.2°$ (c=0.53; $CHCl_3$)

EXAMPLE 81
(6R,12aR)-2,3,6,7,12,12a-Hexahydro-2-isobutyl-6-(3,4-methylenedioxyphenyl)-pyrazino[2',1';6,1]pyrido[3,4-b]-indole-1,4-dione The same two-step procedure but starting from isobutylamine and Intermediate 54 gave, after recrystallization from methanol, the title compound as white crystals m.p.: 227–228° C.

Analysis for $C_{25}H_{25}N_3O_4$:
Calculated: C,69.59; H,5.84; N,9.74;

Found: C,69.52; H,5.87; N,9.74%.
$[\alpha]_D^{20°}=+45°$ (c=1.04; CHCl$_3$)

EXAMPLE 82

(6R, 12aR)-2,3,6,7,12,12a-Hexahydro-2-cyclopentyl-6-(3,4-methylenedioxyphenyl)-pyrazino[2',1';6,1]pyrido[3,4-b]-indole-1,4-dione The same two-step procedure but starting from cyclopentylamine and Intermediate 54 gave, after recrystallization from ether, the title compound as white crystals m.p.: 237–239° C.

Analysis for C$_{26}$H$_{25}$N$_3$O$_4$:
Calculated: C,70.41; H,5.68; N,9.47;
Found: C,70.13; H,5.67; N,9.42%.
$[\alpha]_D^{20°}$36.6° (c=0.98; CHCl$_3$)

EXAMPLE 83

(6R, 12aR)-2,3,6,7,12,12a-Hexahydro-6-(3,4-methylenedioxyphenyl)-2-cyclohexylmethyl-pyrazino[2',1';6,1]pyrido[3,4-b]indole-1,4-dione The same two-step procedure but starting from cyclohexylmethylamine and the cis isomer of Intermediate 56 gave, after recrystallization from 2-propanol the title compound as white crystals m.p.: 209° C.

Analysis for C$_{28}$H$_{29}$N$_3$O$_4$:
Calculated: C,71.32; H,6.20; N,8.91;
Found: C,71.30; H,6.29; N,8.74%.
$[\alpha]_D^{20°}=+40.0°$ (c=0.99; CHCl$_3$)

EXAMPLE 84

(6R,12aR)-2,3,6,7,12,12a-Hexahydro-2-cyclopropylmethyl-6-(4-methoxyphenyl)-pyrazino[2',1';6,1]pyrido[3,4-b]indole-1,4-dione The same two-step procedure but starting from cyclopropylmethylamine and Intermediate 57 gave, after recrystallization from methanol, the title compound as white crystals m.p.: 204–205° C.

Analysis for C$_{25}$H$_{25}$N$_3$O$_3$ (0.5 H$_2$O):
Calculated: C,70.74; H,6.17; N,9.90;
Found: C,70.98; H,6.09; N,9.92%.
$[\alpha]_D^{20°}=+54.10$ (c=1.03; CHCl$_3$).

EXAMPLE 85

(6R,12aR)-2,3,6,7,12,12a-Hexahydro-2-butyl-6-(4-methoxyphenyl)-pyrazino[2',1';6,1]pyrido[3,4-b]indole-1,4-dione The same two-step procedure but starting from butylamine and Intermediate 57 gave, after recrystallization from 2-propanol, the title compound as white crystals m.p.: 183–184° C.

Analysis for C$_{25}$H$_{27}$N$_3$O$_3$ (0.5 H$_2$O)
Calculated: C,70.40; H,6.62; N,9.85;
Found: C,70.55; H,6.64; N,9.92%.
$[\alpha]_D^{20°}=+45.40$ (c=1.04; CHCl$_3$)

EXAMPLE 86

(6R, 12aR)-2,3,6,7,12,12a-Hexahydro-2-cyclopentyl-6-(4-methoxyphenyl)-pyrazino[2',1';6,1]pyrido[3,4-b]indole-1,4-dione The same two-step procedure but starting from cyclopentylamine and Intermediate 57 gave, after recrystallization from ether, the title compound as white crystals m.p.: 210–211° C.

Analysis for C$_{26}$H$_{27}$N$_3$O$_3$
Calculated: C,72.71; H,6.34; N,9.78;
Found: C,72.53; H,6.39; N,9.53%.
$[\alpha]_D^{20°}=+29.8°$ (c=1.07; CHCl$_3$)

EXAMPLE 87

(6R,12aR)-2,3,6,7,12,12a-Hexahydro-6-(3-chloro-4-methoxyphenyl)-2-cyclopropylmethyl-pyrazino[2',1';6,1]pyrido[3,4-b]indole-1,4-dione The same two-step procedure but starting from cyclopropylmethylamine and Intermediate 59 gave, after recrystallization from methanol, the title compound as white crystals m.p.: 218–219° C.

Analysis for C$_{25}$H$_{24}$ClN$_3$O$_3$ (0.25 H$_2$O):
Calculated: C,66.08; H,5.43; N,9.25; Cl,7.80;
Found: C,66.11; H,5.33; N,9.03; Cl,7.74%.
$[\alpha]_D^{20°}=+49.4°$ (c=1.03; CHCl$_3$)

EXAMPLE 88

(6R,12aR)-2,3,6,7,12,12a-Hexahydro-2-cyclopentyl-6-(3-chloro-4-methoxyphenyl)-pyrazino[2',1';6,1]pyrido[3,4-b]indole-1,4-dione The same two-step procedure but starting from cyclopentylamine and Intermediate 59 gave, after recrystallization from methanol, the title compound as white crystals m.p.: 260–262° C.

Analysis for C$_{26}$H$_{26}$ClN$_3$O$_3$:
Calculated: C,67.31; H,5.65; Cl,7.64; N,9.06;
Found: C,66.98; H,5.67; Cl,8.06; N,9.04%.
$[\alpha]_D^{20°}=+27.6°$ (c=1.05; CHCl$_3$).

EXAMPLE 89

(6R,12aR)-2,3,6,7,12,12a-Hexahydro-6-(3-chloro-4-methoxyphenyl)-2-methyl-pyrazino[2',1';6,1]pyrido[3,4-b]indole-1,4-dione The same two-step procedure but starting from methylamine and Intermediate 59 gave, after recrystallization from methanol, the title compound as white crystals m.p.: 283–284° C.

Analysis for C$_{22}$H$_{20}$ClN$_3$O$_3$:
Calculated: C,64.47; H,4.92; Cl,8.65; N,10.25;
Found: C,64.49; H,4.92; Cl,8.33; N,10.02%.
$[\alpha]_D^{20°}=+61.3°$ (c=1.00; CHCl$_3$).

EXAMPLE 90

(6R,12aR)-2,3,6,7,12,12a-Hexahydro-2-isopropyl-6-(3-chloro-4-methoxyphenyl)-pyrazino[2',1';6,1]pyrido[3,4-b]indole-1,4-dione The same two-step procedure but starting from isopropylamine and Intermediate 59 gave, after recrystallization from methanol, the title compound as white crystals m.p.: 302–304° C.

Analysis for C$_{24}$H$_{24}$ClN$_3$O$_3$:
Calculated: C,65.83; H,5.52; N,9.60;
Found: C,65.83; H,5.57; N,9.73%.
$[\alpha]_D^{20°}=+39.8°$ (c=0.95; CHCl$_3$).

EXAMPLE 91

(6R,12aR)-2,3,6,7,12,12a-Hexahydro-6-(2,3-dihydrobenzo[b]furan-5-yl)-2-methyl-pyrazino[2',1';6,1]pyrido[3,4-b]indole-1,4-dione The same two-step procedure but starting from methylamine and Intermediate 61 gave, after recrystallization from dichloromethane/methanol, the title compound as white crystals m.p.: 288–291° C.

Analysis for C$_{23}$H$_{21}$N$_3$O$_3$:
Calculated: C,71.30; H,5.46; N,10.85;
Found: C,71.27; H,5.49; N,10.96%.
$[\alpha]_D^{20°}=+65.6°$ (c=0.4; CHCl$_3$).

EXAMPLE 92

(6R, 12aR)-2,3,6,7,12,12a-Hexahydro-6-(2,3-dihydrobenzo[b]furan-5-yl)-2-methylcyclopropyl-pyrazino[2',1';6,1]pyrido[3,4-b]indole-1,4-dione The same two-step procedure but starting from methylcyclopropylamine and Intermediate 61 gave, after recrystallization from methanol, the title compound as white crystals m.p.: 242–244° C.

Analysis for $C_{26}H_{25}N_3O_3$:
Calculated: C,73.05; H,5.89; N,9.83;
Found: C,72.90; H,5.93; N,9.98%.
$[\alpha]_D^{20°}$=+55.4° (c=0.99; CHCl$_3$)

EXAMPLE 93
(6R,12aR)-2,3,6,7,12,12a-Hexahydro-6-(5-indanyl)-2-methyl-pyrazino[2',1';6,1]pyrido[3,4-b]indole-1,4-dione The same two-step procedure but starting from methylamine and Intermediate 63 gave, after recrystallization from methanol, the title compound as white crystals m.p.: 262° C.
Analysis for $C_{24}H_{23}N_3O_2$:
Calculated: C,74.78; H,6.01; N,10.90;
Found: C,74.65; H,5.90; N,10.67%.
$[\alpha]_D^{20°}$=+68.6° (c=0.98; CHCl$_3$)

EXAMPLE 94
(6R,12aR)-2,3,6,7,12,12a-Hexahydro-6-(5-indanyl)-2-cyclopropylmethyl-pyrazino[2',1';6,1]pyrido[3,4-b]indole-1,4-dione The same two-step procedure but starting from cyclopropylmethylamine and Intermediate 63 gave, after recrystallization from methanol, the title compound as white crystals m.p.: 176° C.
Analysis for $C_{27}H_{27}N_3O_2$ (0.25 H$_2$O)
Calculated: C,75.41; H,6.45; N,9.77;
Found: C,75.25; H,6.51; N,9.75%.
$[\alpha]_D^{20°}$=+57.9° (c=1.00; CHCl$_3$)

EXAMPLE 95
(6R,12aR)-2,3,6,7,12,12a-Hexahydro-2-methyl-6-(3,4-methylenedioxyphenyl)-pyrazino[2',1';6,1]pyrido[3,4-b]indole-1,4-dione To a stirred suspension of Intermediate 73 (12.5 g) in MeOH (400 ml) was added at room temperature a solution of methylamine (33% in EtOH) (13.7 ml) and the resulting mixture was heated at 50° C. under N$_2$ for 14 hours. The solvent was removed under reduced pressure and the residue was dissolved in CH$_2$Cl$_2$ (1l). After washing with water (3×500 ml), drying over Na$_2$SO$_4$, and evaporating to dryness, the white solid obtained was recrystallized from 2-propanol to give the title compound as white needles (7.5 g) m.p.: 298–300° C. $[\alpha]_D^{20°}$=+71.30 (c=0.55, CHCl$_3$)
Elemental analysis ($C_{22}H_{19}N_3O_4$)
Calculated: C,67.86; H,4.92; N,10.79;
Found: C,67.79; H,4.95; N,10.61%.

EXAMPLE 96
Cis-2,3,6,7,12,12a-hexahydro-2,10-dimethyl-6-(3,4-methylenedioxyphenyl)-pyrazino[2',1';6,1]pyrido[3,4-b]indole-1,4-dione The same two-step procedure as used to prepare Example 1, but starting from methylamine and the cis isomer of Intermediate 74, gave after recrystallization from ethanol, the title compound as white crystals m.p.: 275° C.
Analysis for $C_{23}H_{21}N_3O_4$ (0.4 H$_2$O)
Calculated: C,67.27; H,5.35; N,10.23;
Found: C,67.36; H,5.21; N,10.31%.

EXAMPLE 97
(6R,12aR)-2,3,6,7,12,12a-Hexahydro-2-(3,4-dimethoxybenzyl)-6-(3,4-methylenedioxyphenyl)-pyrazino[2',1';6,1]pyrido[3,4-b]indole-1,4-dione The same two-step procedure as used to prepare Example 78, but starting from veratrylamine and Intermediate 54 gave, after recrystallization from methanol, the title compound as white crystals m.p.: 224–226° C.
Analysis for $C_{30}H_{27}N_3O_6$:
Calculated: C,68.56; H,5.18; N,8.00;
Found: C,68.80; H,5.11; N,8.06%.
$[\alpha]_D^{20°}$=+43.9° (c=1.02; CHCl$_3$)

EXAMPLE 98
Cis-2,3,6,7,12,12a-hexahydro-6-(4-aminophenyl)-2-butyl-pyrazino[2',1';6,1]pyrido[3,4-b]indole-1,4-dione To a solution of Example 75 (1.5 g) in methanol (100 mL) was added SnCl$_2$·H$_2$O (3.06) and the resulting mixture was heated at reflux for 8 hours. The mixture was cooled to ambient temperature, poured into ice and was adjusted to pH5 with 1N NaOH. The methanol was evaporated off and the residue was basified to pH11 with 1N NaOH and extracted with EtOAc (2×150 mL). After drying over Na$_2$SO$_4$ and evaporation of EtOAc, the resulting yellow powder was purified by radial chromatography eluting with CH$_2$Cl$_2$ to give the title compound as a white powder (550 mg) m.p.: 192° C.
Analysis for $C_{24}H_{26}N_4O_2$ (1.3 H$_2$O)
Calculated: C,67.68; H,6.77; N,13.15;
Found: C,67.74; H,6.68; N,13.02%.

EXAMPLE 99
Cis-2,3,6,7,12,12a-hexahydro-6-(4-acetamidophenyl)-2-butyl-pyrazino[2',1';6,1]pyrido[3,4-b]indole-1,4-dione To a solution of Example 98 (0.2 g) in THF (15 mL) was added triethylamine (76 μl) and acetyl chloride (39 μL) and the resulting solution was stirred at room temperature for 2 hours. After evaporation of THF, the resulting residue was taken up in CH$_2$Cl$_2$ (100 mL), washed with water (2×50 mL), and dried over Na$_2$SO$_4$. After evaporation of CH$_2$Cl$_2$, the resulting solid was recrystallized from MeOH/H$_2$O to give the title compound as a cream powder (120 mg) m.p.: 246° C.
Analysis for $C_{26}H_{28}N_4O_3$:
Calculated: C,70.25; H,6.35; N,12.60;
Found: C,69.85; H,6.38; N,12.56%.

EXAMPLE 100
Cis-2,3,6,7,12,12a-hexahydro-2-butyl-6-(4-methylsulfonamidophenyl)-pyrazino[2',1';6,1]pyrido[3,4-b]indole-1,4-dione To a solution of Example 98 (0.2 g) in THF (5 mL) was added triethylamine (228 μL) and methanesulfonyl chloride (126 μL) and the solution was heated at reflux for 6 hours. After evaporation of THF, the residue was taken up in CH$_2$Cl$_2$, washed with water, and dried over Na$_2$SO$_4$. After evaporation of CH$_2$Cl$_2$, the residue was purified by radial chromatography eluting with CH$_2$Cl$_2$/MeOH (95/5) to give the title compound as a brown powder (30 mg) m.p.: 188° C.
Analysis for $C_{25}H_{28}N_4O_4S$ (0.75 H$_2$O)
Calculated: C,60.77; H,6.02; N,11.34;
Found: C,60.61; H,6.02; N,10.82%.

EXAMPLE 101
(6R,12aR)-2,3,6,7,12,12a-Hexahydro-6-(3,4-methylenedioxyphenyl)-pyrazino[2',1';6,1]pyrido[3,4-b]-indole-1,4-dione The same two-step procedure but starting from ammonia and Intermediate 54 gave, after recrystallization from methanol, the title compound as white crystals m.p.: 285–290° C.
Analysis for $C_{21}H_{17}N_3O_4$:
Calculated: C,67.19; H,4.56; N,11.19;
Found: C,67.30; H,4.66; N,11.11%.
$[\alpha]_D^{20°}$=+88° (c=0.48; pyridine).

EXAMPLE 102
(6R,12aR)-2,3,6,7,12,12a-Hexahydro-6-(3,4-methylenedioxyphenyl)-2-(2-propynyl)-pyrazino[2',1';6,1]-pyrido[3,4-b]indole-1,4-dione The same two-step procedure but starting from propargylamine and Intermediate 54 gave, after recrystallization from acetone, the title compound as white crystals m.p.: 271° C.

Analysis for $C_{24}H_{19}N_3O_4$;
Calculated: C,69.72; H,4.63; N,10.16;
Found: C,69.95; H,4.66; N,10.06%.
$[\alpha]_D^{20°}=+51.7°$ (c=0.49; CHCl$_3$).

EXAMPLE 103

(6R,12aR)-2,3,6,7,12,12a-Hexahydro-2-(3,4-methylendioxybenzyl)-6-(3,4-methylenedioxyphenyl)-pyrazino[2',1';6,1]pyrido[3,4-b]indole-1,4-dione The same two-step procedure but starting from piperonylamine and Intermediate 54 gave, after recrystallization from methanol, the title compound as white crystals m.p.: 204–206° C.

Analysis for $C_{29}H_{23}N_3O_6$:
Calculated: C,68.36; H,4.55; N,8.25;
Found: C,68.25; H,4.49; N,8.41.
$[\alpha]_D^{20°}=+43°$ (c=1.01; CHCl$_3$)

EXAMPLE 104

(6R,12aR)-2,3,6,7,12,12a-Hexahydro-2-(3,4-dimethoxyphenethyl)-6-(3,4-methylenedioxyphenyl)-pyrazino[2',1';6,1]pyrido[3,4-b]indole-1,4-dione The same two-step procedure but starting from 3,4-dimethoxyphenethylamine and Intermediate 54 gave, after recrystallization from dichloromethane/ether, the title compound as white crystals m.p.: 265–266° C.

Analysis for $C_{31}H_{29}N_3O_6$:
Calculated: C,69.00; H,5,42; N,7.79;
Found: C,68.68; H,5.35; N,7.78%.
$[\alpha]_D^{20°}=+38.3°$ (c=1.12 ; CHCl$_3$).

EXAMPLE 105

(6R, 12aR)-2,3,6,7,12,12a-Hexahydro-2-furfuryl-6-(3,4-methylenedioxyphenyl)-pyrazino[2',1';6,1]pyrido[3,4-b]indole-1,4-dione The same two-step procedure but starting from furfurylamine and Intermediate 54 gave, after recrystallization from methanol, the title compound as white crystals m.p.: 219° C.

Analysis for $C_{26}H_{21}N_3O_5$:
Calculated: C,68.56; H,4.65; N,9.23;
Found: C,68.16; H,4.63; N,9.15%.
$[\alpha]_D^{20°}=+58.1°$ (c=1.2; CHCl$_3$)

EXAMPLE 106

(6R 12aR)-2,3,6,7,12,12a-Hexahydro-6-(3,4-methylenedioxyphenyl)-2-(2-thienylmethyl)-pyrazino[2',1';6,1]pyrido[3,4-b]indole-1,4-dione The same two-step procedure but starting from 2-thiophenemethylamine and Intermediate 54 gave, after recrystallization from methanol/water, the title compound as white crystals m.p.: 155–157° C.

Analysis for $C_{26}H_{21}N_3O_4S$:
Calculated: C,66.23; H,4.49; N,8.91; S,6.8;
Found: C,66.13; H,4.54; N,9.12; S,6.78%.
$[\alpha]_D^{20°}=+70.4°$ (c=1.03; CHCl$_3$)

EXAMPLE 107

(6R,12aR)-2,3,6,7,12,12a-Hexahydro-6-(4-methoxyphenyl)-2-methyl-pyrazino[2',1';6,1]pyrido[3,4-b]indole-1,4-dione The same two-step procedure but starting from methylamine and Intermediate 57 gave, after recrystallization from methanol, the title compound as white crystals m.p.: 285–288° C.

Analysis for $C_{22}H_{21}N_3O_3$:
Calculated: C,70.38; H,5.64; N,11.19;
Found: C,70.31; H,5.69; N,11.29%.
$[\alpha]_D^{20°}=+59°$ (c=1.19; CHCl$_3$)

EXAMPLE 108

(6R,12aR)-2,3,6,7,12,12a-Hexahydro-2-ethyl-6-(4-methoxyphenyl)-pyrazino[2',1';6,1]pyrido[3,4-b]indole-1,4-dione The same two-step procedure but starting from ethylamine and Intermediate 57 gave, after recrystallization from methanol, the title compound as white crystals m.p.: 277° C.

Analysis for $C_{23}H_{23}N_3O_3$:
Calculated: C,70.93; H,5.95; N,10.79;
Found: C,70.90; H,5.96; N,10.54%.
$[\alpha]_D^{20°}=+52°$ (c=1.28; CHCl$_3$)

EXAMPLE 109

(6R,12aR)-2,3,6,7,12,12a-hexahydro-6-(7-(4-methyl-3,4-dihydro-2H-benzo[1,4]oxazinyl))-2-methyl-pyrazino[2',1';6,1]pyrido[3,4-b]indole-1,4-dione The same two-step procedure but starting from Intermediate 75 and methylamine gave, after recrystallization from ethanol, the title compound as white crystals m.p.: 285–288° C.

Analysis for $C_{24}H_{24}N_4O_3$ (0.5 H$_2$O)
Calculated: C,67.75; H,5.92; N,13.17;
Found: C,68.02; H,6.00; N,13.18%.
$[\alpha]_D^{20°}=+71.7°$ (c=1, pyridine).

EXAMPLE 110

(6R,12aR)-2,3,6,7,12,12a-Hexahydro-6-(5-(N-benzylindolinyl))-2-methyl-pyrazino[2',1';6,1]pyrido[3,4-b]indole-1,4-dione The same two-step procedure but starting from Intermediate 77 and methylamine gave, after recrystallization from dichloromethane/methanol, the title compound as white crystals m.p.: 223–225° C.

Analysis for $C_{30}H_{28}N_4O_2$:
Calculated: C,75.61; H,5.92; N,11.76;
Found: C,75.2; H,5.78; N,11.67%.
$[\alpha]_D^{20°}=+20.4°$ (c=0.5, CHCl$_3$).

EXAMPLE 111

(6R,12aR)-2,3,6,7,12,12a-Hexahydro-6-(5-indolinyl)-2methyl-pyrazino[2',1';6,1]pyrido[3,4-b]indole-1,4-dione A solution of Example 110 (1.05 g, 2.2 mmol) in methanol (100 mL) was hydrogenated in the presence of 10% Pd-C (100 mg) for 48 hours at room temperature. After removal of the catalyst, the solvent was evaporated in vacuo to leave a residue which was purified by flash chromatography eluting with dichloromethane/methanol: 96/4. The solid obtained was recrystallized from dichloromethane/methanol to give the title compound (300 mg) as white crystals m.p.: 240° C.

Analysis for $C_{23}H_{22}N_4O_2$ (0.5 H$_2$O):
Calculated: C,69.86; H,5.86; N,14.17;
Found: C,70.13; H,5.77; N,14.06%.
$[\alpha]_D^{20°}=+55.9°$ (c=1.18; pyridine).

EXAMPLE 112

Cis-2,3,6,7,12,12a-hexahydro-6-(4-ethylphenyl)-2-methyl-pyrazino[2',1';6,1]pyrido[3,4-b]indole-1,4-dione The same two-step procedure but starting from methylamine and the cis isomer of Intermediate 42 gave, after recrystallization from methanol, the title compound as white crystals m.p.: 254° C.

Analysis for $C_{23}H_{23}N_3O_2$ (0.25 H$_2$O)

EXAMPLE 113

(6R,12aR)-2,3,6,7,12,12a-Hexahydro-6-(4carbomethoxyphenyl)-2-methyl-pyrazino[2',1';6,1]pyrido[3,4-b]indole-1,4-dione The same two-step procedure but starting from Intermediate 78 (cis isomer) and methylamine gave, after recrystallization from methanol, the title compound as white crystals m.p.: 308–312° C.

Analysis for $C_{23}H_{21}N_3O_4$:
Calculated: C,68.47; H,5.25; N,10.42;
Found: C,68.76; H,5.18; N,10.35%.
$[\alpha]_D^{20°}=+97.7°$ (c=1, pyridine)

EXAMPLE 114

(5aR, 12R,14aR)-1,2,3,5a,6,11,12,14a-Octahydro-12-(3,4-methylenedioxyphenyl)-pyrrolo[1", 2";4',5'pyrazino-[2',1';6,1]pyrido[3,4-b]indole-5-1,4-dione A solution of Intermediate 80 (0.7 g, 1.2 mmol) in a mixture of methanol/THF (80/40 mL) was hydrogenated in the presence of 10% Pd—C (75 mg) for 48 hours at 40° C. After removal of the catalyst, the solvent was evaporated in vacuo to leave a residue, which was purified by flash chromatography eluting with dichloromethane/methanol: 98/2. The white solid obtained was recrystallized from methanol to give the title compound (180 mg) as white crystals m.p.: 284–287° C.

Analysis for $C_{24}H_{21}N_3O_4$:
Calculated: C,69.39; H,5.10; N,10.11;
Found: C,69.47; H,5.11; N,9.97%.
$[\alpha]_D^{20°}=+21.70$ (c=0.64, CHCl$_3$)

EXAMPLE 115

(5aR,12R,14aS)-1,2,3,5,6,11,12,14a-Octahydro-12-(3,4-methylenedioxyphenyl)-pyrrolo[1",2";4',5']-pyrazino[2',1';6,1]pyrido[3,4-b]indole-5-1,4-dione A solution of Intermediate 81 (0.8 g, 1.37 mmol) in methanol (40 mL) was hydrogenated in the presence of 10% Pd—C (100 mg) for 5 h at 45° C. After removol of the catalyst the solvent was evaporated in vacuo to leave a residue, which was purified by flash chromatography eluting with dichloromethane/methanol:98/2. The solid obtained was recrystallized from methanol to give the title compound (300 mg) as white crystals m.p.: 302–304° C.

Analysis for $C_{24}H_{21}N_3O_4$:
Calculated: C,69.39; H,5.10; N,10.11;
Found: C,69.35; H,5.11; N,10.10%.
$[\alpha]_D^{20°}=+106.8°$ (c=1.08, CHCl$_3$)

EXAMPLE 116

(3R, 6R,12aR)-2,3,6,7,12,12a-hexahydro-2,3-dimethyl-6-(3,4-methylenedioxyphenyl)-pyrazino[2',1';6,1]pyrido[3,4-b]indole-1,4-dione To a stirred solution of Intermediate 82 (0.15 g, 0.34 mmol) in THF (15 mL) was added at room temperature a solution of methylamine (33% in EtOH) (0.32 mL) and the resulting solution was heated at reflux under N$_2$ for 24 hours. The solvent was removed under reduced pressure and the residue was dissolved in CH$_2$Cl$_2$ (25 mL) After washing with water (2×20 mL), drying over Na$_2$SO$_4$, and evaporating to dryness, the crude product was purified by flash chromatography eluting with dichloromethane/methanol:99/1. The white solid obtained was recrystallized from methanol to give the title compound as white crystals (80 mg) map.: 219–220° C.

Analysis for $C_{23}H_{21}N_3O_4$:
Calculated: C,68.47; H,5.25; N,10.42;
Found: C,68.39; H,5.21; N,10.42%.
$[\alpha]_D^{20°}=+89.6°$ (c=1; CHCl$_3$)

EXAMPLE 117

(3S,6R,12aR)-2,3,6,7,12,12a-hexahydro-2,3-dimethyl-6-(3,4-methylenedioxyphenyl)-pyrazino[2',1';6,1]pyrido[3,4-b]indole-1,4-dione To a stirred solution of Intermediate 83 (0.3 g, 0.68 mmol) in THF (30 mL) was added at room temperature a solution of methylamine (33% in EtOH) (0.68 mL) and the resulting solution was treated at reflux under N$_2$ for 6 days. The solvent was removed under reduced pressure and the residue was dissolved in CH$_2$Cl$_2$ (50 mL). After washing with water (2.25 mL), drying over Na$_2$SO$_4$, and evaporating to dryness, the crude product was purified by flash chromatography eluting with dichloromethane/methanol:99/1. The oily residue obtained was crystallized from methanol to give the title compound as white crystals (40 mg) m.p.: 307–309° C.

Analysis for $C_{23}H_{21}N_3O_4$:
Calculated: C,68.47; H,5.25; N,10.42;
Found: C,68.35; H,5.33; N,10.42%.
$[\alpha]_D^{20°}=+65.2°$ (c=1.15; CHCl$_3$)

EXAMPLE 118

(6R, 12aR)-2,3,6,7,12,12a-Hexahydro-6-(3,4-dihydroxyphenyl)-2-methyl-pyrazino[2',1';6,1]pyrido[3,4-b]indole-1,4-dione A solution of Intermediate 86 (0.75 g; 1.34 mmol) in a mixture of ethanol/THF (70/30 mL) was hydrogenated in the presence of 10% Pd—C (75 mg) for 24 h at room temperature. After removal of the catalyst, the solvent was evaporated in vacuo to leave a white solid which was recrystallizated from methanol to give the title compound (0.35 g) as white crystals m.p.: 224–226° C.

Analysis for $C_{21}H_{19}N_3O_4$:
Calculated: C,66.83; H,5.07; N,11.13;
Found: C,66.58; H,5.01; N,11.04%.
$[\alpha]_D^{20°}=+58.4°$ (c=1.04; pyridine)

EXAMPLE 119

(6R,12aR)-2,3,6,7,12,12a-Hexahydro-2-methyl-6-(5-(2-methylisoindolinyl))pyrazino[2',1';6,1]pyrido[3,4b]indole-1,4-dione The same two steps procedure but starting from Intermediate 87 and methylamine gave a crude oil which was purified by flash chromatography eluting with dichloromethane/methanol/triethylamine:92/8/0.1%. The solid obtained was recrystallized from isopropanol/propyl ether/water to give the title compound (20 mg) as offwhite crystals m.p.: 236° C.

Analysis for $C_{24}H_{24}N_4O_2$ (2.68 H$_2$O)
Calculated: C,64.23; H,6.59; N,12.48;
Found: C,64.21; H,6.43; N,12.02%.
$[\alpha]_D^{20°}=+61.1°$ (c=0.5; CH$_3$OH)

EXAMPLE 120

(6R, 12aR)-2,3,6,7,12,12a-Hexahydro-6-(5-benzofuranyl)-2-methyl-pyrazino[2'1';6,1]pyrido[3,4-b]indole-1,4-dione To a stirred suspension of Intermediate 91 (0.42 g) in methanol (30 mL) was added at ambient temperature a solution of methylamine (33% in EtOH) (0.47 mL) and the resulting mixture was heated at 50° C. under N$_2$ for 72 hours. The solvent was removed under reduced pressure and dissolved in dichloromethane. After washing with water, drying over Na$_2$SO$_4$, and evaporating to dryness, the crude product was purified by crystallization from methanol to give the title compound as white crystals (0.21 g). m.p.: 291–293° C.

Analysis for $C_{23}H_{19}N_3O_3$;
Calculated: C,71.68; H,4.97; N,10.90;
Found: C,71.5; H.4.91; N,10.75%.
$[\alpha]_D^{20°}=+55.7°$ (c=1; CHCl$_3$)

EXAMPLE 121
(6R, 12aR)-2,3,6,7,12,12a-Hexahydro-6-(5-benzofuranyl)-pyrazino[2',1';6,1]pyrido[3,4-b]indole-1,4-dione The same procedure was employed in the preparation of Example 120, but starting from ammonia and Intermediate 91 gave, after recrystallization from methanol, the title compound as white crystals. m.p.: 310–311° C.
Analysis for $C_{22}H_{17}N_3O_3$ (0.4 MeOH);
Calculated: C,70.03; H,4.88; N,10.94;
Found: C,70.01; H,4.8; N,10.61%;
$[\alpha]_d^{20°}=+60.4°$ (c=0.5; pyridine).

EXAMPLE 122
(6R, 12aRP)-2,3,6,7,12,12a-Hexahydro-6-(5-benzofuranyl)-2-isopropyl-pyrazino[2',1';6,1]pyrido[3,4-b]indole-1,4-dione The same procedure as employed in the preparation of Example 120, but starting from isopropylamine and Intermediate 91 gave, after recrystallization from methanol, the title compound as white crystals. m.p.: 291–292° C.
Analysis for $C_{25}H_{23}N_3O_3$ (0.6 MeOH);
Calculated: C,71.06; H,5.92; N,9.71;
Found: C.70.94; H,5.62; N,9.77%.
$[\alpha]_D^{20°}=+37.9°$ (c=1; CHCl$_3$)

EXAMPLE 123
(3S, 6R, 12aR)-2,3,6,7,12,12a-Hexahydro-6-(5-benzofuranyl)-3-methyl-pyrazino2',1';6,1]pyrido[3,4-b]indole-1,4-dione A solution of Intermediate 92 (0.3 g) in the presence of 10% Pd/C (30 mg) in methanol (10 ml) was stirred under an atmosphere of hydrogen at 50° C. for two hours. The reaction mixture was cooled, filtered through Celite, the filter cake washed with methanol, and the filtrate evaporated in vacuo. The residue was purified by flash chromatography, eluting with dichloromethane/methanol (98/2) to give the title compound as white crystals after recrystallization from methanol (0.15 g). m.p.: 150–151° C.
Analysis for $C_{23}H_{19}N_3O_3$ (0.1 MeOH)
Calculated: C,71.39; H,5.03; N,10.81;
Found: C,71.08; H,5.16; N,10.50%;
$[\alpha]_D^{20°}=+50°$ (c=0.25; CHCl$_3$).

EXAMPLE 124
(3S, 6R, 12aR)-2,3,6,7,12,12a-Hexahydro-6-(t-benzofuranyl)-2,3-dimethyl-pyrazino[2',1';6,1]pyrido[3,4-b]indole-1,4-dione The same procedure as employed in the preparation of Example 123, but starting from Intermediate 93 (0.52 g) and using 10% Pd/C (50 mg) in methanol (20 ml) gave, after recrystallization from methanol, the title compound as white crystals (40 mg). m.p.: 323–324° C.
Analysis for $C_{24}H_{21}N_3O_3$ (0.1 Methanol)
Calculated: C,71.52; H,5.35; N,10.43;
Found: C,71.71; H,5.44; N,10.39%;
$[\alpha]_D^{20°}=+53°$ (c=0.35; CHCl$_3$)

EXAMPLE 125
(3S, 6R,12aR)-2,3,6,7,12,12a-Hexahydro-3-methyl-6-(3,4-methylenedioxyphenyl)-pyrazino[2',1';6,1]pyrido[3,4-b]-indole-1,4-dione As white crystals using ammonia as the base, was prepared by the procedure set forth in Example 117. m.p.: 319–321° C.

Analysis for $C_{22}H_{19}N_3O_4$:
Calculated: C,67.86; H,4.92; H,10.79;
Found: C,67.86; H,5.17; N,10.72%.
$[\alpha]_D^{20°}=+107°$ (c=1; pyridine)

Tablets for Oral Administration
A. Direct Compression

| 1. | mg/tablet |
|---|---|
| Active Ingredient | 50.0 |
| Crospovidone USNF | 8.0 |
| Magnesium Stearate Ph Eur | 1.0 |
| Anhydrous Lactose | 141.0 |

The active ingredient was sieved and blended with the excipients. The resultant mix was compressed into tablets.

| 2. | mg/tablet |
|---|---|
| Active Ingredient | 50.0 |
| Colloidal Silicon Dioxide | 0.5 |
| Crospovidone | 8.0 |
| Sodium Lauryl Sulfate | 1.0 |
| Magnesium Stearate Ph Eur | 1.0 |
| Microcrystalline Cellulose USNF | 139.5 |

The active ingredient was sieved and blended with the excipients. The resultant mix was compressed into tablets.

B. Wet Granulation

| 1. | mg/tablet |
|---|---|
| Active ingredient | 50.0 |
| Polyvinylpyrrolidone | 150.0 |
| Polyethylene glycol | 50.0 |
| Polysorbate 80 | 10.0 |
| Magnesium Stearate Ph Eur | 2.5 |
| Croscarmellose Sodium | 25.0 |
| Colloidal Silicon Dioxide | 2.5 |
| Microcrystalline Cellulose USNF | 210.0 |

The polyvinylpyrrolidone, polyethylene glycol, and polysorbate 80 were dissolved in water. The resultant solution was used to granulate the active ingredient. After drying, the granules were screened then extruded at elevated temperatures and pressures. The extrudate was milled and/or screened, then was blended with the microcrystalline cellulose, croscarmellose sodium, colloidal silicon dioxide, and magnesium stearate. The resultant mix was compressed into tablets.

| 2. | mg/tablet |
|---|---|
| Active Ingredient | 50.0 |
| Polysorbate 80 | 3.0 |
| Lactose Ph Eur | 178.0 |
| Starch BP | 45.0 |
| Pregelatinized Maize Starch BP | 22.5 |
| Magnesium Stearate BP | 1.5 |

The active ingredient was sieved and blended with the lactose, starch, and pregelatinized maize starch. The polysorbate 80 was dissolved in purified water. Suitable volumes of the polysorbate 80 solution were added and the powders were granulated. After drying, the granules were screened and blended with the magnesium stearate. The granules were then compressed into tablets.

Tablets of other strengths may be prepared by altering the ratio of active ingredient to the other excipients.

Film Coated Tablets

The aforementioned tablet formulations were film coated.

| Coating Suspension | % w/w |
|---|---|
| Opadry white† | 13.2 |
| Purified water Ph Eur | to 100.0* |

*The water did not appear in the final product. The maximum theoretical weight of solids applied during coating was 20 mg/tablet.
†Opadry white is a proprietary material obtainable from Colorcon Limited, UK, which contains hydroxypropyl methylcellulose, titanium dioxide, and triacetin.

The tablets were film coated using the coating suspension in conventional film coating equipment.

Capsules

| 1. | mg/capsule |
|---|---|
| Active Ingredient | 50.0 |
| Lactose | 148.5 |
| Polyvinylpyrrolidone | 100.0 |
| Magnesium Stearate | 1.5 |

The active ingredient was sieved and blended with the excipients. The mix was filled into size No. 1 hard gelatin capsules using suitable equipment.

| 2. | mg/capsule |
|---|---|
| Active Ingredient | 50.0 |
| Microcrystalline Cellulose | 233.5 |
| Sodium Lauryl Sulfate | 3.0 |
| Crospovidone | 12.0 |
| Magnesium Stearate | 1.5 |

The active ingredient was sieved and blended with the excipients. The mix was filled into size No. 1 hard gelatin capsules using suitable equipment.

Other doses can be prepared by altering the ratio of active ingredient to excipient, the fill weight, and, if necessary, changing th e capsule size.

| 3. | mg/capsule |
|---|---|
| Active Ingredient | 50.0 |
| Labrafil M1944CS | to 1.0 ml |

The active ingredient was sieved and blended with the Labrafil. The suspension was filled into soft gelatin capsules using appropriate equipment.

Inhibitory Effect on cGMP-PDE cGMP-PDE activity of compounds of the present invention was measured using a one-step assay adapted from Wells et al., *Biochim. Biophys. Acta*, 384, 430 (1975). The reaction medium contained 50 mM Tris-HCl, pH 7.5, 5 mM magnesium acetate, 250 μg/ml 5'-Nucleotidase, 1 mM EGTA, and 0.15 μM 8-[H$^3$]-CGMP. The enzyme used was a human recombinant PDE5 (ICOS Corp., Bothell, Wash.). Compounds of the invention were dissolved in DMSO finally present at 2% in the assay. The incubation time was 30 minutes during which the total substrate conversion did not exceed 30%.

The IC$_{50}$ values for the compounds examined were determined from concentration-response curves typically using concentrations ranging from 10 nM to 10 μM. Tests against other PDE enzymes using standard methodology also showed that compounds of the invention are highly selective for the cGMP-specific PDE enzyme.

cGMP Level Measurements

Rat aortic smooth muscle cells (RSMC), prepared according to Chamley et al., *Cell Tissue Res.*, 177, 503–522 (1977), were used between the 10th and 25th passage at confluence in 24-well culture dishes. Culture media was aspirated and replaced with PBS (0.5 ml) containing the compound tested at the appropriate concentration. After 30 minutes at 37° C., particulates guanylate cyclase was stimulated by addition of ANF (100 nM) for 10 minutes. At the end of incubation, the medium was withdrawn, and two extractions were performed by addition of 65% ethanol (0.25 ml). The two ethanolic extracts were pooled and evaporated until dryness, using a Speed-vac system. cGMP was measured after acetylation by scintillation proximity immunoassay (AMERSHAM). The EC$_{50}$ values are expressed as the dose-giving half of the stimulation at saturating concentrations.

Biological Data

The compounds according to the present invention were typically found to exhibit an IC$_{50}$ value of less than 500 nM and an EC$_{50}$ value of less than 5 μM. In vitro test data for representative compounds of the invention is given in the following table:

TABLE 1

In vitro Results

| Example No. | IC$_{50}$ (nM) | EC$_{50}$ (μm) |
|---|---|---|
| 12 | 10 | 0.15 |
| 36 | <10 | 0.5 |
| 52 | 20 | 0.8 |
| 63 | 30 | 0.35 |
| 78 | 2 | 0.2 |
| 79 | <10 | 0.15 |
| 82 | 20 | 0.5 |
| 84 | 10 | 0.4 |
| 89 | 10 | <0.1 |
| 95 | 2 | 0.2 |
| 101 | 10 | 0.3 |
| 115 | <10 | 0.4 |
| 117 | 2 | 0.2 |
| 120 | 15 | 0.6 |
| 121 | 20 | <1 |
| 122 | 30 | <1 |
| 123 | 8 | <1 |
| 124 | 8 | <1 |

The hypotensive effects of compounds according to the invention as identified in Table 2 were studied in conscious spontaneously hypertensive rats (SHRs). The compounds were administered orally at a dose of 5 mg/kg in a mixture of 5% DMF and 95% olive oil. Blood pressure was measured from a catheter inserted in the carotid artery and recorded for five hours after administration. The results are expressed as Area Under the Curve (AUC) from 0 to 5 hours, mm Hg·hours of the fall in blood pressure over time.

TABLE 2

In vivo results

| Example No. | SHR AUC PO (mm Hg.h) |
|---|---|
| 36 | 99 |
| 63 | 95 |
| 79 | 171 |
| 82 | 111 |
| 84 | 77 |
| 89 | 117 |
| 95 | 135 |
| 101 | 136 |
| 120 | 137 |
| 121 | 93 |
| 122 | 108 |
| 123 | 101 |
| 124 | 89 |

Obviously, many modifications and variations of the invention as hereinbefore set forth can be made without departing from the spirit and scope thereof, and, therefore, only such limitations should be imposed as are indicated by the appended claims.

What is claimed is:

1. A combination comprising:
   (a) a compound represented by a formula (I)

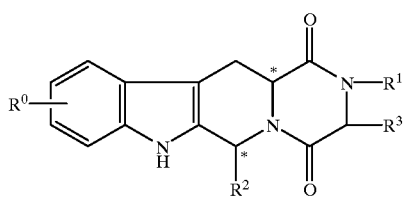

and salts and solvates thereof, in which:
   $R^0$ represents hydrogen, halogen or $C_{1-6}$alkyl;
   $R^1$ represents hydrogen, $C_{1-6}$alkyl, $C_{2-6}$alkenyl, $C_{2-6}$alkynyl, halo$C_{1-6}$alkyl, $C_{3-8}$cycloalkyl, $C_{3-8}$cycloalkyl$C_{1-3}$alkyl, aryl$C_{1-3}$alkyl, or heteroaryl$C_{1-3}$alkyl;
   $R^2$ represents an optionally substituted monocyclic aromatic ring selected from benzene, thiophene, furan, and pyridine or an optionally substituted bicyclic ring

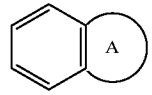

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and
   $R^3$ represents hydrogen or $C_{1-3}$alkyl, or $R^1$ and $R^3$ together represent a 3- or 4- membered alkyl or alkenyl chain; and
   (b) a second therapeutically active agent,
   for simultaneous, separate, or sequential use in the treatment of condition where inhibition of a cGMP-specific PDE is of a therapeutic benefit.

2. A pharmaceutical formulation comprising a combination according to claim 1, together with a pharmaceutically acceptable diluent or carrier.

3. The combination of claim 1 wherein the second therapeutically active agent comprises a vasodilator, prostaglandin E1, prostacyclin, an α-adrenergic blocker, a mixed α,β-blocker, an $α_2$-adrenergic blocker, an ACE inhibitor, an NEP inhibitor, a centrally acting dopaminergic agent, a vasoactive intestinal peptide, a calcium channel blocker, a thiazide, or a mixture thereof.

4. The combination of claim 3 wherein the vasodilator is selected from the group consisting of an organic nitrate, an organic nitrite, a thionitrite, a thionitrate, an S-nitrosothiol, a nitrosoprotein, a substituted furoxane, a substituted sydnonimine, a nitrosyl complex compound, nitric oxide, and a mixture thereof.

5. The combination of claim 3 wherein the vasodilator is selected from the group consisting of nitroglycerin, isosorbide dinitrate, pentaerythrityl tetranitrate, isosorbide-5-mononitrate, propatyl nitrate, trolnitrate, nicroandil, mannitol hexanitrate, inositol hexanitrate, N-[3-nitratopivaloyl]-6-cysteine ethyl ester, isoamyl nitrite, S-nitroso-N-acetyl-D, L-penicillamine, 1,2,5-oxadiazole-2-oxide, furazan-N-oxide, molsidomine, mesocarb, an iron nitrosyl compound, sodium nitroprusside, nitric oxide, and mixtures thereof.

6. The combination of claim 1 wherein the second therapeutically active compound is selected from the group consisting of prostaglandin E1, prostocyclin, apomorphine, yohimbine, phentolamine, prazocin, carvedilol, and mixtures thereof.

7. A method of treating a condition where inhibition of a cGMP-specific PDE is of therapeutic benefit, in a human or a nonhuman animal body, comprising administering to said body a therapeutically effective amount of a combination of claim 1.

8. The method of claim 9 wherein the cGMP-specific PDE is PDE5.

9. The method of claim 7 wherein the condition is erectile dysfunction in a male or female animal.

10. The method of claim 9 wherein the male or female animal is a human male or female animal.

11. The method of claim 7 wherein the treatment is an oral treatment.

12. A method of treating stable angina, unstable angina, variant angina, hypertension, pulmonary hypertension, chronic obstructive pulmonary disease, acute respiratory distress syndrome, malignant hypertension, pheochromocytoma, congestive heart failure, acute renal failure, chronic renal failure, atherosclerosis, a condition of reduced blood vessel patency, a peripheral vascular disease, a vascular disorder, thrombocythemia, an inflammatory disease, myocardial infarction, stroke, bronchitis, chronic asthma, allergic asthma, allergic rhinitis, glaucoma, peptic ulcer, a gut motility disorder, postpercutaneous transluminal coronary or carotid angioplasty, post-bypass surgery graft stenosis, osteoporosis, preterm labor, benign prostatic hypertrophy, or irritable bowel syndrome, in a human or nonhuman animal body, said method comprising administering to said body a therapeutically effective amount of a combination of claim 1.

13. The method of claim 12 wherein the combination is administered orally.

* * * * *

UNITED STATES PATENT AND TRADEMARK OFFICE
CERTIFICATE OF CORRECTION

PATENT NO. : 6,143,746
DATED : November 7, 2000
INVENTOR(S) : Daugan et al.

It is certified that error appears in the above-identified patent and that said Letters Patent is hereby corrected as shown below:

Column 3,
Line 18, "(e.g., 1, 2, or 3" should be -- (e.g., 1, 2, or 3) --

Column 11,
Line 16, "Alpha$\alpha$" should be -- Alpha --

Column 13,
Line 10, "(5aR, 12R, $^{14}$aS) should be -- (5aR, 12R, 14aS) --
Line 10, "12-($^3$, $^4$-" should be -- 12-(3, 4- --
Line 16, "(3S, 6R, 1$^2$aR)" should be -- (3S, 6R, 12aR) --

Column 18,
Line 57, "9H-pyridol" should be -- 9H-pyrido --

Column 20,
Line 58, "tetrahydro-1-14-" should be -- tetrahydro-1- (4- --

Column 21,
Line 13, "$CO_2CH,$)" should be -- $CO_2CH_3$) --
Line 47, "Ethyl 1.2,3,4" should be -- Ethyl 1,2,3,4 --
Line 47, "(4-nitrochenyl)" should be -- (4-nitrophenyl) --

Column 22,
Lines 5 and 6, "5fluorotryptophan" should be -- 5-fluorotryptophan --
Line 59, "124-145SC" should be -- 124-125°C --

Column 26,
Line 22, "(iS, 3R) isomers" should be -- (1S, 3R) isomers --
Line 28, "(1R 3R)" should be -- (1R, 3R) --

Column 28,
Line 50, "starting rom" should be -- starting from --

Column 29,
Line 6, "4methylenedioxyphenyl" should be -- 4-methylenedioxyphenyl --

Column 30,
Line 34, "recrystal35 lization" should be -- recrystallization --
Line 50, "N, 1166;" should be -- N, 11.66; --

UNITED STATES PATENT AND TRADEMARK OFFICE
CERTIFICATE OF CORRECTION

PATENT NO. : 6,143,746
DATED : November 7, 2000
INVENTOR(S) : Daugan et al.

It is certified that error appears in the above-identified patent and that said Letters Patent is hereby corrected as shown below:

Column 31,
Line 32, "pyrazino2', 1';" should be -- pyrazino [2'1': --

Column 33,
Line 19, "C69.54;" should be -- C, 69.54 --

Column 34,
Line 4, "Analysis for $C_2$," should be -- Analysis for $C_{25}$ --
Line 39, "Analysis for $C_2$," should be -- Analysis for $C_{28}$ --

Column 35,
Line 5, "Analysis for $C_2$" should be -- Analysis for $C_{26}$ --
Line 33, "methyl-pvrazino" should be -- methyl-pyrazino --

Column 36,
Line 37, "243-245SC" should be -- 243-245 °C --

Column 38,
Line 48, "N, 1196;" should be -- N, 11.96 --

Column 39,
Line 65, "$C_{22}H_{25}N_3O_2$" should be -- $C_{22}H_{21}N_3O_2$ --

Column 41,
Line 61, "$C_{20}H18N_4O_2$" should be -- $C_{20}H_{18}N_4O_2$ --
Line 66, "4methylenedioxyphenyl" should be -- 4-methylenedioxyphenyl --

Column 43,
Line 14, "$[\alpha]_D^{20°}36.6°$" should be -- $[\alpha]_D^{20°}=+36.6°$ --

Column 46,
Line 25, "76 μnd" should be -- (76 μL) and --
Line 44, "$CH_2Cl_{21}$" should be -- $CH_2Cl_2$, --

Column 47,
Line 32, "H, 5,42;" should be -- H, 5.42; --

Column 48,
Line 45, "2methyl-pyrazino" should be -- 2-methyl-pyrazino --

UNITED STATES PATENT AND TRADEMARK OFFICE
CERTIFICATE OF CORRECTION

PATENT NO.   : 6,143,746
DATED        : November 7, 2000
INVENTOR(S)  : Daugan et al.

It is certified that error appears in the above-identified patent and that said Letters Patent is hereby corrected as shown below:

Column 49,
Line 6, "(4carbomethoxyphenyl)" should be -- (4-carbomethoxyphenyl) --
Line 33, "$[\alpha]_D^{20°}=+21.70$" should be -- $[\alpha]_D^{20°}=+21.7°$ --
Line 65, "(80 mg) map.:" should be -- (80 mg) m.p.: --

Column 50,
Line 49, "offwhite" should be -- off-white --
Line 64, "Na,SO$_4$," should be -- Na$_2$SO$_4$, --

Column 51,
Line 32, "pyrazino2',1';" should be -- pyrazino [2',1': --

Column 54,
Line 41, "EC$_{50}$ (μm)" should be -- EC$_{50}$ (μM) --

Signed and Sealed this

Seventeenth Day of August, 2004

JON W. DUDAS
*Acting Director of the United States Patent and Trademark Office*